United States Patent
Albers et al.

(10) Patent No.: US 6,794,386 B2
(45) Date of Patent: Sep. 21, 2004

(54) β-AMINO ACID COMPOUNDS AS INTEGRIN ANTAGONISTS

(75) Inventors: Markus Albers, Leverkusen (DE); Thomas Lehmann, Bergisch Gladbach (DE); Thomas Rölle, Leverkusen (DE); Gerhard Müller, Krefeld-Fischeln (DE); Gerhard Hessler, Hofheim (DE); Masaomi Tajimi, Kyoto (JP); Karl Ziegelbauer, Kyoto (JP); Hiromi Okigami, Kyoto (JP); Haruki Hasegawa, Kyoto (JP)

(73) Assignee: Bayer Aktiengesellschaft, Leverkusen (DE)

( * ) Notice: Subject to any disclaimer, the term of this patent is extended or adjusted under 35 U.S.C. 154(b) by 81 days.

(21) Appl. No.: 10/168,282

(22) PCT Filed: Dec. 12, 2000

(86) PCT No.: PCT/EP00/12594
§ 371 (c)(1),
(2), (4) Date: Nov. 19, 2002

(87) PCT Pub. No.: WO01/47887
PCT Pub. Date: Jul. 5, 2001

(65) Prior Publication Data
US 2004/0029883 A1 Feb. 12, 2004

(30) Foreign Application Priority Data
Dec. 12, 2000 (DE) .......................... 199 62 936

(51) Int. Cl.[7] .................. A61K 31/5377; C07D 413/14
(52) U.S. Cl. .............................. 514/235.8; 514/252.18; 514/256; 514/318; 514/326; 544/122; 544/296; 544/333; 546/194; 546/210
(58) Field of Search .............. 514/235.8, 252.18, 514/256, 318, 326, 330; 544/122, 296, 333; 546/194, 210, 226

(56) References Cited

U.S. PATENT DOCUMENTS 6,020,347 A * 2/2000 DeLaszlo et al.

FOREIGN PATENT DOCUMENTS

| EP | 0520336 | 12/1992 |
|---|---|---|
| JP | 4334357 | 11/1992 |
| WO | 9853817 | 12/1998 |
| WO | 9925685 | 5/1999 |
| WO | 9964395 | 12/1999 |
| WO | 9967230 | 12/1999 |

OTHER PUBLICATIONS

Nicolaou, K. C., Trujillo, J. I., Jandeleit, B., Chibale, K., Rosenfeld, M., Diefenbach, B., Cheresh, D. A., and Goodman, S. L., "Design, Synthesis and Biological Evaluation of Nonpeptide Integrin Antagonists", Bioorganic & Medicinal Chemistry, 6: 1185–1208 (1998).

Osterkamp, F., Ziemer, B., Koert, U., Wiesner, M., Raddatz, P., and Goodman, S. L., "Synthesis and Biological Evaluation of Integrin Antagonists Containing trans–and cis–2, 5–Disubstituted THF Rings", Chem. Eur. J., 6(4): 666–683 (2000).

* cited by examiner

*Primary Examiner*—Joseph K. McKane
*Assistant Examiner*—Sonya Wright

(57) ABSTRACT

The present invention relates to a compound of the general formula (I),

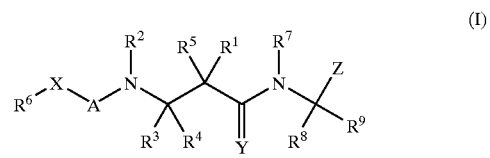

(I)

wherein $R^1$ together with the C atom to which it is attached, and $R^2$ together with the N atom to which it is attached, form a piperidinyl ring; X represents a bond, oxygen or —$NR^{12}$—; and Y represents oxygen; pharmaceutical compositions containing such a compound, as well as the use of such a compound for the production of pharmaceutical compositions, and for the treatment of inflammatory, autoimmune and immune diseases.

6 Claims, No Drawings

β-AMINO ACID COMPOUNDS AS INTEGRIN ANTAGONISTS

The present invention relates to compounds of formula (I),

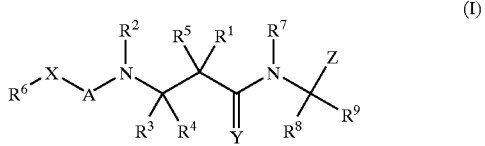

their preparation and use as pharmaceutical compositions as integrin antagonists, especially as $\alpha_4\beta_1$ and/or $\alpha_4\beta_7$ and/or $\alpha_9\beta_1$ integrin antagonists and in particular for the production of pharmaceutical compositions suitable for the inhibiton or the prevention of cell adhesion and cell-adhesion mediated disorders. Examples are the treatment and the prophylaxis of arteriosclerosis, asthma, allergies, diabetes, inflammatory bowel disease, multiple sclerosis, myocardial ischemia, rheumatoid arthritis, transplant rejection and other inflammatory, autoimmune and immune disorders.

Adhesive interactions between the leukocytes and endothelial cells play a critical role in leukocyte trafficking to sites of inflammation. These events are essential for normal host defense against pathogens and repair of tissue damage, but can also contribute to the pathology of a variety of inflammatory and autoimmune disorders. Indeed, eosinophil and T cell infiltration into the tissue is known as a cardinal feature of allergic inflammation such as asthma.

The interaction of circulating leukocytes with adhesion molecules on the luminal surface of blood vessels appears to modulate leukocyte transmigration. These vascular cell adhesion molecules arrest circulating leukocytes, thereby serving as the first step in their recruitment to infected or inflamed tissue sites. Subsequently, the leukocytes reaching the extravascular space interact with connective tissue cells such as fibroblasts as well as extracellular matrix proteins such as fibronectin, laminin, and collagen. Adhesion molecules on the leukocytes and on the vascular endothelium are hence essential to leukocyte migration and attractive therapeutic targets for intervention in many inflammatory disorders.

Leukocyte recruitment to sites of inflammation occurs in a stepwise fashion beginning with leukocyte tethering to the endothelial cells lining the blood vessels. This is followed by leukocyte rolling, activation, firm adhesion, and transmigration. A number of cell adhesion molecules involved in the those four recruitment steps have been identified and characterized to date. Among them, the interaction between VCAM-1 and VLA-4 has been shown to mediate the tethering, rolling, and adhesion of lymphocytes and eosinophils, but not neutrophils, to endothelial cells under a physiologic flow condition. This suggests that the interaction between VCAM-1 and VLA-4 could predominantly mediate a selective recruitment of leukocyte subpopulations in vivo. The inhibition of this interaction is a point of departure for therapeutic intervention.

VCAM-1 is a member of immunoglobulin (Ig) superfamily and is one of the key regulators of leukocyte trafficking to sites of inflammation. VCAM-1, along with ICAM-1 and E-selectin, is expressed on inflamed endothelium activated by such cytokines as IL-1 and TNF-α, as well as by LPS, via NF-κB dependent pathway. However, these molecules are not expressed on resting endothelium. Cell adhesion mediated by VCAM-1 may be involved in numerous physiological and pathological processes including myogenesis, hematopoiesis, inflammatory reactions, and the development of autoimmune disorders. Integrins VLA-4 and α4β7 both function as leukocyte receptors for VCAM-1.

The integrin $\alpha_4\beta_1$ (VLA-4) is a heterodimeric protein expressed in substantial levels on all circulating leukocytes except mature neutrophils. It regulates cell migration into tissues during inflammatory responses and normal lymphocyte trafficking. VLA-4 binds to different primary sequence determinants, such as a QIDSP motif of VCAM-1 and a ELDVP sequence of the major cell type-specific adhesion site of the alternatively spliced type III connecting segment domain (CS-1) of fibronectin.

In vivo studies with neutralizing monoclonal antibodies and inhibitor peptides have demonstrated a critical role for α4 integrins interaction in leukocyte-mediated inflammation. Blocking of VLA-4/ligand interactions, thus, holds promise for therapeutic intervention in a variety of inflammatory, autoimmune and immune diseases (Zimmerman, C.; Exp. Opin. Ther. Patents 1999, 9, 129–133).

Natural ligands for integrin receptors are for example extracellular matrix proteins such as fibronectin, laminin and collagen containing a specific binding sequence. In case of the $\alpha_4\beta_1$ integrin receptor LDV is the specific binding sequence of the natural protein ligands (LDV is the single letter code for the α-amino acid sequence leucine-aspartate-valine [N-terminus→C-terminus]). The most important structural feature for binding is the free carboxylic acid group of the aspartate. Thus, synthetic inhibitors have to mimic the natural binding sequence including a free carboxylic acid group.

Accordingly, compounds containing a dipeptide with a free carboxylic acid C-terminus as structural element were disclosed as $\alpha_4\beta_1$ integrin receptor antagonists, such as WO 98/53817 discloses prolin-phenylalanin [N-terminus→C-terminus] derivatives, WO 98/26921 discloses prolin-β-phenylalanin [N-terminus→C-terminus] derivatives and WO 99/25685 discloses isonipecotic acid (a cyclic γ-amino acid)-phenylalanin [N-terminus→C-terminus] derivatives substituted with a bisarylurea. However, no dipeptide derivatives with a β-amino acid as N-terminus have been described.

β-amino acids have been shown to stabilise helices [D. Seebach, P. E. Ciceri, M. Overhand, B. Jaun, D. Rigo, L. Oberer, U, Hommel, R. Amstutz, H. Widmer Helv. Chim. Acta 1996, 79, 2043–66] and sheet-structures [S. Krauthäuser, L. A. Christianson, D. R. Powell, S. Gellman J. Am. Chem. Soc. 1997, 119, 11719–20] which are completely different from regular secundary structural elements like α-helices or β-sheets which are observed for α-amino acids. Thus β-amino acids show a conformational behavior which is significantly different from natural α-amino acids and it cannot be expected that generally a β-amino acids will mimic corresponding α-amino acids. Consequently, the replacement of a α-amino acid within a biologically active compound containing a peptidic substructure against a β-amino acid will generally disturb the bioactive conformation, yielding compounds with significantly decreased activity.

Surprisingly, however, in the present invention it has now been found that β-amino acid derivatives of formula (I) are potent integrin antagonists, especially $\alpha_4\beta_1$ integrin antagonists.

An object of the present invention is to provide new, alternative, β-amino acid derived integrin antagonists for the treatment of inflammatory, autoimmune and immune diseases.

The present invention therefore relates to compounds of the general formula (I):

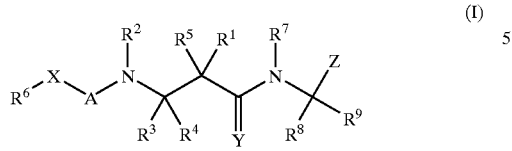

wherein
R$^1$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{10}$, and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals R$^{10}$, wherein
R$^{10}$ represents C$_1$–C$_4$ alkyl, trifluormethyl, trifluormethoxy, —OR$^{11}$, —SR$^{11}$, NR$^{13}$R$^{14}$, —C(O)R$^{11}$, S(O)R$^{11}$, —SO$_2$R$^{11}$, —CO$_2$R$^{11}$, —OC(O)R$^{11}$, —C(O)NR$^{13}$R$^{14}$, —NR$^{11}$C(O)R$^{11}$, —SO$_2$NR$^{13}$R$^{14}$, NR$^{11}$SO$^2$R$^{11}$, —NR$^{11}$C(O)NR$^{13}$R$^{14}$, —NR$^{11}$C(O)OR$^{11}$, —OC(O)NR$^{13}$R$^{14}$, halogen, cyano, nitro or oxo, wherein
R$^{11}$ represents hydrogen, C$_1$–C$_4$ alkyl, C$_3$–C$_6$ cycloalkyl, C$_6$ or C$_{10}$ aryl which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano, and wherein
R$^{13}$ and R$^{14}$ are identical or different and represent hydrogen, C$_1$–C$_4$ alkyl, C$_3$–C$_6$ cycloalkyl, C$_6$ or C$_{10}$ aryl, or
R$^{13}$ and R$^{14}$ together form a 4–7-membered ring, which includes the nitrogen atom to which R$^{13}$ and R$^{14}$ are bonded and which contains up to 2 additional heteroatoms selected from the group oxygen, nitrogen or sulfur and which contains up to 2 double bonds, R$^2$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{15}$, and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals R$^{15}$, wherein
R$^{15}$ represents C$_{1-4}$ alkyl, trifluormethyl, trifluormethoxy, —OR$^{16}$, —SR$^{16}$, NR$^{17}$R$^{18}$, —C(O)R$^{16}$, S(O)R$^{16}$, —SO$_2$R$^{16}$, —CO$_2$R$^{16}$, —OC$_2$(O)R$^{16}$, —C(O)NR$^{17}$R$^{18}$, —NR$^{16}$C(O)R$^{16}$, —SO$_2$NR$^{17}$R$^{18}$, NR$^{16}$SO$_2$R$^{16}$, —NR$^{16}$C(O)NR$^{17}$R$^{18}$, —NR$^{16}$C(O)OR$^{16}$, —OC(O)NR$^{17}$R$^{18}$, halogen, cyano, nitro or oxo, wherein
R$^{16}$ represents hydrogen, C$_1$–C$_4$ alkyl, C$_3$–C$_6$ cycloalkyl, C$_6$ or C$_{10}$ aryl which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano, and wherein
R$^{17}$ and R$^{18}$ are identical or different and represent hydrogen, C$_1$–C$_4$ alkyl, C$_3$–C$_6$ cycloalkyl, C$_6$ or C$_{10}$ aryl, or
R$^{17}$ and R$^{18}$ together form a 4–7-membered ring, which includes the nitrogen atom to which R$^{17}$ and R$^{18}$ are bonded and which contains up to 2 additional heteroatoms selected from the group oxygen, nitrogen or sulfur and which contains up to 2 double bonds, R$^3$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{19}$, and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals R$^{19}$, wherein
R$^{19}$ represents C$_1$–C$_4$ alkyl, trifluormethyl, trifluormethoxy, —OR$^{20}$, —SR$^{20}$, NR$^{21}$R$^{22}$, —C(O)R$^{20}$, S(O)R$^{20}$, —SO$_2$R$^{20}$, —CO$_2$R$^{20}$, —OC(O)R$^{20}$, —C(O)NR$^{21}$R$^{22}$, —NR$^{20}$C(O)R$^{20}$, —SO$_2$NR$^{21}$R$^{22}$, NR$^{20}$SO$_2$R$^{20}$, —NR$^{20}$C(O)NR$^{21}$R$^{22}$, —NR$^{20}$C(O)OR$^{20}$, —OC(O)NR$^{21}$R$^{22}$, halogen, cyano, nitro or oxo, wherein
R$^{20}$ represents hydrogen, C$_1$–C$_4$ alkyl, C$_3$–C$_6$ cycloalkyl, C$_6$ or C$_{10}$ aryl,
which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano, and wherein
R$^{21}$ and R$^{22}$ are identical or different and represent hydrogen, C$_1$–C$_4$ alkyl, C$_3$–C$_6$ cycloalkyl, C$_6$ or C$_{10}$ aryl, or
R$^{21}$ and R$^{22}$ together form a 4–7-membered ring, which includes the nitrogen atom to which R$^{21}$ and R$^{22}$ are bonded and which contains up to 2 additional heteroatoms selected from the group oxygen, nitrogen or sulfur and which contains up to 2 double bonds, R$^4$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{23}$, and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals R$^{23}$, wherein R$^{23}$ represents C$_1$–C$_4$ alkyl, trifluormethyl, trifluormethoxy, —OR$^{24}$, —SR$^{24}$, NR$^{25}$R$^{26}$, —C(O)R$^{24}$, S(O)R$^{24}$, —SO$_2$R$^{24}$, —CO$_2$R$^{24}$, —OC(O)R$^{24}$, —C(O)NR$^{25}$R$^{26}$, —NR$^{24}$C(O)R$^{24}$, —SO$_2$NR$^{25}$R$^{26}$, NR$^{24}$SO$_2$R$^{24}$, —NR$^{24}$C(O)NR$^{25}$R$^{26}$, —NR$^{24}$C(O)OR$^{24}$, —OC(C)NR$^{25}$R$^{26}$, halogen, cyano, nitro or oxo,
wherein
  R$^{24}$ represents hydrogen, C$_1$–C$_4$ alkyl, C$_3$–C$_6$ cycloalkyl, C$_6$ or C$_{10}$ aryl which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano, and
wherein
  R$^{25}$ and R$^{26}$ are identical or different and represent hydrogen, C$_{1-4}$ alkyl, C$_3$–C$_6$ cycloalkyl, C$_6$ or C$_{10}$ aryl,
or
  R$^{25}$ and R$^{26}$ together form a 4–7-membered ring, which includes the nitrogen atom to which R$^{25}$ and R$^{26}$ are bonded and which contains up to 2 additional heteroatoms selected from the group oxygen, nitrogen or sulfur and which contains up to 2 double bonds,
R$^5$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{27}$, and which can furthermore be single-foldedly substituted by C$_3$–C$_7$ cycloalkyl, C$_6$ or C$_{10}$ aryl, C$_4$–C$_9$ heteroaryl or a heterocyclic residue containing up to 2 heteroatoms selected from the group oxygen, nitrogen or sulfur, which can optionally be substituted by 1 to 3 radicals R$^{27}$,
wherein
  R$^{27}$ represents C$_1$–C$_4$ alkyl, trifluormethyl, trifluormethoxy, —OR$^{28}$, —SR$^{28}$, NR$^{29}$R$^{30}$, —C(O)R$^{28}$, S(O)R$^{28}$, —SO$_2$R$^{28}$, —CO$_2$R$^{28}$, —OC(O)R$^{28}$, —C(O)NR$^{29}$R$^{30}$, —NR$^{28}$C(O)R$^{28}$, —SO$_2$NR$^{29}$R$^{30}$, NR$^{28}$SO$_2$R$^{28}$, —NR$^{28}$C(O)NR$^{29}$R$^{30}$, —NR$^{28}$C(O)OR$^{28}$, —OC(O)NR$^{29}$R$^{30}$, halogen, cyano, nitro or oxo,
  wherein
    R$^{28}$ represents hydrogen, C$_1$–C$_4$ alkyl, C$_3$–C$_6$ cycloalkyl, C$_6$ or C$_{10}$ aryl which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano,
    and wherein R$^{29}$ and R$^{30}$ are identical or different and represent hydrogen, C$_1$–C$_4$ alkyl, C$_3$–C$_6$ cycloalkyl, C$_6$ or C$_{10}$ aryl, or
    R$^{29}$ and R$^{30}$ together form a 4–7-membered ring, which includes the nitrogen atom to which R$^{29}$ and R$^{30}$ are bonded and which contains up to 2 additional heteroatoms selected from the group oxygen, nitrogen or sulfur and which contains up to 2 double bonds,
R$^6$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{31}$ and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, or be benzo-fused, which can optionally be substituted by 1 to 3 radicals R$^{31}$, wherein
  R$^{31}$ represents C$_1$–C$_4$ alkyl, trifluormethyl, trifluormethoxy, —OR$^{32}$, —SR$^{32}$, NR$^{33}$R$^{34}$, —C(O)R$^{32}$, S(O)R$^{32}$, —SO$_2$R$^{32}$, —CO$_2$R$^{32}$, —OC(O)R$^{32}$, —C(O)NR$^{33}$R$^{34}$, —NR$^{32}$C(O)R$^{32}$, —SO$_2$NR$^{33}$R$^{34}$, NR$^{32}$SO$_2$R$^{32}$, —NR$^{32}$C(O)NR$^{33}$R$^{34}$, —NR$^{32}$C(O)OR$^{32}$, —OC(O)NR$^{33}$R$^{34}$, halogen, cyano, nitro or oxo,
  wherein
    R$^{32}$ represents hydrogen, C$_1$–C$_4$ alkyl, C$_3$–C$_6$ cycloalkyl, C$_6$ or C$_{10}$ aryl which can optionally be substituted by 1 to 3 substituents selected from the group C$_1$–C$_4$ alkyl, C$_1$–C$_4$ alkyloxy, phenyl, C$_3$–C$_6$ cycloalkyl, halogen, nitro, cyano,
    and wherein R$^{33}$ and R$^{34}$ are identical or different and represent hydrogen, C$_1$–C$_4$ alkyl, C$_3$–C$_6$ cycloalkyl, C$_6$ or C$_{10}$ aryl or a 4–9-membered saturated or unsaturated heterocyclic residue containing up to 2 heteroatoms selected from the group oxygen, nitrogen or sulfur, which can optionally be substituted by 1 to 2 substituents selected from the group C$_1$–C$_4$ alkyl, phenyl, C$_3$–C$_7$ cycloalkyl, C$_1$–C$_4$ alkyloxy, halogen, nitro, cyano,
  or
    R$^{33}$ and R$^{34}$ together form a 4–7-membered ring, which includes the nitrogen atom to which R$^{33}$ and R$^{34}$ are bonded and which contains up to 2 additional heteroatoms selected from the group oxygen, nitrogen or sulfur and which contains up to 2 double bonds, which can optionally be substituted by 1 to 2 substituents selected from the group C$_1$–C$_4$ alkyl, phenyl, benzyl, C$_3$–C$_7$ cycloalkyl, C$_1$–C$_4$ alkyloxy, halogen, nitro, cyano, oxo,
R$^7$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals R$^{35}$, and which can furthermore be single-foldedly substituted by C$_3$–C$_7$ cycloalkyl, C$_6$ or C$_{10}$ aryl, C$_4$–C$_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals R$^{35}$,
wherein
  R$^{35}$ represents C$_1$–C$_4$ alkyl, trifluormethyl, trifluormethoxy, —OR$^{36}$, —SR$^{36}$ NR$^{37}$R$^{38}$, —C(O)R$^{36}$, S(O)R$^{36}$, —SO$_2$R$^{36}$, —CO$_2$R$^{36}$, —OC(O)R$^{36}$, —C(O)NR$^{37}$R$^{38}$, —NR$^{36}$C(O)R$^{36}$, —SO$_2$NR$^{37}$R$^{38}$, NR$^{36}$SO$_2$R$^{36}$, —NR$^{36}$C(O)NR$^{37}$R$^{38}$, —NR$^{36}$C(O)OR$^{36}$, —OC(O)NR$^{37}$R$^{38}$, halogen, cyano, nitro or oxo,
wherein
  R$^{36}$ represents hydrogen, C$_1$–C$_4$ alkyl, C$_3$–C$_6$ cycloalkyl, C$_6$ or C$_{10}$ aryl which can optionally be substituted by 1 substituent selected from the group C$_1$–C$_4$ alkyl, C$_1$–C$_4$ alkyloxy, phenyl, C$_3$–C$_6$ cycloalkyl, halogen, nitro, cyano, and wherein R$^{37}$ and R$^{38}$ are identical or different and represent hydrogen, C$_1$–C$_4$ alkyl, C$_3$–C$_6$ cycloalkyl, C$_6$ or C$_{10}$ aryl,
or
  R$^{37}$ and R$^{38}$ together form a 4–7-membered ring, which includes the nitrogen atom to which R$^{37}$ and R$^{38}$ are bonded and which contains up to 2 additional heteroatoms selected from the group oxygen, nitrogen or sulfur and which contains up to 2 double bonds,
R$^8$ represents hydrogen, C$_1$–C$_{10}$ alkyl, C$_2$–C$_{10}$ alkenyl, C$_2$–C$_{10}$ alkynyl, C$_6$ or C$_{10}$ aryl, C$_3$–C$_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{39}$, and which can furthermore be single-foldedly substituted by $C_3$–$C_7$ cycloalkyl, $C_6$ or $C_{10}$ aryl, $C_4$–$C_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals $R^{39}$, wherein $R^{39}$ represents $C_1$–$C_4$ alkyl, trifluormethyl, trifluormethoxy, —$OR^{40}$, —$SR^{40}$, $NR^{41}R^{42}$, $C(O)R^{40}$, $S(O)R^{40}$, —$SO_2R^{40}$, —$CO_2R^{40}$, —$OC(O)R^{40}$, —$C(O)NR^{41}R^{42}$, —$NR^{40}C(O)R^{40}$, —$SO_2NR^{41}R^{42}$, $NR^{40}SO_2R^{40}$, —$NR^{40}C(O)NR^{41}R^{42}$, —$NR^{40}C(O)OR^{40}$, —$OC(O)NR^{41}R^{42}$, halogen, cyano, nitro or oxo, wherein $R^{40}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{41}$ and $R^{42}$ are identical or different and represent hydrogen, $C_1$–$C_4$ alkyl, $C_3$–$C_6$ cycloalkyl, $C_6$ or $C_{10}$ aryl, or $R^{41}$ and $R^{42}$ together form a 4–7-membered ring, which includes the nitrogen atom to which $R^{41}$ and $R^{42}$ are bonded and which contains up to 2 additional heteroatoms selected from the group oxygen, nitrogen or sulfur and which contains up to 2 double bonds, $R^9$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can furthermore be single-foldedly substituted by $C_3$–$C_7$ cycloalkyl, $C_6$ or $C_{10}$ aryl, $C_4$–$C_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals $R^{43}$, and which can furthermore be single-foldedly substituted by $C_3$–$C_7$ cycloalkyl, $C_6$ or $C_{10}$ aryl, $C_4$–$C_9$ heteroaryl or a 4–9-membered saturated or unsaturated heterocyclic residue containing up to 2 heteroatoms selected from the group oxygen, nitrogen or sulfur, which can optionally be substituted by 1 to 3 radicals $R^{43}$, wherein $R^{43}$ represents $C_1$–$C_4$ alkyl, trifluormethyl, trifluormethoxy, —$OR^{44}$, —$SR^{44}$, $NR^{45}R^{46}$, —$C(O)R^{44}$, $S(O)R^{44}$, —$SO_2R^{44}$, —$CO_2R^{44}$, —$OC(O)R^{64}$, —$C(O)NR^{45}R^{46}$, —$NR\ C(O)R^{44}$, —$SO_2NR^{45}R^{46}$, $NR^{44}SO_2R^{44}$, —$NR^{44}C(O)NR^{45}R^{46}$, —$NR^{44}C(O)OR^{44}$, —$OC(O)NR^{45}R^{46}$, halogen, cyano, tetrazolyl, nitro or oxo, wherein $R^{44}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{45}$ and $R^{46}$ are identical or different and represent hydrogen, $C_1$–$C_{10}$alkyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can furthermore be substituted by $C_1$–$C_{10}$ alkyl, $C_3$–$C_7$ cycloalkyl, $C_6$ or $C_{10}$ aryl, benzyl, diphenylmethyl, $C_4$–$C_9$ heteroaryl or a 4–9-membered saturated or unsaturated heterocyclic residue containing up to 2 heteroatoms selected from the group oxygen, nitrogen or sulfur, or $R^{45}$ and $R^{46}$ together form a 4–7-membered ring, which includes the nitrogen atom to which $R^{45}$ and $R^{46}$ are bonded and which contains up to 2 additional heteroatoms selected from the group oxygen, nitrogen or sulfur and which contains up to 2 double bonds, which can furthermore be substituted by $C_1$–$C_{10}$ alkyl, $C_3$–$C_7$ cycloalkyl, $C_6$ or $C_{10}$ aryl, benzyl, diphenylmethyl, $C_4$–$C_9$ heteroaryl or a 4–9-membered saturated or unsaturated heterocyclic residue containing up to 2 heteroatoms selected from the group oxygen, nitrogen or sulfur, which can be fused with a 3–7 membered homocyclic or heterocyclic, saturated or unsaturated ring, or $R^1$ and $R^2$ or $R^4$ and $R^2$ or $R^6$ and $R^{12}$ together form a 4–7-membered ring, which includes the nitrogen atom to which $R^2$ or $R^6$ and $R^{12}$ can be attached and which contains up to 2 additional heteroatoms selected from the group oxygen, nitrogen or sulfur and containing up to 2 double bonds, and which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, and which can be fused with a 3–7 membered homocyclic or heterocyclic, saturated or unsaturated ring, or $R^1$ and $R^4$ or $R^1$ and $R^5$ or $R^3$ and $R^4$ together form a 4–7-membered ring containing up to 2 heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo and which can be fused with a 3–7 membered homocyclic or heterocyclic, saturated or unsaturated ring, A represents —C(O)—, —C(O)—C(O)—, —C(S)—, —SO—, —$SO_2$—, —PO—, —$PO_2$—, 2-pyrimidyl, 4-pyrimidyl, 2-pyridyl, 2-imidazolyl, 4-imidazolyl, 2-benzimidazolyl or a ring selected from the following group:

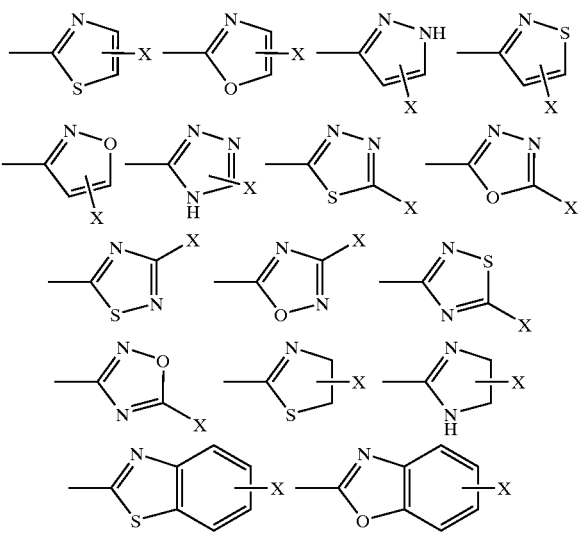

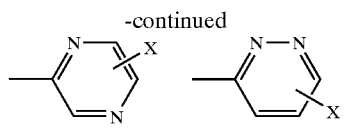

wherein the abovementioned ring systems can optionally be substituted by $C_1$–$C_4$ alkyl, $C_1$–$C_4$ alkoxy, halogen, nitro, cyano, X represents a bond, oxygen or —$NR^{12}$,
wherein
$R^{12}$ represents hydrogen, $C_1$–$C_4$ alkyl, $C_2$–$C_4$ alkenyl, $C_2$–$C_4$ alkynyl which can be optionally substituted by phenyl,
or
together with $R^6$ form a 4–7-membered ring, which includes the nitrogen atom to which $R^6$ and $R^{12}$ can be attached and which can contain up to 2 additional heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, Y represents oxygen or sulfur, Z represents —$C(O)OR^{47}$, $C(O)NR^{48}R^{49}$, —$SO_2NR^{48}R^{49}$, —$SO(OR^{47})$, —$SO_2(OR^{47})$, —$P(O)R^{47}(OR^{49})$, —$PO(OR^{47})(OR^{49})$ or 5-tetrazolyl,
wherein
$R^{48}$ is —$C(O)R^{50}$ or —$SO_2R^{50}$, wherein
$R^{50}$ is $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group halogen, nitro, cyano,
$R^{47}$ and $R^{49}$ are identical or different and represent hydrogen, polymeric resin, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group $C_1$–$C_4$ alkyl, $C_1$–$C_4$ alkyloxy, halogen, nitro, cyano, and pharmaceutically acceptable salts thereof.

A preferred embodiment of the present invention are compounds according the general formula (I),
wherein
$R^1$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{10}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{10}$,
wherein
$R^{10}$ represents $C_1$–$C_4$ alkyl, trifluormethyl, trifluormethoxy, —$OR^{11}$, —$SR^{11}$, $NR^{13}R^{14}$, —$C(O)R^{11}$, $S(O)R^{11}$, —$SO_2R^{11}$, —$CO_2R^{11}$, —$OC(O)R^{11}$, —$C(O)NR^{13}R^{14}$, —$NR^{11}C(O)R^{11}$, —$SO_2NR^{13}R^{14}$, $NR^{11}SO_2R^{11}$, —$NR^{11}C(O)NR^{13}R^{14}$, —$NR^{11}C(O)OR^{11}$, —$OC(O)NR^{13}R^{14}$, halogen, cyano, nitro or oxo,
wherein
$R^{11}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and
wherein $R^{13}$ and $R^{14}$ are identical or different and represent hydrogen, $C_1$–$C_4$ alkyl, $C_3$–$C_6$ cycloalkyl, $C_6$ or $C_{10}$ aryl,
or
$R^{13}$ and $R^{14}$ together form a 4–7-membered ring, which includes the nitrogen atom to which $R^{13}$ and $R^{14}$ are bonded and which contains up to 2 additional heteroatoms selected from the group oxygen, nitrogen or sulfur and which contains up to 2 double bonds, $R^2$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{15}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{15}$,
wherein
$R^{15}$ represents $C_{1-4}$ alkyl, trifluormethyl, trifluormethoxy, —$OR^{16}$, —$SR^{16}$, $NR^{17}R^{18}$, —$C(O)R^{16}$, $S(O)R^{16}$, —$SO_2R^{16}$, —$CO_2R^{16}$, —$OC(O)R^{16}$, —$C(O)NR^{17}R^{18}$, —$NR^{16}C(O)R^{16}$, —$SO_2NR^{17}R^{18}$, $NR^{16}SO_2R^{16}$, —$NR^{16}C(O)NR^{17}R^{18}$, —$NR^{16}C(O)OR^{16}$, —$OC(O)NR^{17}R^{18}$, halogen, cyano, nitro or oxo,
wherein
$R^{16}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and
wherein $R^{17}$ and $R^{18}$ are identical or different and represent hydrogen, $C_1$–$C_4$ alkyl, $C_3$–$C_6$ cycloalkyl, $C_6$ or $C_{10}$ aryl,
or
$R^{17}$ and $R^{18}$ together form a 4–7-membered ring, which includes the nitrogen atom to which $R^{17}$ and $R^{18}$ are bonded and which contains up to 2 additional heteroatoms selected from the group oxygen, nitrogen or sulfur and which contains up to 2 double bonds, $R^3$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{19}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{19}$,
wherein
$R^{19}$ represents $C_1$–$C_4$ alkyl, trifluormethyl, trifluormethoxy, —$OR^{20}$, —$SR^{20}$, $NR^{21}R^{22}$, —$C(O)R^{20}$, $S(O)R^{20}$, —$SO_2R^{20}$, —$CO_2R^{20}$, —$OC(O)R^{20}$, —$C(O)NR^{21}R^{22}$, —$NR^{20}C(O)R^{20}$, —$SO_2NR^{21}R^{22}$, —$NR^{20}SO_2R^{20}$, —$NR^{20}C(O)NR^{21}R^{22}$, —$NR^{20}C(O)OR^{20}$, —$OC(O)NR^{21}R^{22}$, halogen, cyano, nitro or oxo, wherein
- $R^{20}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and
- wherein $R^{21}$ and $R^{22}$ are identical or different and represent hydrogen, $C_1$–$C_4$ alkyl, $C_3$–$C_6$ cycloalkyl, $C_6$ or $C_{10}$ aryl, or
- $R^{21}$ and $R^{22}$ together form a 4–7-membered ring, which includes the nitrogen atom to which $R^{21}$ and $R^{22}$ are bonded and which contains up to 2 additional heteroatoms selected from the group oxygen, nitrogen or sulfur and which contains up to 2 double bonds,
- $R^4$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{23}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{23}$, wherein
- $R^{23}$ represents $C_1$–$C_4$ alkyl, trifluormethyl, trifluormethoxy, —$OR^{24}$, —$SR^{24}$, $NR^{25}R^{26}$, —$C(O)R^{24}$, $S(O)R^{24}$, —$SO_2R^{24}$, —$CO_2R^{24}$, —$OC(O)R^{24}$, —$C(O)NR^{25}R^{26}$, —$NR^{24}C(O)R^{24}$, —$SO_2NR^{25}R^{26}$, $NR^{24}SO_2R^{24}$, —$NR^{24}C(O)NR^{25}R^{26}$, —$NR^{24}C(O)OR^{24}$, —$OC(O)NR^{25}R^{26}$, halogen, cyano, nitro or oxo, wherein
- $R^{24}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein
- $R^{25}$ and $R^{26}$ are identical or different and represent hydrogen, $C_{1\text{-}4}$ alkyl, $C_3$–$C_6$ cycloalkyl, $C_6$ or $C_{10}$ aryl, or
- $R^{25}$ and $R^{26}$ together form a 4–7-membered ring, which includes the nitrogen atom to which $R^{25}$ and $R^{26}$ are bonded and which contains up to 2 additional heteroatoms selected from the group oxygen, nitrogen or sulfur and which contains up to 2 double bonds,
- $R^5$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{27}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{27}$, wherein
- $R^{27}$ represents $C_1$–$C_4$ alkyl, trifluormethyl, trifluormethoxy, —$OR^{28}$, —$SR^{28}$, $NR^{29}R^{30}$, —$C(O)R^{28}$, $S(O)R^{28}$, —$SO_2R^{28}$, —$CO^2R^{28}$, —$OC(O)R^{28}$, —$C(O)NR^{29}R^{30}$, —$NR^{28}C(O)R^{28}$, —$SO_2NR^{29}R^{30}$, $NR^{28}SO_2R^{28}$, —$NR^{28}C(O)NR^{29}R^{30}$, —$NR^{28}C(O)OR^{28}$, —$OC(O)NR^{29}R^{30}$, halogen, cyano, nitro or oxo, wherein
- $R^{28}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein
- $R^{29}$ and $R^{30}$ are identical or different and represent hydrogen, $C_1$–$C_4$ alkyl, $C_3$–$C_6$ cycloalkyl, $C_6$ or $C_{10}$ aryl, or
- $R^{29}$ and $R^{30}$ together form a 4–7-membered ring, which includes the nitrogen atom to which $R^{29}$ and $R^{30}$ are bonded and which contains up to 2 additional heteroatoms selected from the group oxygen, nitrogen or sulfur and which contains up to 2 double bonds,
- $R^6$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{31}$ and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, or be benzo-fused, which can optionally be substituted by 1 to 3 radicals $R^{31}$, wherein
- $R^{31}$ represents $C_1$–$C_4$ alkyl, trifluormethyl, trifluormethoxy, —$OR^{32}$, —$SR^{32}$, $NR^{33}R^{34}$, —$C(O)R^{32}$, $S(O)R^{32}$, —$SO_2R^{32}$, —$CO_2R^{32}$, —$OC(O)R^{32}$, —$C(O)NR^{33}R^{34}$, —$NR^{32}C(O)R^{32}$, —$SO_2NR^{33}R^{34}$, —$NR^{32}SO_2R^{32}$, —$NR^{32}C(O)NR^{33}R^{34}$, —$NR^{32}C(O)OR^{32}$, —$OC(O)NR^{33}R^{34}$, halogen, cyano, nitro or oxo, wherein
- $R^{32}$ represents hydrogen, $C_1$–$C_4$ alkyl, $C_{3-C6}$ cycloalkyl, $C_6$ or $C_{10}$ aryl which can optionally be substituted by 1 to 3 substituents selected from the group $C_1$–$C_4$ alkyl, $C_1$–$C_4$ alkyloxy, phenyl, $C_3$–$C_6$ cycloalkyl, halogen, nitro, cyano, and wherein
- $R^{33}$ and $R^{34}$ are identical or different and represent hydrogen, $C_1$–$C_4$ alkyl, $C_3$–$C_6$ cycloalkyl, $C_6$ or $C_{10}$ aryl or a 4–9-membered saturated or unsaturated heterocyclic residue containing up to 2 heteroatoms selected from the group oxygen, nitrogen or sulfur, which can optionally be substituted by 1 to 2 substituents selected from the group $C_1$–$C_4$ alkyl, phenyl, $C_3$–$C_7$ cycloalkyl, $C_1$–$C_4$ alkyloxy, halogen, nitro, cyano, or
- $R^{33}$ and $R^{34}$ together form a 4–7-membered ring, which includes the nitrogen atom to which $R^{33}$ and $R^{34}$ are bonded and which contains up to 2 additional heteroatoms selected from the group oxygen, nitrogen or sulfur and which contains up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo,
- $R^7$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{35}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{35}$, wherein $R^{35}$ represents $C_1$–$C_4$ alkyl, trifluormethyl, trifluormethoxy, —$OR^{36}$, —$SR^{36}$, $NR^{37}R^{38}$, —$C(O)R^{36}$, $S(O)R^{36}$, —$SO_2R^{36}$, —$CO_2R^{36}$, —$OC(O)R^{36}$, —$C(O)NR^{37}R^{38}$, —$NR^{36}C(O)R^{36}$, —$SO_2NR^{37}R^{38}$, $NR^{36}SO_2R^{36}$, —$NR^{36}C(O)NR^{37}R^{38}$, —$NR^{36}C(O)OR^{36}$, —$OC(O)NR^{37}R^{38}$, halogen, cyano, nitro or oxo, wherein $R^{36}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{37}$ and $R^{38}$ are identical or different and represent hydrogen, $C_1$–$C_4$ alkyl, $C_3$–$C_6$ cycloalkyl, $C_6$ or $C_{10}$ aryl, or $R^{37}$ and $R^{38}$ together form a 4–7-membered ring, which includes the nitrogen atom to which $R^{37}$ and $R^{38}$ are bonded and which contains up to 2 additional heteroatoms selected from the group oxygen, nitrogen or sulfur and which contains up to 2 double bonds, $R^8$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulphur, which can optionally be substituted by 1 to 3 radicals $R^{39}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{39}$, wherein $R^{39}$ represents $C_1$–$C_4$ alkyl, trifluormethyl, trifluormethoxy, —$OR^{40}$, —$SR^{40}$, $NR^{41}R^{42}$, —$C(O)R^{40}$, $S(O)R^{40}$, —$SO_2R^{40}$, —$CO_2R^{40}$, —$OC(O)R^{40}$, —$C(O)NR^{41}R^{42}$, —$NR^{40}C(O)R^{40}$, —$SO_2NR^{41}R^{42}$, $NR^{40}SO_2R^{40}$, —$NR^{40}C(O)NR^{41}R^{42}$, —$NR^{40}C(O)OR^{40}$, —$OC(O)NR^{41}R^{42}$, halogen, cyano, nitro or oxo, wherein $R^{40}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{41}$ and $R^{42}$ are identical or different and represent hydrogen, $C_1$–$C_4$ alkyl, $C_3$–$C_6$ cycloalkyl, $C_6$ or $C_{10}$ aryl, or $R^{41}$ and $R^{42}$ together form a 4–7-membered ring, which includes the nitrogen atom to which $R^{41}$ and $R^{42}$ are bonded and which contains up to 2 additional heteroatoms selected from the group oxygen, nitrogen or sulfur and which contains up to 2 double bonds, $R^9$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{43}$, and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, which can optionally be substituted by 1 to 3 radicals $R^{43}$, wherein $R^{43}$ represents $C_1$–$C_4$ alkyl, trifluormethyl, trifluormethoxy, —$OR^{44}$, —$SR^{44}$, $NR^{45}R^{46}$, —$C(O)R^{44}$, $S(O)R^{44}$, —$SO_2R^{44}$, —$CO_2R^{44}$, —$OC(O)R^{44}$, —$C(O)NR^{45}R^{46}$, —$NR^{44}C(O)R^{44}$, —$SO_2NR^{45}R^{46}$, $NR^{44}SO_2R^{44}$, —$NR^{44}C(O)NR^{45}R^{46}$, —$NR^{44}C(O)OR^{44}$, —$OC(O)NR^{45}R^{46}$, halogen, cyano, tetrazolyl, nitro or oxo, wherein $R^{44}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{45}$ and $R^{46}$ are identical or different and represent hydrogen, $C_1$–$C_4$ alkyl, $C_3$–$C_6$ cycloalkyl, $C_6$ or $C_{10}$ aryl, or $R^{45}$ and $R^{46}$ together form a 4–7-membered ring, which includes the nitrogen atom to which $R^{45}$ and $R^{46}$ are bonded and which contains up to 2 additional heteroatoms selected from the group oxygen, nitrogen or sulfur and which contains up to 2 double bonds, or $R^1$ and $R^2$ or $R^4$ and $R^2$ or $R^6$ and $R^{12}$ together form a 4–7-membered ring, which includes the nitrogen atom to which $R^2$ or $1^6$ and $R^{12}$ can be attached and which contains up to 2 additional heteroatoms selected from the group oxygen, nitrogen or sulfur and containing up to 2 double bonds, and which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, and which can be fused with a 3–7 membered homocyclic or heterocyclic, saturated or unsaturated ring, or $R^1$ and $R^4$ or $R^1$ and $R^5$ or $R^3$ and $R^4$ together form a 4–7-membered ring containing up to 2 heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo and which can be fused with a 3–7 membered homocyclic or heterocyclic, saturated or unsaturated ring, A represents —C(O)—, —C(O)—C(O)—, —C(S)—, —SO—, —$SO_2$—, —PO—, —$PO_2$—, 2-pyrimidyl, 4-pyrimidyl, 2-pyridyl, 2-imidazolyl, 4-imidazolyl, 2-benzimidazolyl or a ring selected from the following group:

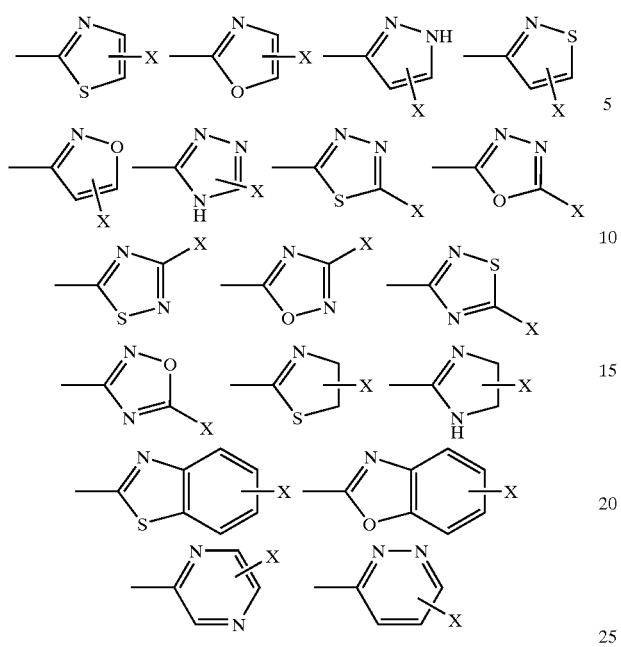

wherein the abovementioned ring systems can optionally be substituted by $C_1$–$C_4$ alkyl, $C_1$–$C_4$ alkoxy, halogen, nitro, cyano, X represents a bond, oxygen or —$NR^{12}$, wherein $R^{12}$ represents hydrogen, $C_1$–$C_4$ alkyl, $C_2$–$C_4$ alkenyl, $C_2$–$C_4$ alkynyl which can be optionally substituted by phenyl, or together with $R^6$ form a 4–7-membered ring, which includes the nitrogen atom to which $R^6$ and $R^{12}$ can be attached and which can contain up to 2 additional heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, Y represents oxygen or sulfur, Z represents —$C(O)OR^{47}$, —$C(O)NR^{48}R^{49}$, —$SO_2NR^{48}R^{49}$, —$SO(OR^{47})$, —$SO_2(OR^{47})$, —$P(O)R^{47}(OR^{49})$, —$PO(OR^{47})(OR^{49})$ or 5-tetrazolyl, wherein $R^{48}$ is —$C(O)R^{50}$ or —$SO_2R^{50}$, wherein $R^{50}$ is $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group halogen, nitro, cyano, $R^{47}$ and $R^{49}$ are identical or different and represent hydrogen, polymeric resin, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group $C_1$–$C_4$ alkyl, $C_1$–$C_4$ alkyloxy, halogen, nitro, cyano, and pharmaceutically acceptable salts thereof.

In another preferred embodiment, the invention relates to compounds of general formula (I), wherein $R^1$, $R^3$, $R^4$ and $R^5$ can be identical or different and represent hydrogen, $C_1$–$C_8$ alkyl, $C_2$–$C_6$ alkenyl, $C_2$–$C_6$ alkynyl, $C_6$ or $C_{10}$ aryl, a 4–9-membered saturated or unsaturated heterocyclic residue containing up to 2 heteroatoms selected from the group oxygen, nitrogen or sulfur, or $C_3$–$C_7$ cycloalkyl which can optionally be substituted by 1 to 2 substituents selected from the group $C_1$–$C_4$ alkyl, phenyl, $C_3$–$C_6$ cycloalkyl, trifluoromethyl, trifluormethoxy, $C_1$–$C_4$ alkoxy, halogen or oxo, $R^2$ and $R^7$ can be identical or different and represent hydrogen, $C_1$–$C_8$ alkyl, $C_2$–$C_6$ alkenyl, $C_2$–$C_6$ alkynyl, $C_6$ or $C_{10}$ aryl or $C_3$–$C_7$ cycloalkyl wherein all the abovementioned groups can optionally be substituted by 1 to 2 substituents selected from the group $C_1$–$C_4$ alkyl, phenyl, $C_3$–$C_7$ cycloalkyl, $C_1$–$C_4$ alkyloxy, $R^6$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{31}$ and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, or benzo-fused, which can optionally be substituted by 1 to 3 radicals $R^{31}$, wherein $R^{31}$ represents $C_1$–$C_4$ alkyl, trifluormethyl, trifluormethoxy, —$OR^{32}$, —$SR^{32}$, $NR^{33}R^{34}$, —$C(O)R^{32}$, $S(O)R^{32}$, —$SO_2R^{32}$, —$CO_2R^{32}$, —$OC(O)R^{32}$, —$(O)NR^{33}R^{34}$, —$NR^{32}C(O)R^{32}$, —$SO_2NR^{33}R^{34}$, $NR^{32}SO_2R^{32}$, —$NR^{32}C(O)NR^{33}R^{34}$, —$NR^{32}C(O)OR^{32}$, —$OC(O)NR^{33}R^{34}$, halogen, cyano, nitro or oxo, wherein $R^{32}$ represents hydrogen, $C_1$–$C_4$ alkyl, $C_3$–$C_6$ cycloalkyl, $C_6$ or $C_{10}$ aryl which can optionally be substituted by 1 to 3 substituents selected from the group $C_1$–$C_4$ alkyl, $C_1$–$C_4$ alkyloxy, phenyl, $C_3$–$C_6$ cycloalkyl, halogen, nitro, cyano, and wherein $R^{33}$ and $R^{34}$ are identical or different and represent hydrogen, $C_1$–$C_4$ alkyl, $C_3$–$C_6$ cycloalkyl, $C_6$ or $C_{10}$ aryl or a 4–9-membered saturated or unsaturated heterocyclic residue containing up to 2 heteroatoms selected from the group oxygen, nitrogen or sulfur, which can optionally be substituted by 1 to 2 substituents selected from the group $C_1$–$C_4$ alkyl, phenyl, $C_3$–$C_7$ cycloalkyl, $C_1$–$C_4$ alkyloxy, halogen, nitro, cyano, or $R^{33}$ and $R^{34}$ together form a 4–7-membered ring, which includes the nitrogen atom to which $R^{33}$ and $R^{34}$ are bonded and which contains up to 2 additional heteroatoms selected from the group oxygen, nitrogen or sulfur and which contains up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, $R^8$ represents hydrogen, $C_1$–$C_8$ alkyl, $C_2$–$C_6$ alkenyl, $C_2$–$C_6$ alkynyl wherein all the abovementioned groups can optionally be substituted by 1 to 2 substituents selected from the group $C_1$–$C_4$ alkyl, phenyl, $C_3$–$C_7$ cycloalkyl, $C_1$–$C_4$ alkyloxy, $R^9$ represents hydrogen, $C_1$–$C_4$ alkyl, $C_2$–$C_6$ alkenyl, $C_2$–$C_6$ alkynyl, $C_6$ or $C_{10}$ aryl or $C_{3-7}$ cycloalkyl which can furthermore be single-foldedly substituted by $C_3$–$C_7$ cycloalkyl, $C_6$ or $C_{10}$ aryl, $C_4$–$C_9$ heteroaryl containing up to 2 heteroatoms selected from the group oxygen, nitrogen or sulfur, which can furthermore be single-foldedly substituted by $C_3$–$C_7$ cycloalkyl, $C_6$ or $C_{10}$ aryl, $C_4$–$C_9$ heteroaryl containing up to 2 heteroatoms selected from the group oxygen, nitrogen or sulfur, wherein the latter cyclic group can optionally be substituted by 1 to 3 substituents selected from $R^{43}$, wherein $R^{43}$ represents $C_1$–$C_4$ alkyl, trifluormethyl, trifluormethoxy, —$OR^{44}$, —$SR^{44}$, $NR^{45}R^{46}$, —$C(O)R^{44}$, $S(O)R^{44}$, —$SO_2R^{44}$, —$CO_2R^{44}$, —$OC(O)R^{44}$, —$C(O)NR^{45}R^{46}$, —$NR^{44}C(O)R^{44}$, —$SO_2NR^{45}R^{46}$, $NR^{44}SO_2R^{44}$, —$NR^{44}C(O)NR^{45}R^{46}$, —$NR^{44}C(O)OR^{44}$, —$OC(O)NR^{45}R^{46}$, halogen, cyano, tetrazolyl, nitro or oxo, wherein $R^{44}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{45}$ and $R^{46}$ are identical or different and represent hydrogen, $C_1$–$C_4$ alkyl, $C_3$–$C_6$ cycloalkyl, $C_6$ or $C_{10}$ aryl, or $R^{45}$ and $R^4$ together form a 4–7-membered ring, which includes the nitrogen atom to which $R^{45}$ and $R^{46}$ are bonded and which contains up to 2 additional heteroatoms selected from the group oxygen, nitrogen or sulfur and which contains up to 2 double bonds, or $R^1$ and $R^2$ or $R^4$ and $R^2$ or $R^6$ and $R^{12}$ together form a 5–6-membered ring, which includes the nitrogen atom to which $R^2$ or $R^6$ and $R^{12}$ can be attached and which contains up to 1 additional heteroatom selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, or which can be fused with a 5–6-membered homocyclic or heterocyclic saturated ring, or $R^1$ and $R^4$ or $R^1$ and R or $R^3$ and $R^4$ together form a 5–6-membered ring containing up to 1 heteroatom selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo or fused with a 5–6-membered homocyclic or heterocyclic saturated ring, A represents —$C(O)$—, —$C(O)$—$C(O)$—, —$SO$—, —$SO_2$—, —$PO$—, —$PO_2$—, 2-pyrimidyl, 4-pyrimidyl, 2-pyridyl, 2-imidazolyl, 4imidazolyl, 2-benzimidazolyl or a ring selected from the following group:

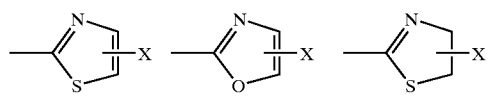

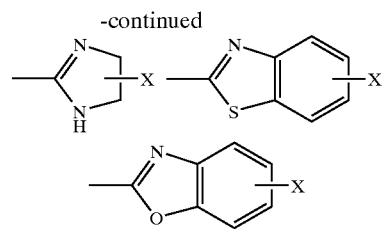

wherein the abovementioned ring systems can optionally be substituted by $C_1$–$C_4$ alkyl, $C_1$–$C_4$ alkyloxy, halogen, nitro, cyano, X represents a bond, oxygen or —$NR^{12}$, wherein $R^{12}$ represents hydrogen, $C_1$–$C_4$ alkyl, $C_2$–$C_4$ alkenyl, $C_2$–$C_4$ alkynyl, which can be optionally substituted by phenyl, or together with $R^6$ form a 4–7-membered ring, which includes the nitrogen atom to which $R^6$ and $R^{12}$ can be attached and which contains up to 2 additional heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, Y represents oxygen or sulfur, Z represents —$C(O)OR^{47}$, —$C(O)NR^{48}R^{49}$, —$SO_2NR^{48}R^{49}$, —$SO(OR^{47})$, —$SO_2(OR^{47})$, —$P(O)R^{47}(OR^{49})$, —$PO(OR^{47})(OR^4)$ or 5-tetazolyl, wherein $R^{48}$ is —$C(O)R^{50}$ or —$SO_2R^{50}$, wherein $R^{50}$ is, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group halogen, nitro, cyano, $R^{47}$ and $R^{49}$ are identical or different and represent hydrogen, polymeric resin, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group $C_1$–$C_4$ alkyl, $C_1$–$C_4$ alkyloxy, halogen, nitro, cyano, and pharmaceutically acceptable salts thereof.

In a particularly preferred embodiment, the invention relates to compounds of general formula (I), wherein $R^1$ and $R^2$ together form a 6-membered ring, which includes the nitrogen atom to which $R^2$ is bonded, $R^3$, $R^4$, $R^5$, $R^7$ and $R^8$ represent hydrogen, $R^6$ represents hydrogen, $C_1$–$C_{10}$ alkyl, $C_3$–$C_6$ cycloalkyl, $C_6$ or $C_{10}$ aryl, which can optionally be substituted by 1 to 3 residues selected from the group methyl, methoxy, halogen, carbonyloxymethyl, trifloromethyl and which can furthermore be single-foldedly substituted by $C_6$ cycloalkyl, phenyl, pyridyl, pyrrolidyl or benzo-fused, which can optionally be substituted by 1 to 3 residues selected from the group methyl, halogen, oxo, or $R^6$ and $R^{12}$ together form a 6-membered ring, which includes the nitrogen atom to which $R^6$ and $R^{12}$ can be attached and which contains up to 1 additional heteroatom selected from the group oxygen or nitrogen, $R^9$ represents $C_1$ alkyl, which is single-foldedly substituted by $C_6$ aryl, which is single-foldedly substituted by $C_6$ aryl, wherein the latter $C_6$ aryl can optionally be substituted by 1 to 2 substituents selected from the group $C_1$ alkyl, $C_1$ alkyloxy or halogen, A represents —C(O)—, —SO$_2$, -2-pyrimidyl, 4-pyrimidyl, 2-pyridyl or 2-benzimidazolyl, wherein the abovementioned ring systems can optionally be single-foldedly substituted by halogen, X represents a bond, oxygen or —NR$^{12}$, wherein $R^{12}$ represents hydrogen, methyl, or together with $R^6$ form a 6-membered ring, which includes the nitrogen atom to which $R^6$ and $R^{12}$ can be attached and which contains up to 1 additional heteroatoms selected from the group oxygen or nitrogen Y represents oxygen, Z represents —C(O)OR$^{47}$, wherein $R^{47}$ represents hydrogen or polymeric resin, and pharmaceutically acceptable salts thereof.

In a particulary preferred embodiment, the invention relates to the compounds general formula (I), wherein A represents 2-pyrimidyl, 4-pyrimidyl, 2-pyridyl, 2-benzimidazolyl, wherein the abovementioned ring systems can optionally be substituted by $C_1$–$C_4$ alkyl, $C_1$–$C_4$ alkoxy, halogen, nitro or cyano.

In another particularly preferred embodiment the present invention relates to the compounds according to general formula (I), wherein A represents —C(O)— or —SO$_2$.

In a very preferred embodiment, the invention relates to compounds of general formula (I)

wherein $R^1$, $R^3$, $R^4$ and $R^5$ can be identical or different and represent hydrogen $C_1$–$C_9$ alkyl, $C_{2-C6}$ alkenyl, $C_2$–$C_6$ alkynyl, 6 or $C_{10}$ aryl, a 4–9-membered saturated or unsaturated heterocyclic residue containing up to 2 heteroatoms selected from the group oxygen, nitrogen or sulfur, or $C_3$–$C_7$ cycloalkyl which can optionally be substituted by 1 to 2 substituents selected from the group $C_1$–$C_4$ alkyl, phenyl, $C_3$–$C_6$ cycloalkyl, trifluormethyl, trifluormethoxy, $C_1$–$C_4$ alkyloxy, halogen or oxo, $R^2$ and $R^7$ can be identical or different and represent hydrogen, $C_1$–$C_8$ alkyl, $C_2$–$C_6$ alkenyl, $C_2$–$C_6$ alkynyl, $C_6$ or $C_{10}$ aryl or $C_3$–$C_7$ cycloalkyl wherein all the abovementioned groups can optionally be substituted by 1 to 2 substituents selected from the group $C_1$–$C_4$ alkyl, phenyl, $C_3$–$C_7$ cycloalkyl, $C_1$–$C_4$ alkyloxy, $R^6$ represents hydrogen, $C_1$–$C_{10}$ alkyl, $C_2$–$C_{10}$ alkenyl, $C_2$–$C_{10}$ alkynyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can optionally be substituted by 1 to 3 radicals $R^{31}$ and which can furthermore be single-foldedly substituted by $C_3$–$C_7$ cycloalkyl, $C_6$ or $C_{10}$ aryl, $C_4$–$C_9$ heteroaryl or a heterocyclic residue containing up to 2 heteroatoms selected from the group oxygen, nitrogen or sulfur, or benzo-fused, which can optionally be substituted by 1 to 3 radicals $R^{31}$, wherein $R^{31}$ represents $C_1$–$C_4$ alkyl, trifluormethyl, trifluormethoxy, —OR$^{32}$, —SR$^{32}$, NR$^{33}$R$^{34}$, —C(O) R$^{32}$, S(O)R$^{32}$, —SO$_2$R$^{32}$, CO$_2$R$^{32}$, —OC(O)R$^{32}$, —C(O)NR$^{33}$R$^{34}$, —NR$^{32}$C(O)R$^{32}$, —SO$_2$NR$^{33}$R$^{34}$, NR$^{32}$SO$_2$R$^{32}$, —NR$^{32}$C(O)NR$^{32}$R$^{34}$, —NR$^{32}$C(O)OR$^{32}$, —OC(O)NR$^{33}$R$^{34}$, halogen, cyano, nitro or oxo, wherein $R^{32}$ represents hydrogen, $C_1$–$C_4$ alkyl, $C_3$–$C_6$ cycloalyl, $C_6$ or $C_{10}$ aryl which can optionally be substituted by 1 to 3 substituents selected from the group $C_1$–$C_4$ alkyl, $C_1$–$C_4$ alkyloxy, phenyl, $C_3$–$C_6$ cycloalkyl, halogen, nitro, cyano, and wherein $R^{33}$ and $R^{34}$ are identical or different and represent hydrogen, $C_1$–$C_4$ alkyl $C_3$–$C_6$ cycloalkyl, $C_6$ or $C_{10}$ aryl or a 4–9-membered saturated or unsaturated heterocyclic residue containing up to 2 heteroatoms selected from the group oxygen, nitrogen or sulfur, which can optionally be substituted by 1 to 2 substituents selected from the group $C_1$–$C_4$ alkyl, phenyl, $C_3$–$C_7$ cycloalkyl, $C_1$–$C_4$ alkyloxy, halogen, nitro, cyano, or $R^{33}$ and $R^{34}$ together form a 4–7-membered ring, which includes the nitrogen atom to which $R^{33}$ and $R^{34}$ are bonded and which contains up to 2 additional heteroatoms selected from the group oxygen, nitrogen or sulfur and which contains up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, $R^8$ represents hydrogen, $C_1$–$C_8$ alkyl, $C_2$–$C_6$ alkenyl, $C_2$–$C_6$ alkynyl, wherein all the abovementioned groups can optionally be substituted by 1 to 2 substituents selected from the group $C_1$–$C_4$ alkyl, phenyl, $C_3$–$C_7$ cycloalkyl, $C_1$–$C_4$ alkyloxy, $R^9$ represents hydrogen, $C_1$–$C_4$ alkyl, $C_2$–$C_6$ alkenyl, $C_2$–$C_6$ alkynyl, $C_6$ or $C_{10}$ aryl or $C_3$–$C_7$ cycloalkyl which can furthermore be single-foldedly substituted by $C_3$–$C_7$ cycloalkyl, $C_6$ or $C_{10}$ aryl, $C_4$–$C_9$ heteroaryl containing up to 2 heteroatoms selected from the group oxygen, nitrogen or sulfur, wherein the latter cyclic group can optionally be substituted by 1 to 3 substituents selected from $R^{43}$, wherein $R^{43}$ represents $C_1$–$C_4$ alkyl, trifluormethyl, trifluormethoxy, —OR$^{44}$, —SR$^{44}$, NR$^{45}$R$^{46}$, —C(O) R$^{44}$, S(O)R$^{44}$, —SO$_2$R$^{44}$, —CO$_2$R$^{44}$, —OC(O)R$^{44}$, —C(O)NR$^{45}$R$^{46}$, —NR$^{44}$C(O)R$^{44}$, —SO$_2$NR$^{45}$R$^{46}$, NR$^{44}$SO$_2$R$^{44}$, —NR$^{44}$C(O)NR$^{45}$R$^{46}$, —NR$^{44}$C(O) OR$^{44}$, —OC(O)NR$^{45}$R$^{46}$, halogen, cyano, tetrazolyl, nitro or oxo, wherein $R^{44}$ represents hydrogen, $C_1$–$C_4$ alkyl, $C_3$–$C_6$ cycloalkyl, $C_6$ or $C_{10}$ aryl which can optionally be substituted by 1 substituent selected from the group $C_1$–$C_4$ alkyl, $C_1$–$C_4$ alkyloxy, phenyl, $C_3$–$C_6$ cycloalkyl, halogen, nitro, cyano, and wherein $R^{45}$ and $R^{46}$ are identical or different and represent hydrogen $C_1$–$C_{10}$ alkyl, $C_6$ or $C_{10}$ aryl, $C_3$–$C_7$ cycloalkyl or a 4–9-membered saturated or unsaturated heterocyclic residue containing up to 2 heteroatoms selected from the group oxygen, nitrogen or sulfur, which can furthermore be substituted by $C_1$–$C_{10}$ alkyl, $C_3$–$C_7$ cycloalkyl, $C_6$ or $C_{10}$ aryl, benzyl, diphenylmethyl, $C_4$–$C_9$ heteroaryl or a heterocyclic residue containing up to 2 heteroatoms selected from the group oxygen, nitrogen or sulfur, or $R^{45}$ and $R^{46}$ together form a 4–7-membered ring, which includes the nitrogen atom to which $R^{45}$ and $R^{46}$ are bonded and which contains up to 2 additional heteroatoms selected from the group oxygen, nitrogen or sulfur and which contains up to 2 double bonds, which can furthermore be substituted by $C_1$–$C_{10}$ alkyl, $C_3$–$C_7$ cycloalkyl, $C_6$ or $C_{10}$ aryl, benzyl, diphenylmethyl, $C_4$–$C_9$ heteroaryl or a 4–9-membered saturated or unsaturated heterocyclic residue containing up to 2 heteroatoms selected from the group oxygen, nitrogen or sulfur, which can be fused with a 3–7 membered homocyclic or heterocyclic, saturated or unsaturated ring, or $R^1$ and $R^2$ or $R^4$ and $R^2$ or $R^6$ and $R^{12}$ together form a 5–6-membered ring, which includes the nitrogen atom to which $R^2$ or $R^6$ and $R^{12}$ can be attached and which contains up to 1 additional heteroatom selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, or which can be fused with a 5–6-membered homocyclic or heterocyclic saturated ring, or $R^1$ and $R^4$ or $R^1$ and $R^5$ or $R^3$ and $R^4$ together form a 5–6-membered ring containing up to 1 heteroatom selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo or fused with a 5–6-membered homocyclic or heterocyclic saturated ring, A represents —C(O)—, —C(O)—C(O)—, —SO—, —$SO_2$—, —PO—, —$PO_2$—, 2-pyrimidyl, 4-pyrimidyl, 2-pyridyl, 2-imidazolyl, 4-imidazolyl, 2-benzimidazolyl or a ring selected from the following group:

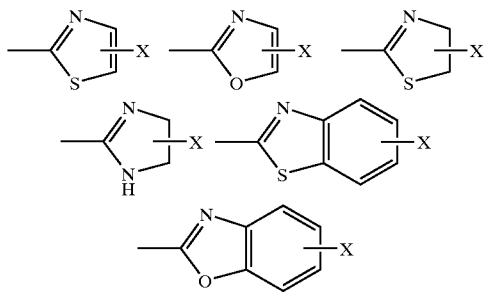

wherein the abovementioned ring systems can optionally be substituted by $C_1$–$C_4$ alkyl, $C_1$–$C_4$ alkyloxy, halogen, nitro, cyano, X represents a bond, oxygen or —$NR^{12}$, wherein $R^{12}$ represents hydrogen, $C_3$–$C_4$ alkyl, $C_2$–$C_4$ alkenyl, $C_2$–$C_4$ alkynyl, which can be optionally substituted by phenyl, or together with $R^6$ form a 4–7-membered ring, which includes the nitrogen atom to which $R^6$ and $R^{12}$ can be attached and which contains up to 2 additional heteroatoms selected from the group oxygen, nitrogen or sulfur and containing up to 2 double bonds, which can optionally be substituted by 1 to 2 substituents selected from the group $C_1$–$C_4$ alkyl, phenyl, benzyl, $C_3$–$C_7$ cycloalkyl, $C_1$–$C_4$ alkyloxy, halogen, nitro, cyano, oxo, Y represents oxygen or sulfur, Z represents —C(O)$OR^{47}$, —C(O)$NR^{48}R^{49}$, —$SO_2NR^{48}R^{49}$, —SO($OR^{47}$), —$SO_2(OR^{47})$, —P(O)$R^{47}(OR^{49})$, —PO($OR^{47}$)($OR^{49}$) or 5-tetrazolyl, wherein $R^{48}$ is —C(O)$R^{50}$ or —$SO_2R^{50}$, wherein $R^{50}$ is, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group halogen, nitro, cyano, $R^{47}$ and $R^{49}$ are identical or different and represent hydrogen, polymeric resin, $C_1$–$C_4$ alkyl, $C_2$–$C_6$ alkenyl, $C_2$–$C_6$ alkynyl, $C_3$–$C_6$ cycloalkyl, $C_6$ or $C_{10}$ aryl, which can optionally be substituted by 1 to 3 substituents selected from the group $C_1$–$C_4$ alkyl, $C_1$–$C_4$ alkyloxy, halogen, nitro, cyano, and pharmaceutically acceptable salts thereof.

In another very preferred embodiment, the invention relates to compounds of general formula (I), wherein $R^1$ and $R^2$ together form a 6-membered ring, which includes the nitrogen atom to which $R^2$ is bonded, $R^3$, $R^4$, $R^5$, $R^7$ and $R^8$ represent hydrogen, $R^6$ represents hydrogen, $C_1$–$C_{10}$ alkyl, $C_3$–$C_6$ cycloalkyl, $C_6$ or $C_{10}$ aryl, which can optionally be substituted by 1 to 3 residues selected from the group methyl, methoxy, halogen, carbonyloxymethyl, trifluoromethyl and which can furthermore be single-foldedly substituted by $C_6$ cycloalkyl, phenyl, pyridyl, pyrrolidyl or benzo-fused, which can optionally be substituted by 1 to 3 residues selected from the group methyl, halogen, oxo, or $R^6$ and $R^{12}$ together form a 6-membered ring, which includes the nitrogen atom to which $R^6$ and $R^{12}$ can be attached and which contains up to 1 additional heteroatom selected from the group oxygen or nitrogen, $R^9$ represents $C_1$ alkyl, which is single-foldedly substituted by $C_6$ aryl, which is single-foldedly substituted by $R^{43}$, wherein $R^{43}$ represents —$NR^{44}$(CO)$NR^{45}R^{46}$, wherein $R^{44}$ represents hydrogen and wherein $R^{45}$ and $R^{46}$ are identical or different and represent hydrogen, $C_1$ alkyl or a 6-membered saturated heterocyclic residue containing 0 or 1 nitrogen, which can furthermore be substituted by benzyl or diphenylmethyl, or $R^{45}$ and $R^{46}$ together form a 6-membered ring, which includes the nitrogen atom to which $R^{45}$ and $R^{46}$ are bonded and which contains up to 1 additional heteroatom selected from the group oxygen or nitrogen, which can furthermore be substituted by $C_1$ alkyl, phenyl, benzyl, diphenylmethyl, or which can be benzofused, A represents —C(O)—, —SO$_2$, -2-pyrimidyl, 4-pyrimidyl, 2-pyridyl or 2-benzimidazolyl, wherein the abovementioned ring systems can optionally be single-foldedly substituted by halogen, X represents a bond, oxygen or —NR$^{12}$, wherein R$^{12}$ represents hydrogen or methyl, or together with R$^6$ forms a 6-membered ring, which includes the nitrogen atom to which R$^6$ and R$^{12}$ can be attached and which contains up to 1 additional heteroatom selected from the group oxygen or nitrogen, Y represents oxygen, Z represents —C(O)OR$^{47}$, wherein R$^{47}$ represents hydrogen or polymeric resin, and pharmaceutically acceptable salts thereof.

In a very particularly preferred embodiment, the invention relates to the specific compounds as described in the specification under "examples".

In the context of the present invention alkyl stands for a straight-chain or branched alkyl residue, such as methyl, ethyl, n-propyl, iso-propyl, n-pentyl. If not stated otherwise, preferred is C$_1$–C$_{10}$ alkyl, very preferred is C$_1$–C$_6$ alkyl.

Alkenyl and alkinyl stand for straight-chain or branched residues containing one or more double or triple bonds, e.g. vinyl, alkyl, isopropinyl, ethinyl. If not stated otherwise, preferred is C$_1$–C$_{10}$ alkenyl or alkinyl, very preferred is C$_1$–C$_6$ alkenyl or alkinyl.

Cycloalkyl stands for a cyclic alkyl group such as cyclopropyl, cyclobutyl, cyclopentyl, cyclohexyl or cycloheptyl. Preferred is C$_3$–C$_7$ cycloalkyl.

Halogen in the context of the present invention stands for fluorine, chlorine, bromine or iodine. If not specified otherwise, chlorine or fluorine are preferred.

If not further specified, 4–9-membered saturated or unsaturated heterocyclic residue in the context of the present invention represents heteroatom-containing not aromatic, saturated or unsaturated rings containing 1 to 4 heteroatoms selected from O, S and N. Examples for not aromatic rings are: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin-3-yl, 1,2-dihydropyridin-1-yl, 1,4-dihydropyridin-1-yl, piperazin-1-yl, morpholin-1-yl, azepin-1-yl, 1,4-diazepin-1-yl. Examples for aromatic rings are: pyridyl, furyl, thienyl, pyrrolyl, imidazolyl, pyrazolyl, pyrazinyl, pyrimidinyl, pyridazinyl, indolicenyl, indolyl, benzo[b]thienyl, benzo[b]furyl, indazolyl, chinolyl, isochinolyl, naphthyridinyl, chinazolinyl.

If not specified otherwise, ring systems as substituents can be attached to their respective place of attachment via any ring atom, that is any carbon or nitrogen atom.

If not specified otherwise, in the context of the present invention heteroatom stands preferably for O, S, N or P.

Annulated or fused describes 1,1- or 1,2-fused ring systems, e.g. spiro systems or systems with a [0]-bridge. Benzo-fused describes a [0]-bridge, wherein one of the rings is aromatic.

The polymeric resin for solid phase is preferably a polystyrene resin and in particular a commercially available Wang polystyrene resin.

Surprisingly, the compounds of the present invention show good integrin antagonistic activity. They are therefore suitable especially as $\alpha_4\beta_1$ and/or $\alpha_4\beta_7$ and/or $\alpha_9\beta_1$ integrin antagonists and in particular for the production of pharmaceutical compositions for the inhibiton or the prevention of cell adhesion and cell-adhesion mediated disorders. Examples are the treatment and the prophylaxis of arteriosclerosis, asthma, allergies, diabetes, inflammatory bowel disease, multiple sclerosis, myocardial ischemia, rheumatoid arthritis, transplant rejection and other inflammatory, autoimmune and immune disorders.

The integrin antagonists of the invention are usefull not only for treatment of the physiological conditions discussed above, but are also useful in such activities as purification of integrins and testing for activity.

For the treatment of the abovementioned diseases, the compounds according to the invention can exhibit non-systemic or systemic activity, wherein the latter is preferred. To obtain systemic activity the active compounds can be administered, among other things, orally or parenterally, wherein oral administration is preferred.

For parenteral administration, forms of administration to the mucous membranes (i.e. buccal, lingual, sublingual, rectal, nasal, pulmonary, conjunctival or intravaginal) or into the interior of the body are particularly suitable. Administration can be carried out by avoiding absorption (i.e. intracardiac, intra-arterial, intravenous, intraspinal or intralumbar administration) or by including absorption (i.e. intracutaneous, subcutaneous, percutaneous, intramuscular or intraperitoneal administration).

For the above purpose the active compounds can be administered per se or in administration forms.

Suitable administration forms for oral administration are, inter alia, normal and enteric-coated tablets, capsules, coated tablets, pills, granules, pellets, powders, solid and liquid aerosols, syrups, emulsions, suspensions and solutions. Suitable administration forms for parenteral administration are injection and infusion solutions.

The active compound can be present in the administration forms in concentrations of from 0–100% by weight; preferably the concentration of the active compound should be 0.5–90% by weight, i.e. quantities which are sufficient to allow the specified range of dosage.

The active compounds can be converted in the known manner into the abovementioned administration forms using inert non-toxic pharmaceutically suitable auxiliaries, such as for example excipients, solvents, vehicles, emulsifiers and/or dispersants.

The following auxiliaries can be mentioned as examples: water, solid excipients such as ground natural or synthetic minerals (e.g. talcum or silicates), sugar (e.g. lactose), non-toxic organic solvents such as paraffins, vegetable oils (e.g. sesame oil), alcohols (e.g. ethanol, glycerol), glycols (e.g. polyethylene glycol), emulsifying agents, dispersants (e.g. polyvinylpyrrolidone) and lubricants (e.g. magnesium sulphate).

In the case of oral administration tablets can of course also contain additives such as sodium citrate as well as additives such as starch, gelatin and the like. Flavour enhancers or colorants can also be added to aqueous preparations for oral administration.

For the obtainment of effective results in the case of parenteral administration it has generally proven advantageous to administer quantities of about 0.001 to 100 mg/kg, preferably about 0.01 to 1 mg/kg of body weight. In the case of oral administration the quantity is about 0.01 to 100 mg/kg, preferably about 0.1 to 10 mg/kg of body weight.

It may nevertheless be necessary to use quantities other than those mentioned above, depending on the body weight concerned, the method of administration, the individual response to the active compound, the type of preparation and the time or interval of administration.

Suitable pharmaceutically acceptable salts of the compounds of the present invention that contain an acidic moiety include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

Suitable pharmaceutically acceptable salts of the compounds of the present invention that contain a basic moiety include addition salts formed with organic or inorganic acids. The salt forming ion derived from such acids can be halide ions or ions of natural or unnatural carboxylic or sulfonic acids, of which a number are known for this purpose. Examples include chlorides, acetates, tartrates, or salts derived from amino acids like glycine or the like. The physiologically acceptable salts such as the chloride salts and the amino acid salts can be used medicinally as described below and are preferred.

These and other salts which are not necessarily physiologically acceptable are useful in isolating or purifying a product acceptable for the purposes described below.

The salts are produced by reacting the acid form of the invention compound with an equivalent of the base supplying the desired basic ion or the basic form of the invention compound with an equivalent of the acid supplying the desired acid ion in a medium in which the salt precipitates or in aqueous medium and then lyophilizing. The free acid or basic form of the invention compounds can be obtained from the salt by conventional neutralization techniques, e.g., with potassium bisulfate, hydrochloric acid, sodium hydroxide, sodium bicarbonate, etc.

The compounds according to the invention can form non covalent addition compounds such as adducts or inclusion compounds like hydrates or clathrates. This is known to the artisan and such compounds are also object of the present invention.

The compounds according to the invention can exist in different stereoisomeric forms, which relate to each other in an enantiomeric way (image and mirror image) or in a diastereomeric way (image different from mirror image). The invention relates to the enantiomers and the diastereomers as well as their mixtures. They can be separated according to customary methods.

The compounds according to the invention can exist in tautomeric forms. This is known to the artisan and such compounds are also object of the present invention. The synthesis of the compounds according to the invention (I) can be illustrated by the following scheme 1:

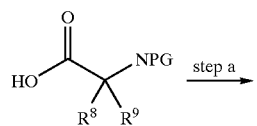

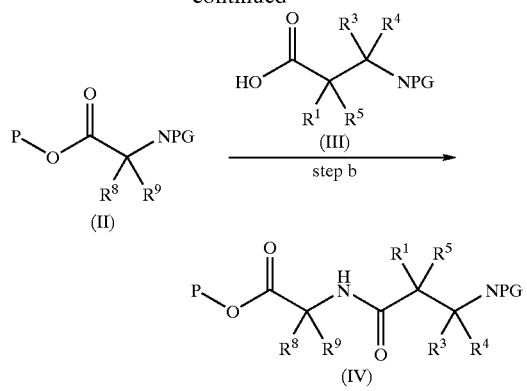

Starting from α-amino acid derivatives (II), the precursor is first immobilized on a resin or esterified (step a), followed by amide coupling (step b) and further derivatized as described below.

In the above scheme, PG stands for an amino protecting group that is stable under the respective reaction conditions such as 9-fluorenylmethyloxycarbonyl (Fmoc) or tert.-butyloxycarbonyl (Boc) or phtalimid. These are known to the one skilled in the art and are in detail described in Greene, T., Protective Groups in Organic Synthesis, 2$^{nd}$ ed., John Wiley, N.Y., 1991.

According to an embodiment, starting materials used in the process according to the invention for the preparation of compounds of the general formula (I) are the following carboxylic acid derivatives (II):

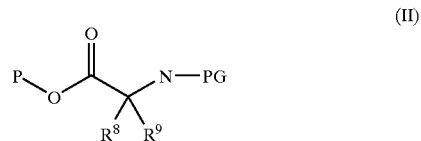

Compounds of general formula (II) are commercially available, known or can be prepared by customary methods starting from known α-amino acids or precursors for customary α-amino acid synthesis. For the preparation process according to the invention, the carboxyl group is in this case blocked by a conventional protective group P. Protective groups of this type are known to the person skilled in the art and are in detail described in Greene, T., Protective Groups in Organic Synthesis, 2$^{nd}$ ed., John Wiley, N.Y., 1991. The carboxyl group is particularly preferably esterified, P being a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof. Particularly preferably, however, the preparation process according to the invention for the compounds of the general formula (I) is carried out on a solid phase in order to achieve a process implementation which is as economical as possible. In this case, the carboxyl residue can be bonded to any solid phase conventionally used for reactions of this type. According to the invention, the solid phase used is particularly preferably a polystyrene resin and in particular a commercially available Wang polystyrene resin. In the α-position to the carboxyl group, these carboxylic acid derivatives can have substituents such as described under $R^8$ and $R^9$, for example, hydrogen, a $C_1$–$C_{10}$-alkyl such as, for example, methyl, ethyl, propyl, isopropyl, butyl, isobutyl, t-butyl, pentyl, isopentyl, neopentyl, hexyl, heptyl, octyl, nonyl, decyl, a $C_3$–$C_7$-cycloalkyl such as, for example, cyclopropyl, cyclobutyl, cyclopentyl, cyclohexyl, cycloheptyl an aryl such as, for example, phenyl, benzyl, tolyl or a substituted derivative thereof, an optionally substituted alkenyl residue, or an optionally substituted alkinyl residue. The alkyl alkenyl and cycloalkyl residues and the benzyl residue can be introduced by reaction of the ester of the starting compounds with the appropriate alkyl, alkenyl, cycloalkyl or benzyl halides in basic medium, if the corresponding derivatives are not commercially available. The alkinyl residue can be introduced, for example, by reaction of the bromo ester of the present starting compound with an appropriate acetylide anion. In the case of the phenyl residue the starting materials used are preferably the corresponding α-phenyl-α-aminocarboxylic acid derivatives and, if necessary, the other substituents at the α-C atom to the terminal carboxyl group are introduced via the appropriate alkyl halide.

The above reactions and their implementation are well known to the person skilled in the art and are described in detail in standard textbooks such as, for example, Houben-Weyl, Methoden der organischen Chemie [Methods of Organic Chemistry], Georg Thieme Verlag, Stuttgart.

If the substituents themself should be substituted, e.g by R', appropriate reactive groups should be present in the substituent to allow further functionalization. These reactive groups should be inert to the reaction conditions of the previous step. For this purpose, the substituent can also be unsaturated to allow further functionalization such as palladium catalyzed C—C-coupling reactions (e.g. Heck-reaction or Sonogashira-reaction), eventually followed by hydration (scheme 2):

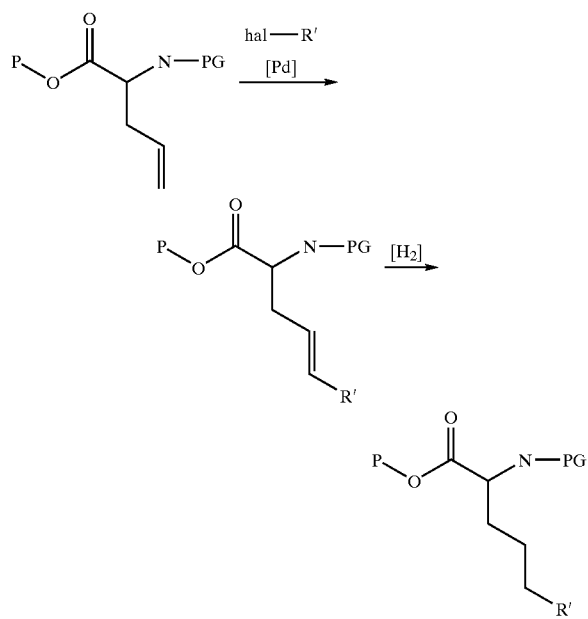

In the abovementioned scheme, hal stands for a leaving group such as a halogen, tosyl, mesyl or triflate, [Pd] stands for a Palladium(0) or Palladium(II) moiety.

If the substituent $R^8$ or $R^9$ in the α-position to the carboxylic group carry an appropriate substituted aryl or heteroaryl unit, another method for insertion of an additional substituent are the C—C-coupling reactions according to the following scheme 3:

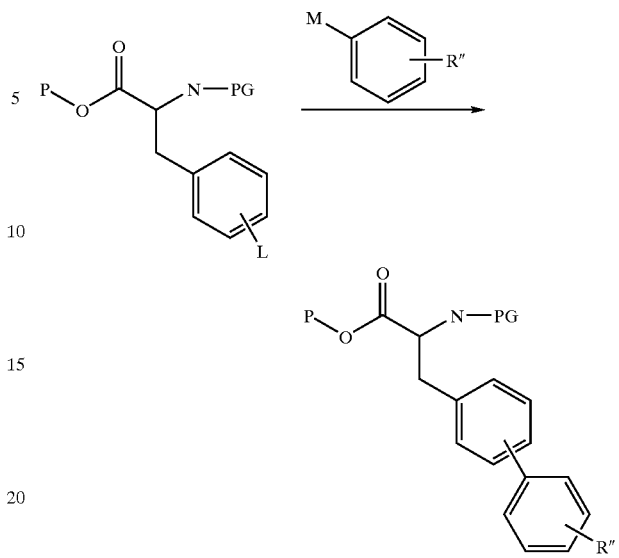

The starting compounds to be employed according to the above embodiment have a terminal aryl or heteroaryl unit which must carry at least one substituent L. This substituent L must be substitutable by another aryl or heteroaryl group by means of one of the known aryl-aryl coupling procedures. According to the present invention, L can be —H, —F, —Cl, —Br, —I, —SCN, —$N_2^+$ or an organometallic residue. Preferred organometallic residues which may be mentioned are, for example, a magnesium, copper, boron, tin, lithium or lithium cuprate residue.

If the corresponding starting compounds are not commercially available, the terminal aryl or heteroaryl unit can be connected to the appropriate carboxylic acid derivative by standard processes such as, for example, a Friedel-Crafts alkylation, Friedel-Crafts acylation or by organometallic synthesis procedures such as, for example, a palladium-assisted coupling, after which, if appropriate, further derivatization steps follow which are known to the person skilled in the art and described in detail in standard textbooks such as, for example, Houben-Weyl, Methoden der organischen Chemie [Methods of Organic Chemistry], Georg Thieme Verlag, Stuttgart.

In preferred embodiments according to the invention, the biphenyl nucleus is generated by means of an aryl-aryl coupling. Formally, in this case the residue L at the terminal aryl or heteroaryl group of the carboxylic acid derivative serving as a starting compound is replaced by a aryl or heteroaryl compound of the following formula:

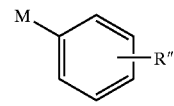

Possible coupling reactions are, for example, the reaction of two unsubstituted phenyl groups (i.e. L and M are hydrogen) in the presence of $AlCl_3$ and an acid (Scholl reaction), the coupling of the two phenyl iodides in the presence of copper (Ullmann reaction), the reaction of the unsubstituted carboxylic acid derivative with a phenyldiazonium compound under basic conditions (Gomberg-Bachmann reaction) or coupling with participation of organometallic reagents. In this connection, the coupling of two phenyl Grignard compounds in the presence of thallium bromide, the coupling of two organoboron compounds in the presence of silver nitrate and sodium hydroxide, the reaction of a diphenyllithium cuprate in the presence of oxygen and palladium-assisted couplings of a phenyl halide with an organometallic phenyl compound deserve mention. The implementation of these reactions is described in detail in standard textbooks such as Houben-Weyl, Methoden der organischen Chemie [Methods of Organic Chemistry], Georg Thieme Verlag, Stuttgart. The choice of the coupling reaction depends on the presence of possibly interfering or sensitive substituents in the reactants. For the preferred compounds according to the invention, however, it has proven particularly advantageous to generate the biphenyl nucleus by coupling of a phenyl halide with an organometallic phenyl compound in the presence of a palladium compound, for example a Pd(0), a Pd(II) or a Pd(IV) compound, and of a phosphane such as triphenylphosphane.

The phenyl halide used in this case can be the corresponding phenyl fluoride, chloride, bromide or iodide, the corresponding bromide being particularly preferred. The organometallic phenyl compound used is preferably a substance in which a metallic element such as, for example, zinc, magnesium, boron, lithium, copper, tin or another element conventionally used for this purpose is bonded directly to the aryl ring. According to the invention, organoboron compounds are particularly preferred.

Further substituents can be bonded to the aryl ring additionally to the residue R" and the metallic element.

According to a preferred embodiment of the present invention, the synthesis of the compounds according to the invention is carried out on a solid phase such as a polystyrene resin, particularly preferably a commercially available Wang polystyrene resin (step a). In this case, the resin is first swollen in a solvent such as dimethylformamide (DMF). The carboxylic acid serving as a starting compound is then bonded to the resin by standard procedures. For example, the bonding of the carboxylic acid to the resin can be carried out in the presence of a base such as pyridine and a reagent activating the carboxyl unit, such as an acid halide, for example dichlorobenzoyl chloride, in a solvent such as dimethylformamide (DMF). However, other reagents conventionally used for this purpose can also be employed. The reaction mixture is stirred at room temperature and normal pressure for at least 2 hours, preferably 12 hours, particularly preferably approximately 24 hours, the carboxylic acid being employed in an excess, preferably in a two- to three-fold excess, with respect to the loading of the solid phase.

The aryl-aryl coupling is preferably carried out according to the invention by treating the carboxylic acid bonded to the solid phase, in aqueous medium in the presence of a base such as sodium carbonate with the appropriate aryl coupling reagent of the formula (3) and a catalyst conventionally used for this purpose, for example a palladium(II) salt, preferably bis-(triphenylphosphane)-palladium(II) chloride in combination with triphenylphosphane. An approximately 3- to 8-fold, preferably an approximately 4 to 6-fold, excess of the aryl coupling agent and catalytically active amounts of the palladium compound, for example approximately 10 times lower than the amount of the carboxylic acid, is preferably employed in this case and, after stirring briefly at room temperature, for example for 5 to 10 minutes, the reaction mixture is heated for approximately 2–24 hours, preferably 6–24 hours and particularly preferably 12–24 hours, to a temperature in the range from 40 to 110° C., preferably 50 to 100° C. and particularly preferably 60 to 90° C. The biphenyl compound obtained can immediately be reacted further without purification after unreacted reactants which may be present are removed by washing with an acidic solution, for example a hydrochloric acid solution.

The functionalization of the α-amino acid moiety as described above can also take place after the formation of the amide bond. Preferred, however, is functionalization before formation of the amide bond.

According to the invention the amide coupling (step b) is carried out with carboxylic acid of general formula (III), which are commercially available, known or can be prepared by customary methods starting from known β-amino acids or precursors for customary β-amino acid synthesis.

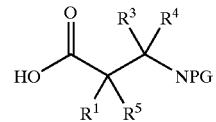

(III)

For the introduction of a substituent into the β-position relative to the carboxyl group, the possibility that suggests itself, for example, is to start from the corresponding α,β-unsaturated carboxylic acid derivatives and to react these with the respective alkyl or cycloalkyl cuprates in the sense of a Michael addition. β-substituted derivatives are also accessible via the condensation of a derivative of malonic acid with an aldehyde or a keton or by $C_1$ chain elongation by Arndt-Eistert reaction. Subsequently, if desired, another substituent can be introduced into the α-position relative to the carboxyl group. These substituents in α-position can be introduced essentially according to the same methods as described for the compounds of formula (II), with the exception that β-amino acid derivatives are used instead of α-amino acids.

These reactions and their implementation are also well clown to the person skilled in the art and are described in detail in standard textbooks such as, for example, Houben-Weyl, Methoden der organischen Chemie [Methods of Organic Chemistry], Georg Thieme Verlag, Stuttgart.

In one preferred embodiment, introduction of a substituent into the β-position relative to the carboxyl group takes place before introduction of a substituent into the α-position relative to the carboxyl group.

The α-amino acids used according to the invention are commercially available, for example, from Novabiochem or Bachem. The β-amino acids can in some cases likewise be obtained from these companies or can be prepared according to the procedures of T. B. Johnson, Journal of the American Chemical Society, 1936, 58, or of V. A. Soloshonok, Tetrahedron Assymetry, 1995, 1601. These amino acids can be converted into the desired carboxyl-protected amino acid derivative, for example, by protection of the amino group, optionally subsequent protection of the carboxylic acid unit and subsequent deprotection of the amino group. Protective groups which can be used in this case for the amino group are all groups known for this purpose. According to the invention, the use of a 9-fluorenylmethoxycarbonyl group (FMOC) as a protective group for the amino unit is particularly preferred. The carboxylic acid group is optionally protected or derivatized as described above.

For the preparation of precursors (IV) (Step b), (II) is deprotected and coupled with (III) in an amide formation reaction. The reaction conditions and coupling agents as well as the deprotection conditions are well known to the one skilled in the art and described in Y. Angell et al. *Tetrahedron Letters*, 35, 1994, 5981–4.

According to a preffered embodiment, to a solution of β-amino acid derivatives of general formula (III) in dimethylformamide O-(7-azabenzotriazol-1-yl)1,1,3,3-tetramethyluronium hexafluorophosphate and diisopropylethylamin were added. After shaking the mixture for about 15 minutes, the deprotected compounds of general formula (II) (optionally immobilized on resin) were treated with this solution for about 4 hours at medium temperature, e.g. room temperature. The workup follows standard procedure known to the person skilled in the art, e.g. the derivatized resin (IV) is washed with dimethylformamide and tetrahydrofurane.

The deprotected amino function of compounds (IV) can be functionalized by a variety of acceptor substituents (step d) such as carbonyl-, aminocarbonyl-, oxycarbonyl-, sulfonyl-, oxalyl-, pyrimidyl- and pyridyl-derivatives.

This formation of the respective e.g. amide-, urea-, carbamate-, sulfonamide-moieties is known to the person skilled in the art and in detail described in Houben-Weyl, Methoden der organischen Chemie [Methods of Organic Chemistry], Georg Thieme Verlag, Stuttgart.

For example, formation of the amides can take place using the respecive acid chloride or acid with a coupling agent such as DCC (Dicyclohexylcarbodiimid) or HOBT (N-Hydroxybenzotriazole) formation of the ureas can take place using the respective isocyanates, carbamates are formed using chloroformates and sulfonamides are formed using sulfonylchlorides.

For this purpose the compound (IV) is deprotected with a base, e.g. piperidine solution in dimethylformamide and shaken at room temperature for about 10 minutes and worked up. In case solid phase synthesis is used, the resin is then washed with dimethylformamide and further base solution in dimethylformamide is added. After shaking for about 20 minutes, it is washed, e.g. with dimethylformamide and tetrahydrofurane.

For example, the deprotected compound (IV) is then treated with a solution of base, e.g. diisopropylethylamine in tetrahydrofurane and a solution of acylating/sulfonylating/carbamoylating reagent, e.g. acid chloride, sulfonyl chloride or chloroformate in tetrahydrofurane. It is shaken overnight at room temperature. The derivatized compound (Va) is then worked up following standard procedure, e.g. in case solid phase synthesis is used, the resin is washed with dimethylformamide, methanol, tetrahydrofurane and dichloromethane.

In another embodiment, the deprotected compound (IV) is treated with a solution of base, e.g. diisopropylethylamine in dimethylformamide and a solution of halogen-heterocycle reagent in dimethylformamide. It is shaken for about 5–16 hours at room or elevated temperature. The derivatized compound (Vb or Vc) is then worked up according to standard procedure, e.g. in case of solid phase synthesis washed with dimethylformamide.

In case the halogen-heterocycle reagent bears further functionalizable substituents, e.g. halogen, these positions can be derivatized subsequently (step e). For example, an amine reagent in dimethylformamide is added to the derivatized compound (Vb) and the mixture is shaken overnight at room or elevated temperature. The derivatized compound is then worked up according to standard procedure, e.g. in case of solid phase synthesis washed with dimethylformamide, tetrahydrofurane, dichloromethane.

The ester derivatives according to the invention can be converted into the corresponding free carboxylic acids in a conventional manner, such as, for example, by basic ester hydrolysis (step f).

In a preferred embodiment, the immobilized compounds are subsequently released from the resin by treatment with appropriate cleavage agents, such as strong acids like trifluoroacetic acid in dichloromethane.

EXAMPLES

In the examples below, all quantitative data, if not stated otherwise, relate to percentages by weight For synthetic process the compounds are immobilized on solid phase. A preferred polymeric resin for this purpose is Wang polystyrene resin (Rapp-Polymere, Tübingen). As known to the one skilled in the art, the compounds can also be prepared by liquid synthetic methods using essentially the same reagents. In this case Wang polystyrene resin is substituted by an protection group for carboxyl groups such as esters.

All retention times are indicated in minutes and, if not stated otherwise, were determined by high-performance liquid chromatography (HPLC) on an RP column (Eurospher 100, C18, ID 4 mm) by means of UV absorption at 214 nm. An acetonitrile/water mixture with 0.1% trifluoroacidic acid was used as eluent with following method: 0 min.=10% acteonitrile, 13 min.=80% acteonitrile, 15 min.= 80% acetonitrile, 17 min.=10% acteonitrile.

The mass determinations were carried out by high-performance liquid chromatography (HPLC-MS), if not stated otherwise, using the electron spray ionization (EST) method.

Example 1

General synthesis scheme:

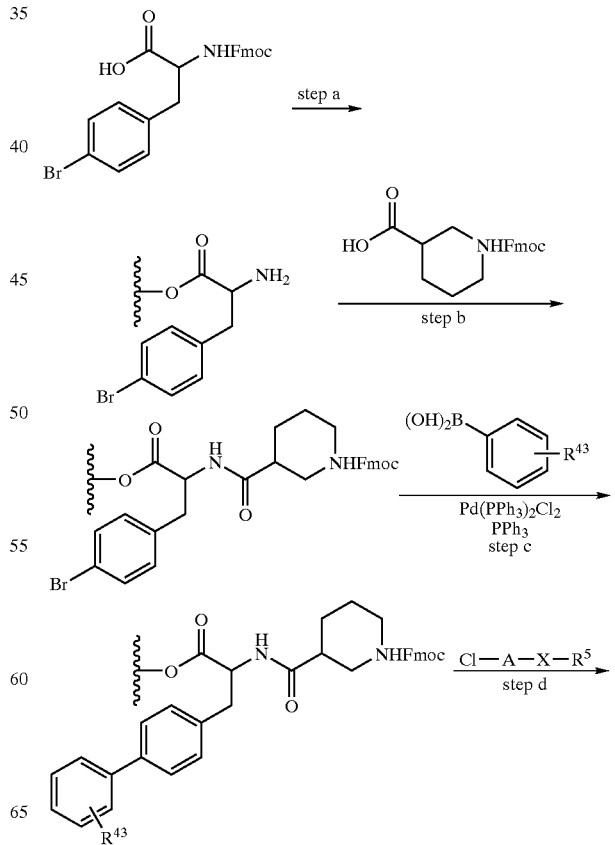

-continued

Example 1.1

(2S)-3-(2',5'-dichloro[1,1'-biphenyl]-4-yl)-2-({[1-(2-methoxybenzoyl)-3-piperidinyl]carbonyl}amino) propanoic acid

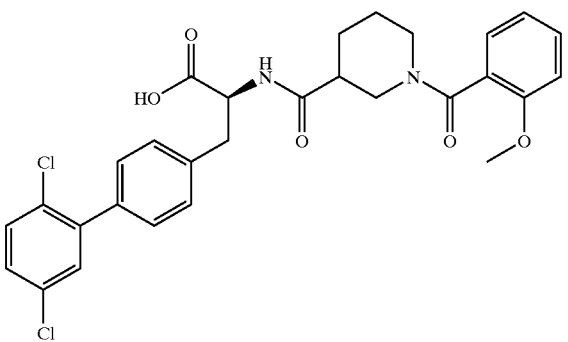

Step a 1.2 g of Wang polystyrene resin (Rapp-Polymere, Tübingen; loading 0.96 mmol/g) are swollen in dimethylformamide. The solvent is filtered off with suction and a solution of 957 mg of (2S)-3-(4-bromophenyl)-2-(9-fluorenylmethoxycarbonylamino)-propionic acid in 8 ml dimethylformamide is added. After shaking at room temperature for 15 minutes, the suspension is treated with 304 μl of pyridine and 478 mg of 2,6-dichlorobenzoyl chloride. It is shaken overnight at room temperature. The derivatized resin is then washed with dimethylformamide, methanol and dichloromethane. The resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane.

Step b

To a solution of 1.188 g of (3R,S)-N-(9-Fluorenylmethoxycarbonyl)-piperidin-3-carboxylic acid (amino acid reagent) in 7 ml dimethylformamide 1.331 g O-(7-azabenzotriazol-1-yl)1,1,3,3-tetramethyluronium hexafluorophosphate and 616 μl diisopropylethylamine were added. After shaking the mixture for 15 minutes, the derivatized resin was treated with this solution for 4 hours at room temperature. The derivatized resin is then washed with dimethylformamide and tetrahydrofurane.

Step c

The derivatized resin is suspended in 7 ml of xylene, treated with 1.414 g of 2,5-dichlorobenzeneboronic acid (boronic acid reagent) and a solution of 1.571 g sodium carbonate in 7 ml of water and shaken for 5 minutes at room temperature. 217 mg of bis-(triphenylphosphane)-palladium (II) chloride and 162 mg of triphenylphosphane are then added and the mixture is stirred overnight at 85° C. The resin is then washed with tetrahydrofurane/water 1:1, 0.25 M aqueous hydrochloric acid, water, dimethylformamide, methanol, tetrahydrofurane and dichloromethane.

Step d

The derivatized resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane. The derivatized resin is treated with a solution of 1.6 ml of diisopropylethylamine in 12 ml tetrahydrofurane and a solution of 1.361 g of 2-methoxybenzoylchloride (acylating/sulfonylating/carbamoylating reagent) in 12 ml tetrahydrofurane. It is shaken overnight at room temperature. The derivatized resin is then washed with dimethylformamide, methanol, tetrahydrofurane and dichloromethane.

Step f

For removal of the product, the derivatized resin is shaken with 10 ml of trifluoroacetic acid/dichloromethane 1:1 for 1 hour, filtered off. The filtrate is concentrated in vacuo. 98 mg of the title compound are obtained.

Mass spectrometry (ESI): 556.
Retention time (HPLC): 9.9+10.4.

Example 1.2

(2S)-2-({[1-(2-chlorobenzoyl)-3-piperidinyl] carbonyl}amino)-3-(4'-methyl[1,1'-biphenyl]-4-yl) propanoic acid

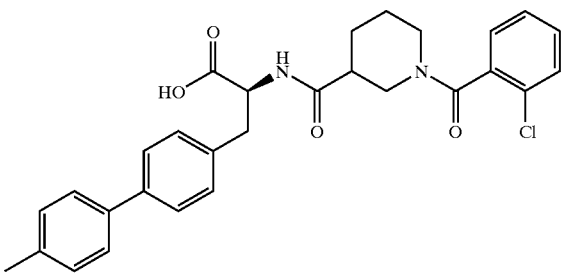

(2S)-3-(4'-Methyl-biphenyl-4-yl)-2-[(2-chloro-phenylcarbonyl)-(3R,S)-piperidin-3-yl-carbonylamino]-propionic acid is prepared according to the procedure of example 1.1, with the exception that 4-methyl-benzeneboronic acid is used as boronic acid reagent instead of 2,5-dichlorobenzeneboronic acid and 2-chlorobenzoylchloride is used as acylating reagent instead of 2-methoxybenzoylchloride.

Mass spectrometry (ESI): 506.
Retention time (HPLC): 9.8+10.3.

Example 1.3

(2S)-2-[({1-[(2,6-dichlorophenyl)sulfonyl]-3-piperidinyl}carbonyl)amino]-3-(2'-methyl[1,1'-biphenyl]-4-yl)propanoic acid

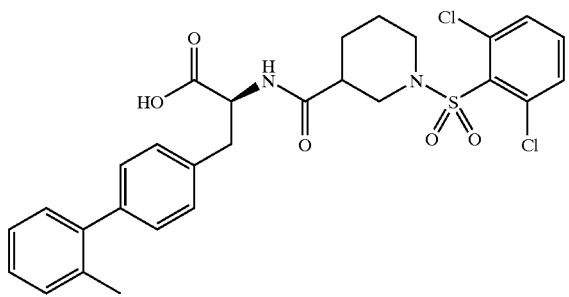

(2S)-3-(2'-Methyl-biphenyl-4-yl)-2-[(2,6-dichlorophenylsulfonyl)-(3R,S)-piperidin-3-yl-carbonylamino]-propionic acid is prepared according to the procedure of example 1.1, with the exception that 2-methylbenzeneboronic acid is used as boronic acid reagent instead of 2,5-dichlorobenzeneboronic acid and 2,6-dichlorobenzenesulfonylchloride is used as acylating reagent instead of 2-methoxybenzoylchloride.

Mass spectrometry (ESI): 576.

Retention time (HPLC): 11.9+12.2.

$^1$H-NMR (400 MHz, CDCl$_3$) (diastereomer A=H; diastereomer B=H') δ=7.47–7.13 (m, 11H+11H', aryl-H+aryl-H'), 6.55 (d, 1H, NH), 6.32 (d, 1H', NH), 4.95 (dd, 1H, H-2), 4.89 (dd, 1H', H'-2), 3.92–3.75 (m, 2H+2H', NC-Ha+NC-H'a+NC-Hb+NC-H'b), 3.33 (dd, 1H, H-3a), 3.30 (dd, 1H', H'-3a), 3.13 (dd, 1H, H-3b), 3.10 (m, 1H, COC—H), 3.05 (dd, 1H', H'-3b), 2.93 (m, 1H+2H', COC-H'+NC-Hc+NC-H'c), 2.52 (m, 1H+1H', NC-Hd+NC-H'd), 2.24 (s, 3H, aryl-CH$_3$), 2.21 (s, 3H', aryl-CH$_3$), 1.95–1.57 (m, 4H+4H', 2×CH$_2$+2×CH'$_2$).

Example 1.4

(2S)-2-({[1-(2-chlorobenzoyl)-3-piperidinyl]carbonyl}amino)-3-(2',4'-dichloro[1,1'-biphenyl]-4-yl)propanoic acid

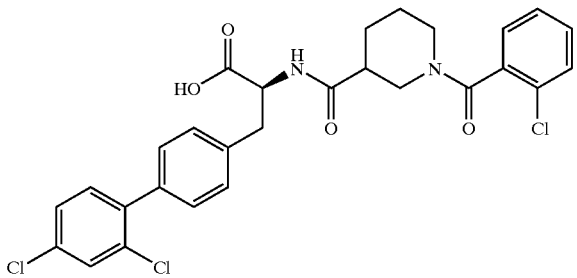

(2S)-3-(2',4'-Dichloro-biphenyl-4-yl)-2-[(2-chlorophenylcarbonyl)-(3R,S)-piperidin-3-yl-carbonylamino]-propionic acid is prepared according to the procedure of example 1.1, with the exception that 2,4-dichlorobenzeneboronic acid is used as boronic acid reagent instead of 2,5-dichlorobenzeneboronic acid and 2-chlorobenzoylchloride is used as acylating reagent instead of 2-methoxybenzoylchloride.

Mass spectrometry (ESI): 560.

Retention time (HPLC): 11.6+12.3.

Example 1.5

(2S)-2-[({1-[(cyclopentyloxy)carbonyl]-3-piperidinyl}carbonyl)amino]-3-(2',5'-dichloro[1,1'-biphenyl]-4-yl)propanoic acid

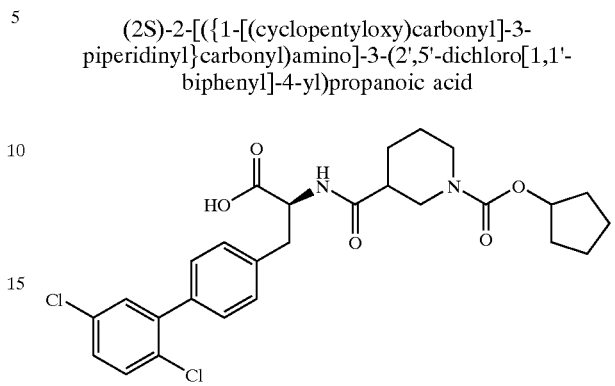

(2S)-3-(2',5'-Dichloro-biphenyl-4-yl)-2-[(cyclopentyloxycarbonyl)-(3R,S)-piperidin-3-yl-carbonylamino]-propionic acid is prepared according to the procedure of example 1.1, with the exception that cyclopentyl chloroformate is used as acylating reagent instead of 2-methoxybenzoylchloride.

Mass spectrometry (ESI): 534.

Retention time (HPLC): 11.4+11.8.

$^1$H-NMR (400 MHz, CDCl$_3$) (diastereomer A=H, diastereomer B=H') δ=7.40–7.15 (m, 7H+7H', aryl-H+aryl-H'), 5.10 (m, 1H+1H', O—CH+O—CH'), 4.91 (dd, 1H, H-2), 4.86 (dd, 1H', H'-2), 4.08 (m, 1H+1H', NCHa+NCH'a), 3.96 (m, 1H+1H', NCHb+NCH'b), 3.34 (dd, 1H, H-3a), 3.26 (dd, 1H', H'-3a), 3.13 (dd, 1H, H-3b), 3.08 (m, 1H', H'-3b), 2.73 (m, 2H+2H', NCHc+NCHd+NCH'c+NCH'd), 2.45 (m, 1H, COCH), 2.33 (m, 1H', COCH'), 1.91–1.55 (m, 12H+12H', 6×CH$_2$+6×CH'$_2$).

Example 1.6

(2S-2-({[1-(benzylsulfonyl)-3-piperidinyl]carbonyl}amino)-3-(2',5'dichloro[1,1'-biphenyl]-4-yl)propanoic acid

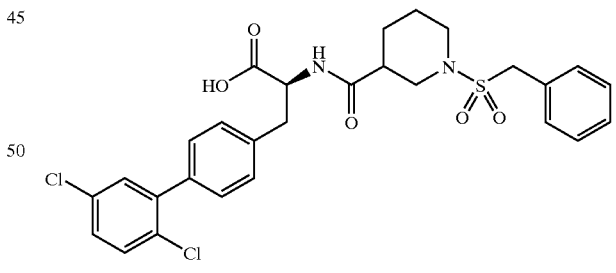

(2S)-3-(2',5'-Dichloro-biphenyl-4-yl)-2-[(benylsulfonyl)-(3R,S)-piperidin-3-yl-carbonylamino]-propionic acid is prepared according to the procedure of example 1.1, with the exception that benzylsulfonylchloride is used as acylating reagent instead of 2-methoxybenzoylchloride.

Mass spectrometry (ESI): 576.

Retention time (HPLC): 9.2+9.6.

According to the procedure of example 1.1 following compounds shown in table 1 were prepared with the exception that optionally different boronic acids were used as boronic acid reagent instead of 2,5-dichlorobenzeneboronic acid and optionally different acid chlorides were used as acylating reagent instead of 2-methoxybenzoylchloride.

According to the procedure of example 1.1 the following compounds shown in table 1 were prepared with the exception that optionally different boronic acids were used as boronic acid reagent instead of 2,5-dichlorobenzeneboronic acid and optionally different sulfonylchlorides were used as sulfonylating reagent instead of 2-methoxybenzoylchloride.

TABLE 1

| structure | MW | MS-ESI | Rt (HPLC) [min] | example |
|---|---|---|---|---|
| 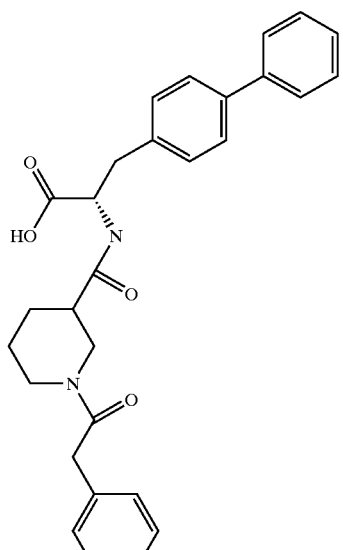 | 470.57 | 471 | 10.2 + 10.5 | 1.7 |
| 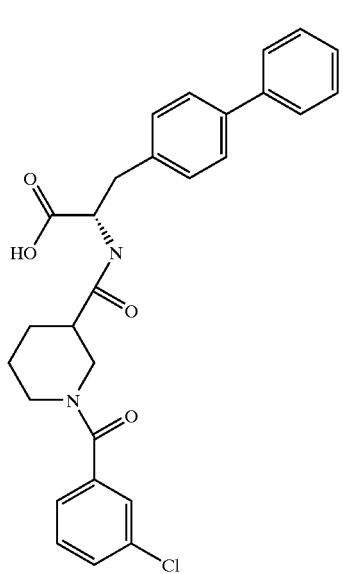 | 490.98 | 491 | 10.5 + 10.9 | 1.8 |

TABLE 1-continued
| structure | MW | MS-ESI | Rt (HPLC) [min] | example |
|---|---|---|---|---|
| 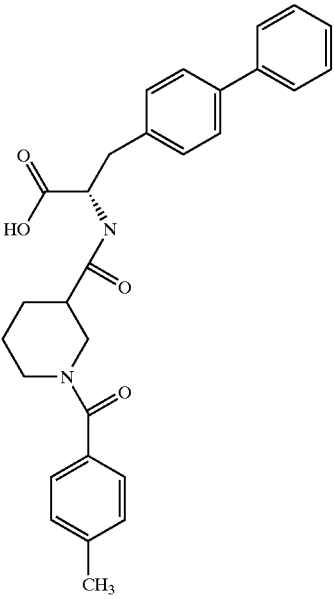 | 470.57 | 470 | 10.3 + 10.7 | 1.9 |
| 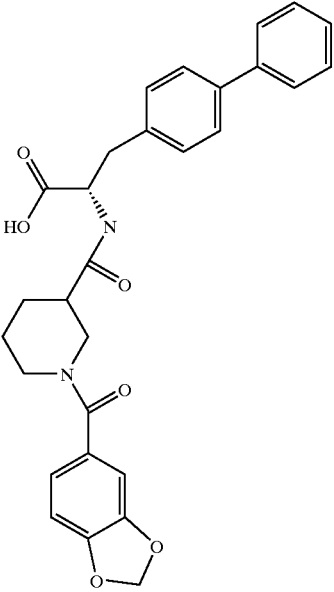 | 500.55 | 501 | 9.5 + 10.1 | 1.10 |

TABLE 1-continued

| structure | MW | MS-ESI | Rt (HPLC) [min] | example |
|---|---|---|---|---|
| 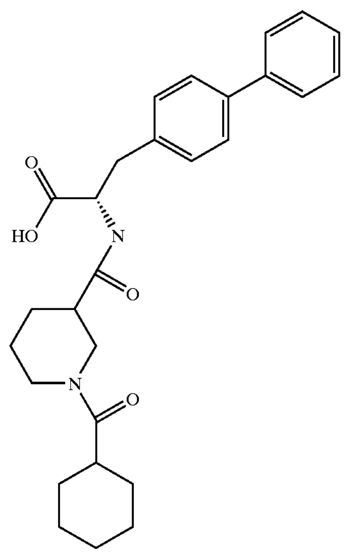 | 462.59 | 463 | 10.9 + 11.1 | 1.11 |
| 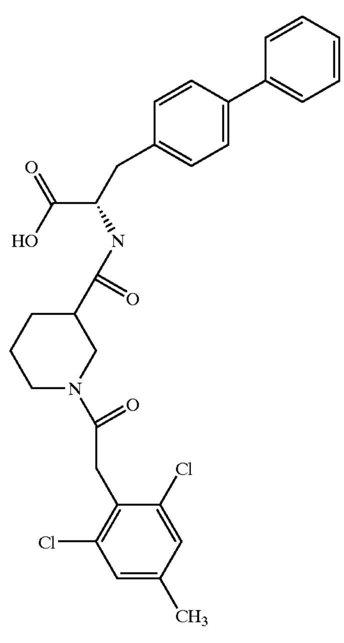 | 553.48 | 554 | 11.9 + 12.2 | 1.12 |

TABLE 1-continued
| structure | MW | MS-ESI | Rt (HPLC) [min] | example |
|---|---|---|---|---|
| 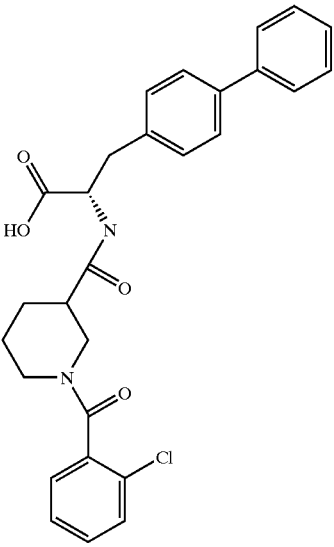 | 490.98 | 491 | 10.1 + 10.6 | 1.13 |
| 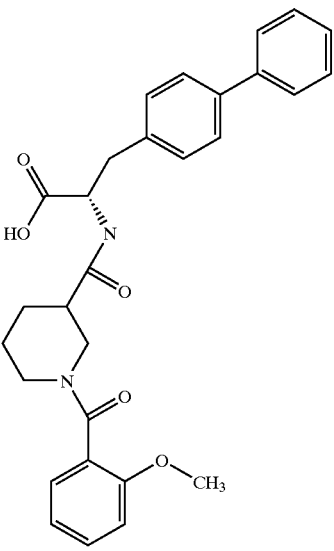 | 486.57 | 487 | 9.6 + 10.1 | 1.14 |

TABLE 1-continued

| structure | MW | MS-ESI | Rt (HPLC) [min] | example |
|---|---|---|---|---|
| (structure with biphenyl, carboxylic acid, piperidine carbamate with 2,4,6-trimethylphenyl ester) | 514.62 | 515 | 12.3 + 12.7 | 1.15 |
| (structure with biphenyl, carboxylic acid, piperidine carbamate with cyclopentyl ester) | 464.56 | 465 | 11.3 + 11.6 | 1.16 |

TABLE 1-continued

| structure | MW | MS-ESI | Rt (HPLC) [min] | example |
|---|---|---|---|---|
| 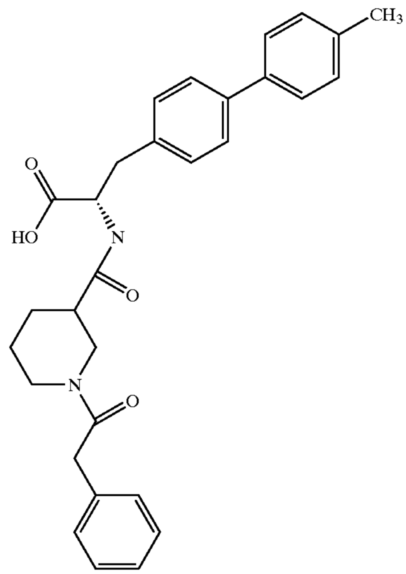 | 484.59 | 485 | 10.9 + 11.2 | 1.17 |
| 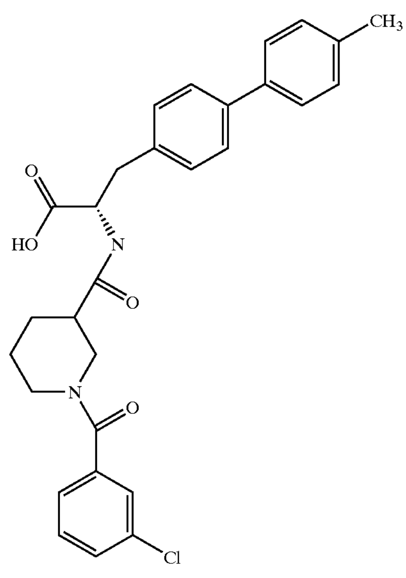 | 505.01 | 506 | 11.3 + 11.7 | 1.18 |

TABLE 1-continued
| structure | MW | MS-ESI | Rt (HPLC) [min] | example |
|---|---|---|---|---|
| 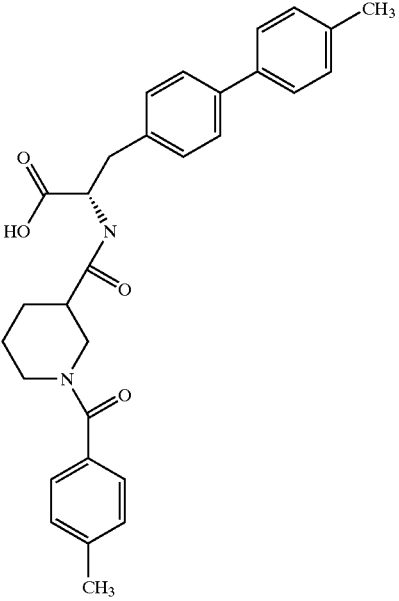 | 484.59 | 485 | 10.9 + 11.5 | 1.19 |
| 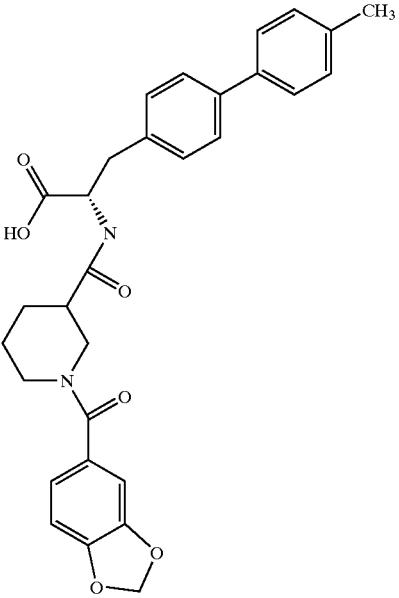 | 514.58 | 515 | 10.3 + 10.8 | 1.20 |

TABLE 1-continued

| structure | MW | MS-ESI | Rt (HPLC) [min] | example |
|---|---|---|---|---|
| 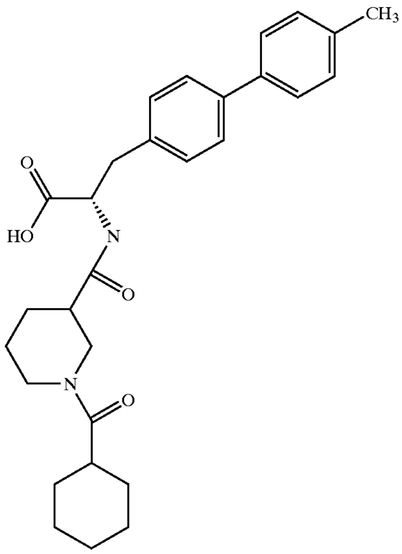 | 476.61 | 477 | 11.7 + 11.9 | 1.21 |
| 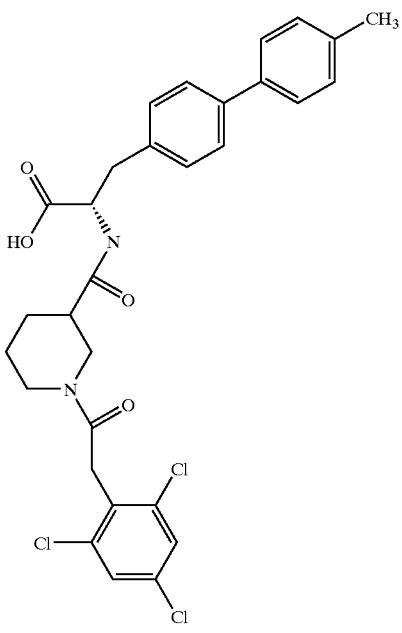 | 567.51 | 568 | 12.5 + 12.8 | 1.22 |

TABLE 1-continued

| structure | MW | MS-ESI | Rt (HPLC) [min] | example |
|---|---|---|---|---|
| 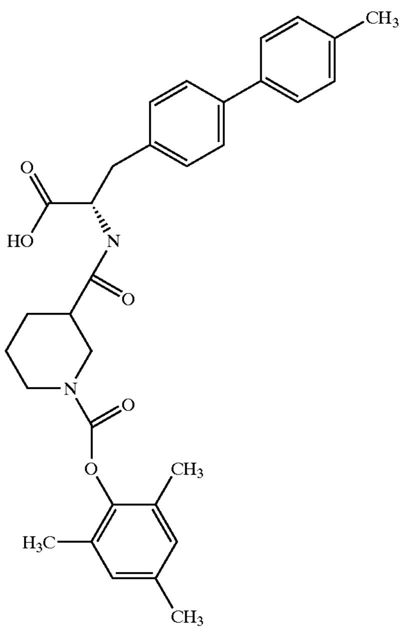 | 528.65 | 529 | 13.0 + 13.3 | 1.23 |
| 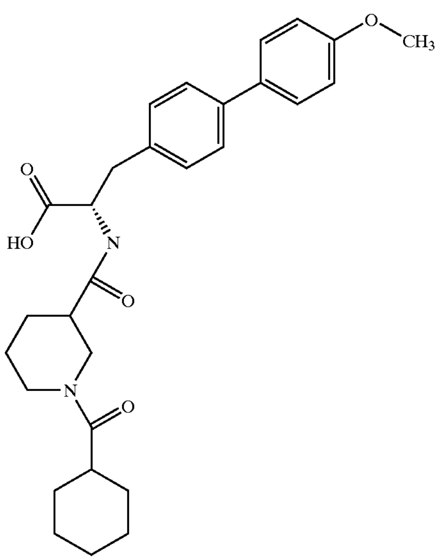 | 492.61 | 493 | 10.7 + 11.0 | 1.24 |

TABLE 1-continued
| structure | MW | MS-ESI | Rt (HPLC) [min] | example |
|---|---|---|---|---|
| 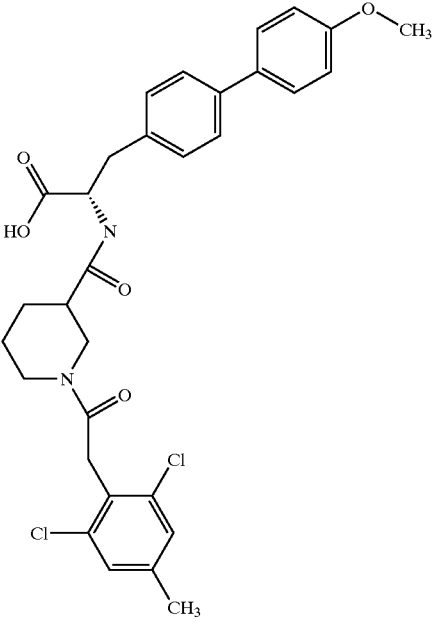 | 583.51 | 584 | 11.6 + 12.0 | 1.25 |
| 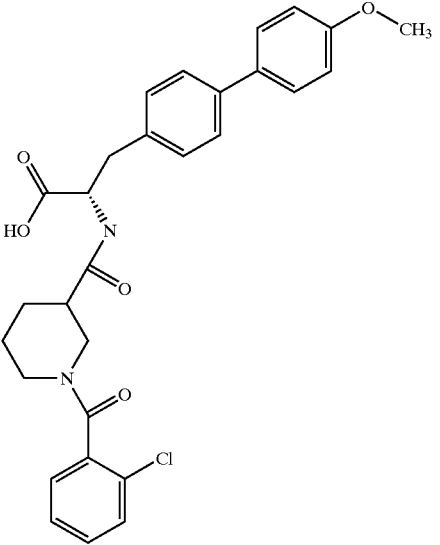 | 521.01 | 522 | 10.0 + 10.5 | 1.26 |

TABLE 1-continued

| structure | MW | MS-ESI | Rt (HPLC) [min] | example |
|---|---|---|---|---|
| 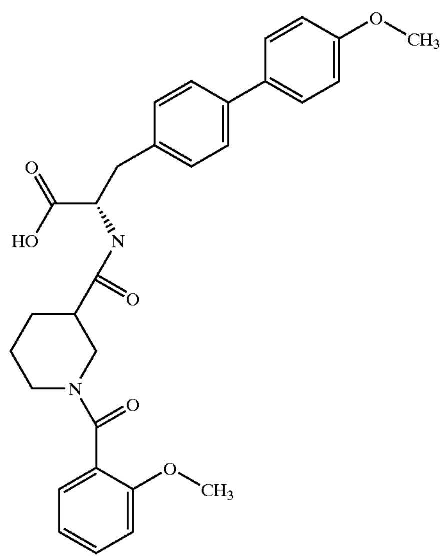 | 516.59 | 517 | 9.5 + 10.0 | 127 |
| 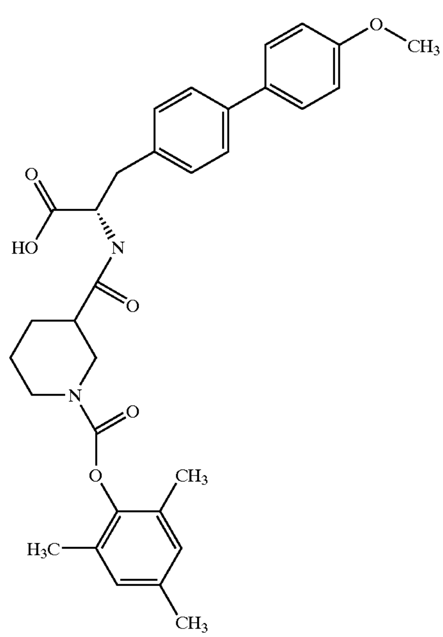 | 544.64 | 545 | 12.1 + 12.5 | 1.28 |

TABLE 1-continued
| structure | MW | MS-ESI | Rt (HPLC) [min] | example |
|---|---|---|---|---|
| 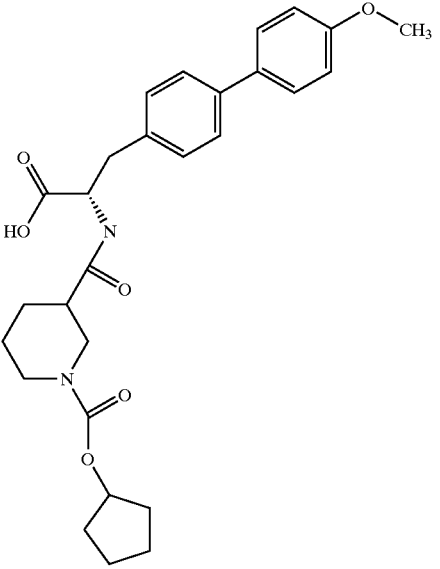 | 494.58 | 495 | 11.1 + 11.4 | 1.29 |
| 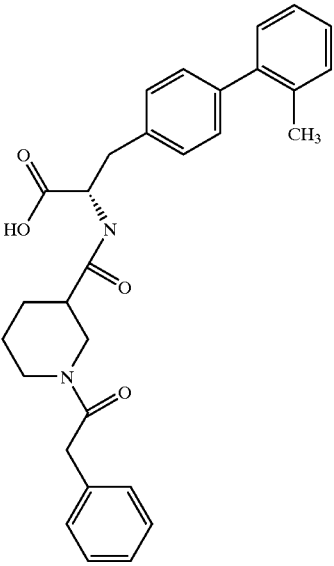 | 484.59 | 485 | 10.7 + 10.9 | 1.30 |

TABLE 1-continued
| structure | MW | MS-ESI | Rt (HPLC) [min] | example |
|---|---|---|---|---|
| 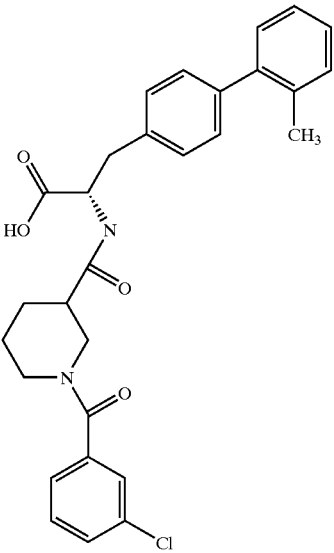 | 505.01 | 506 | 11.0 + 11.4 | 1.31 |
| 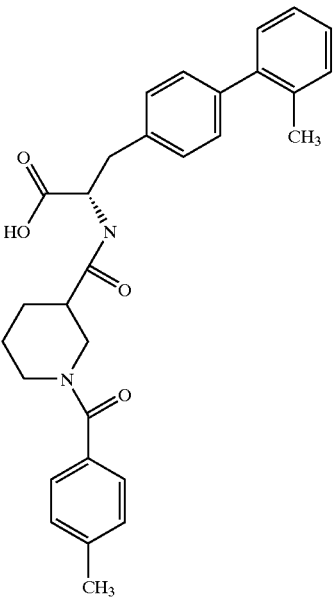 | 484.59 | 485 | 10.8 + 11.3 | 1.32 |

TABLE 1-continued
| structure | MW | MS-ESI | Rt (HPLC) [min] | example |
|---|---|---|---|---|
| 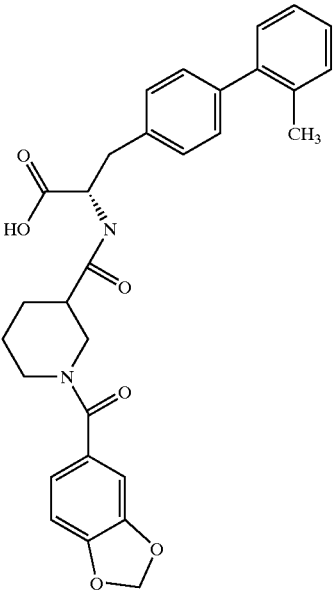 | 514.58 | 515 | 10.0 + 10.3 | 1.33 |
| 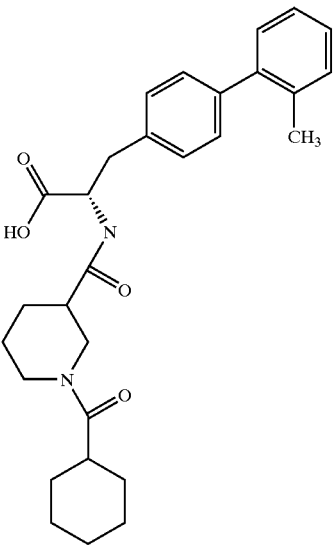 | 476.61 | 477 | 11.4 + 11.6 | 1.34 |

TABLE 1-continued

| structure | MW | MS-ESI | Rt (HPLC) [min] | example |
|---|---|---|---|---|
| 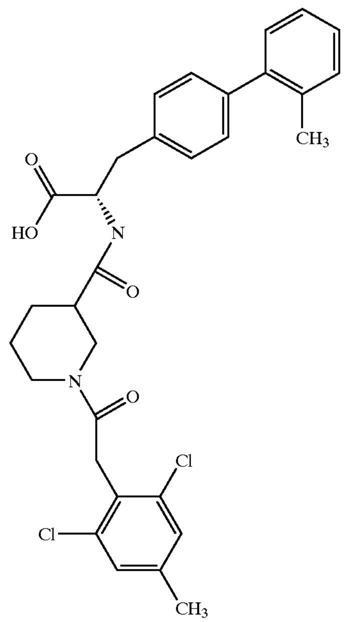 | 567.51 | 568 | 12.4 + 12.6 | 1.35 |
| 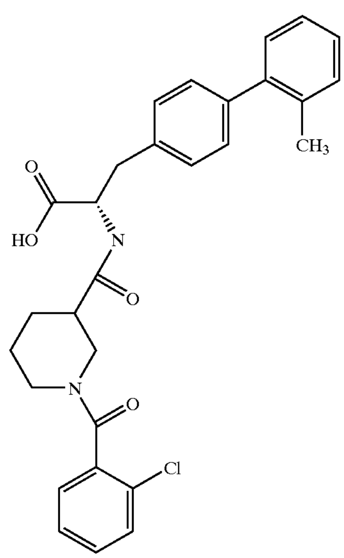 | 505.01 | 505 | 10.6 + 11.1 | 1.36 |

TABLE 1-continued

| structure | MW | MS-ESI | Rt (HPLC) [min] | example |
|---|---|---|---|---|
| 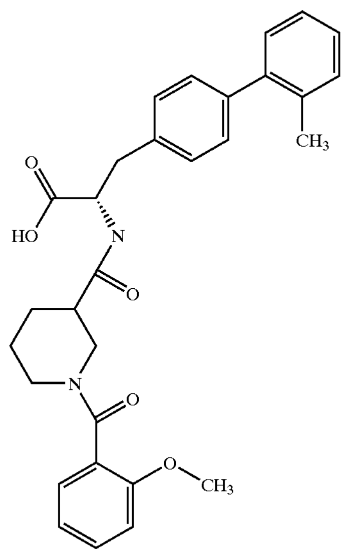 | 500.59 | 501 | 10.1 + 10.7 | 1.37 |
| 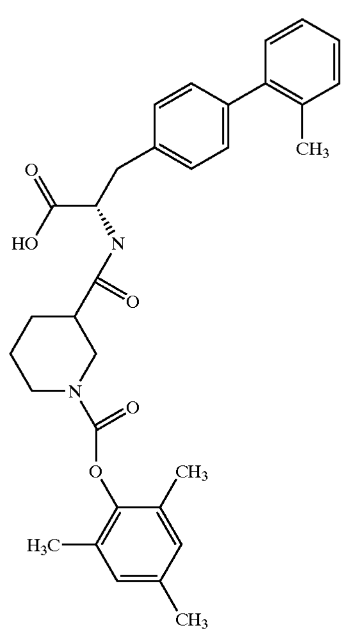 | 528.65 | 529 | 12.8 + 13.1 | 1.38 |

TABLE 1-continued

| structure | MW | MS-ESI | Rt (HPLC) [min] | example |
|---|---|---|---|---|
| 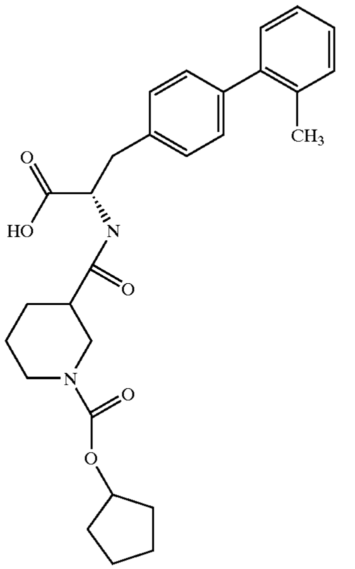 | 478.59 | 479 | 11.8 + 12.1 | 1.39 |
| 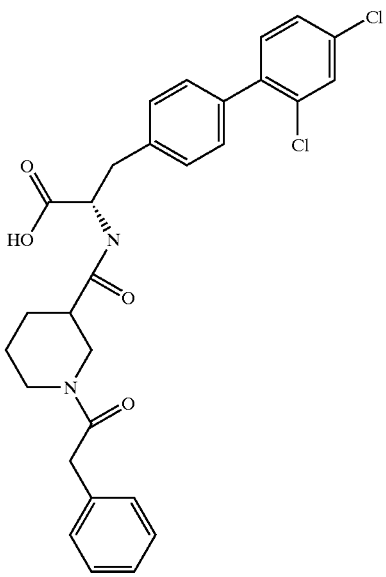 | 539.46 | 540 | 11.8 + 12.1 | 1.40 |

TABLE 1-continued

| structure | MW | MS-ESI | Rt (HPLC) [min] | example |
|---|---|---|---|---|
| 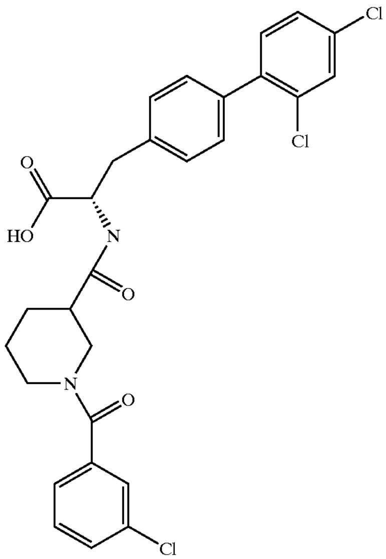 | 559.87 | 560 | 12.1 + 12.5 | 1.41 |
| 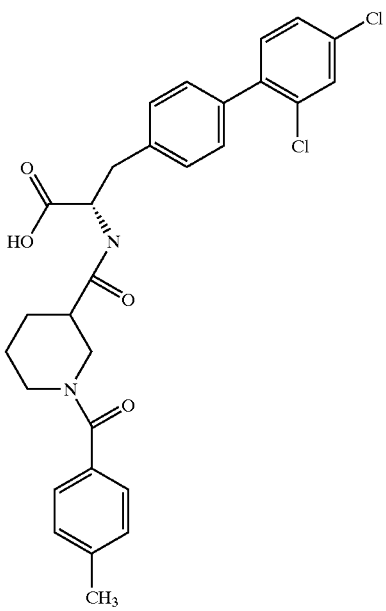 | 539.46 | 540 | 11.9 + 12.4 | 1.42 |

TABLE 1-continued
| structure | MW | MS-ESI | Rt (HPLC) [min] | example |
|---|---|---|---|---|
| 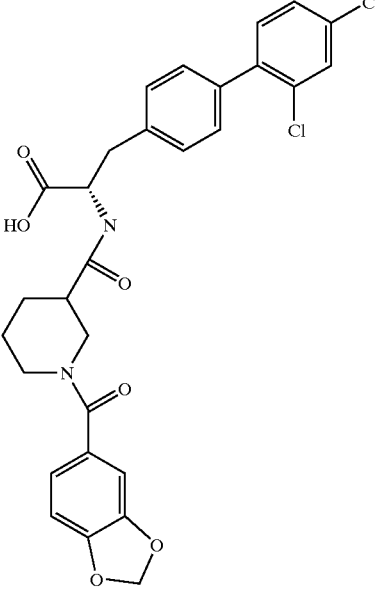 | 569.44 | 570 | 11.0 + 11.7 | 1.43 |
| 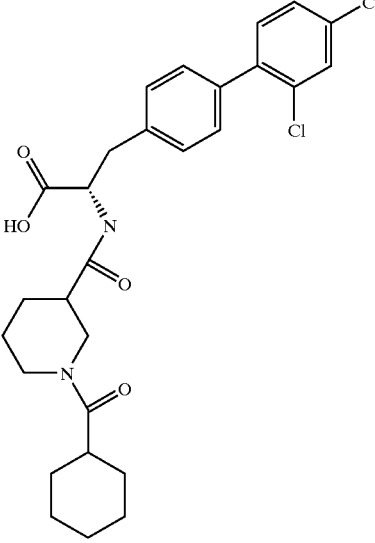 | 531.48 | 532 | 12.6 + 12.8 | 1.44 |

TABLE 1-continued

| structure | MW | MS-ESI | Rt (HPLC) [min] | example |
|---|---|---|---|---|
| 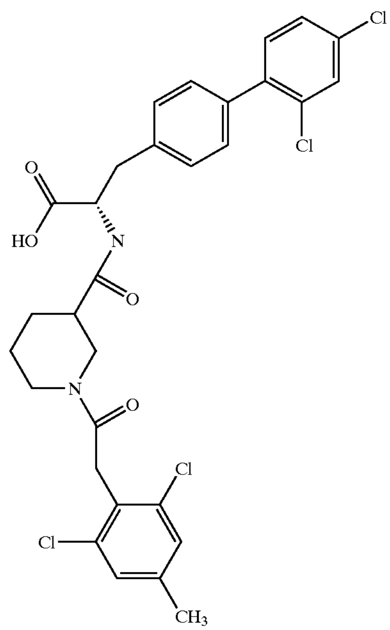 | 622.37 | 623 | 13.3 + 13.6 | 1.45 |
| 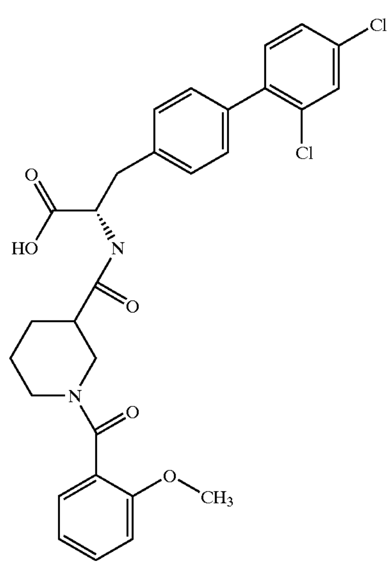 | 555.46 | 556 | 11.2 + 11.8 | 1.46 |

TABLE 1-continued
| structure | MW | MS-ESI | Rt (HPLC) [min] | example |
|---|---|---|---|---|
| 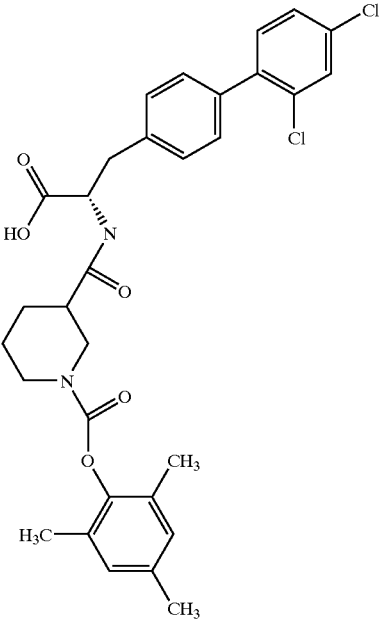 | 583.51 | 584 | 13.7 + 14.1 | 1.47 |
| 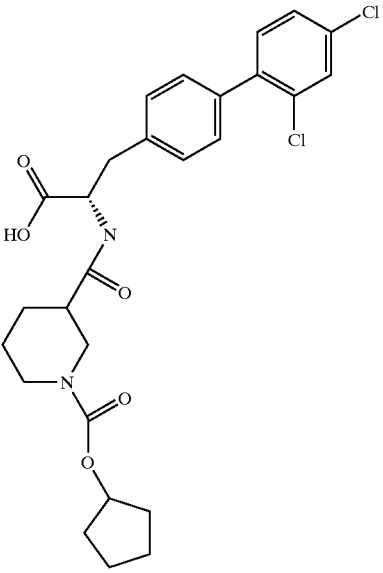 | 533.45 | 534 | 13.0 + 13.2 | 1.48 |

TABLE 1-continued
| structure | MW | MS-ESI | Rt (HPLC) [min] | example |
|---|---|---|---|---|
| 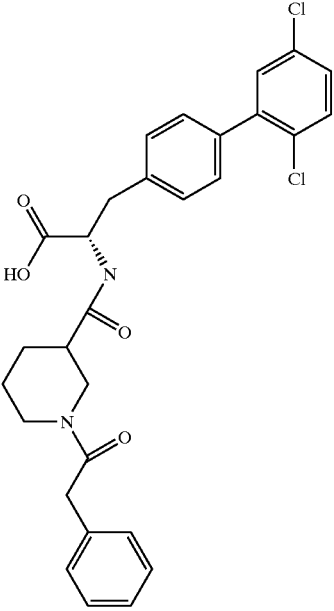 | 539.46 | 540 | 11.5 + 11.8 | 1.49 |
| 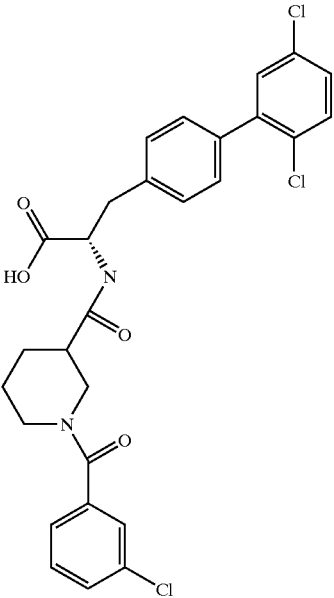 | 559.87 | 560 | 11.8 + 12.2 | 1.50 |

TABLE 1-continued
| structure | MW | MS-ESI | Rt (HPLC) [min] | example |
|---|---|---|---|---|
| 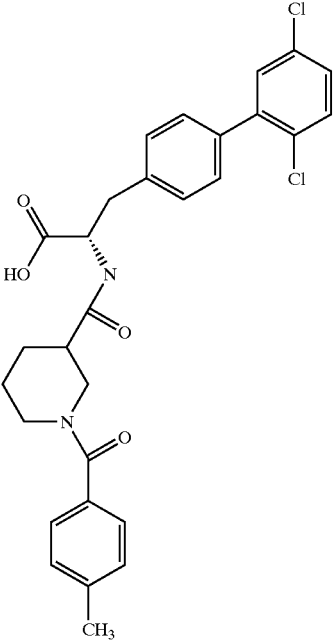 | 539.46 | 540 | 11.6 + 12.1 | 1.51 |
| 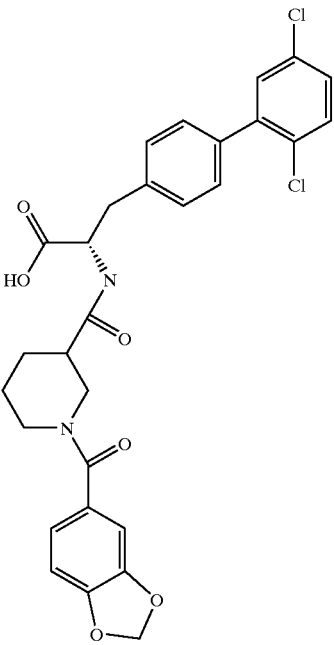 | 569.44 | 570 | 10.7 + 11.4 | 1.52 |

TABLE 1-continued
| structure | MW | MS-ESI | Rt (HPLC) [min] | example |
|---|---|---|---|---|
| 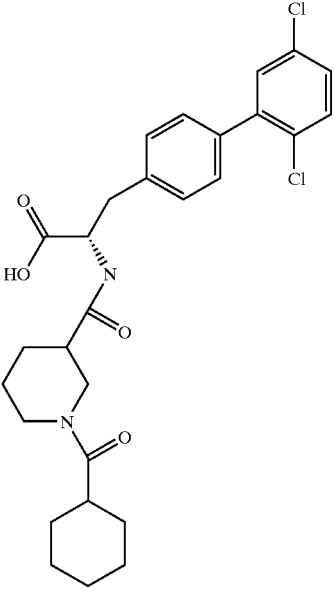 | 531.48 | 532 | 12.3 + 12.5 | 1.53 |
| 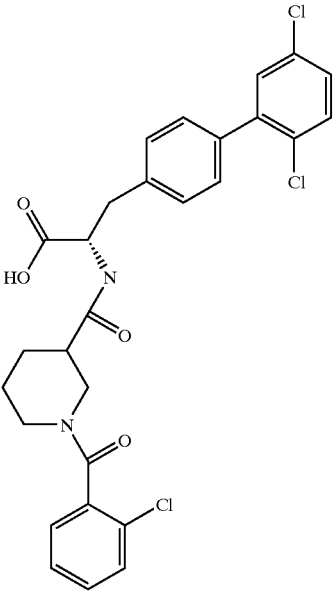 | 559.87 | 560 | 11.4 + 12.0 | 1.54 |

TABLE 1-continued

| structure | MW | MS-ESI | Rt (HPLC) [min] | example |
|---|---|---|---|---|
| 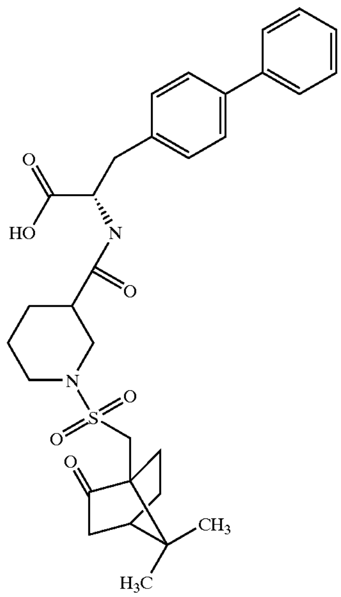 | 566.72 | 567 | 11.1 + 11.3 | 1.55 |
| 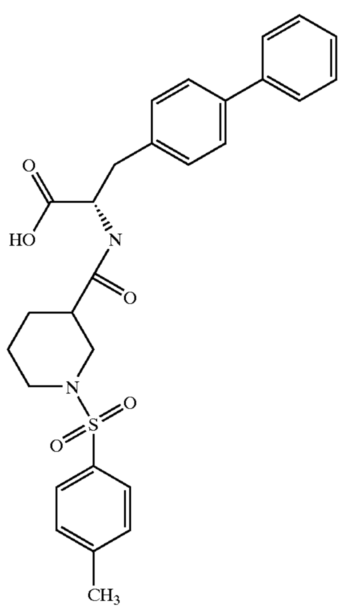 | 506.62 | 507 | 11.2 + 11.5 | 1.56 |

TABLE 1-continued

| structure | MW | MS-ESI | Rt (HPLC) [min] | example |
|---|---|---|---|---|
| 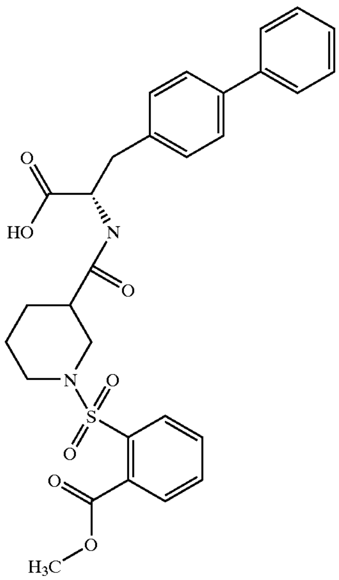 | 550.63 | 551 | 10.5 + 10.8 | 1.57 |
| 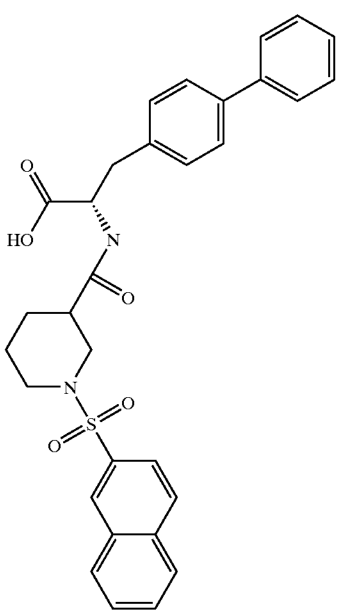 | 542.65 | 543 | 11.9 + 12.1 | 1.58 |

TABLE 1-continued
| structure | MW | MS-ESI | Rt (HPLC) [min] | example |
|---|---|---|---|---|
| 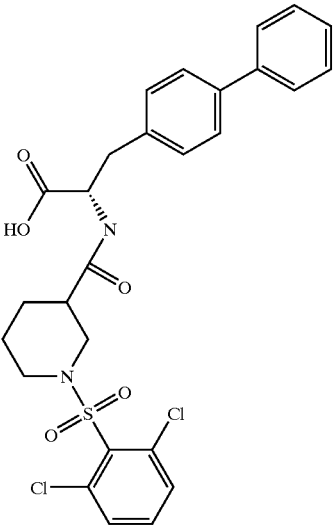 | 561.48 | 562 | 11.4 + 11.7 | 1.59 |
| 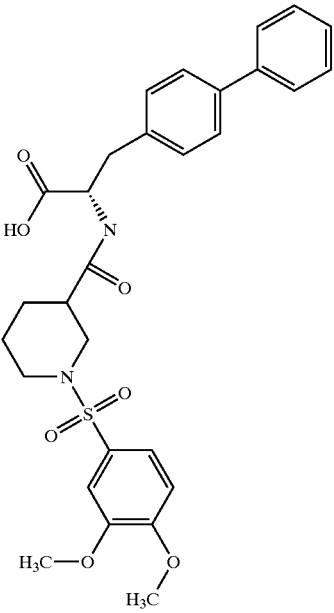 | 552.64 | 553 | 10.3 + 10.6 | 1.60 |

TABLE 1-continued
| structure | MW | MS-ESI | Rt (HPLC) [min] | example |
|---|---|---|---|---|
| 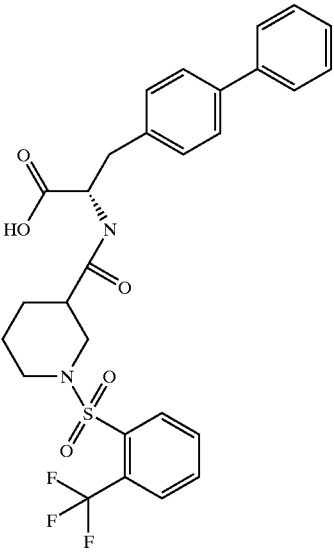 | 560.59 | 561 | 11.4 + 11.6 | 1.61 |
| 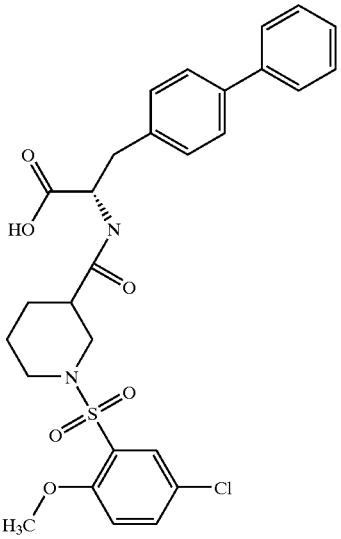 | 557.06 | 558 | 11.4 + 11.6 | 1.62 |

TABLE 1-continued

| structure | MW | MS-ESI | Rt (HPLC) [min] | example |
|---|---|---|---|---|
| 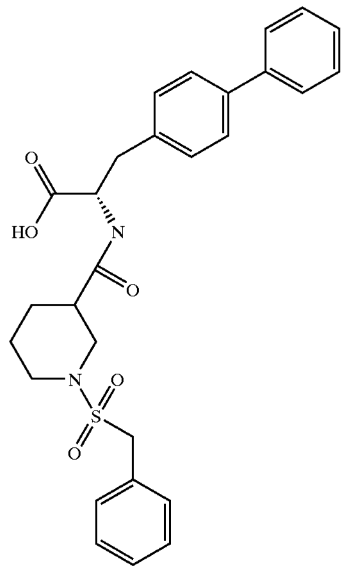 | 506.62 | 507 | 10.7 + 10.9 | 1.63 |
| 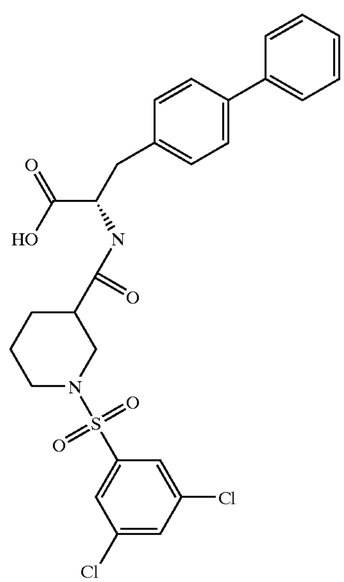 | 561.48 | 562 | 12.5 | 1.64 |

TABLE 1-continued

| structure | MW | MS-ESI | Rt (HPLC) [min] | example |
|---|---|---|---|---|
| 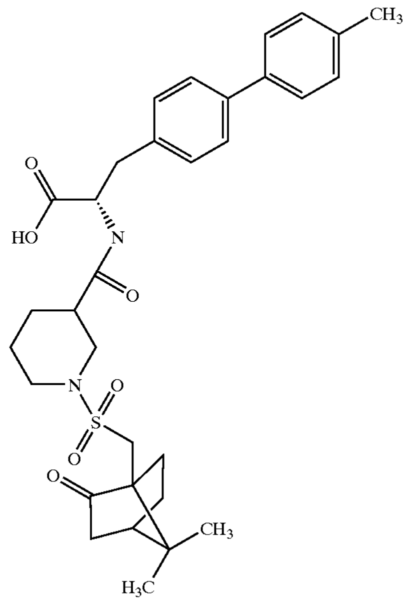 | 580.74 | 581 | 11.8 + 12.0 | 1.65 |
| 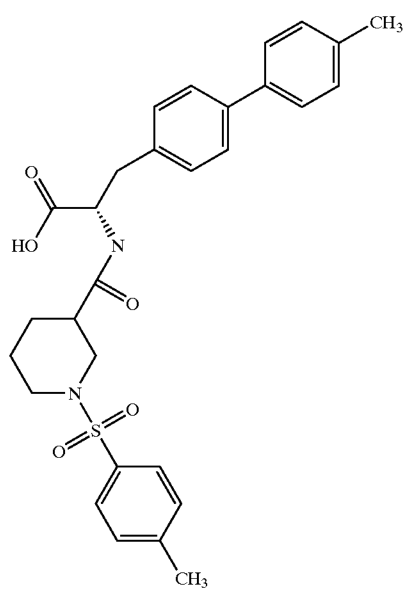 | 520.65 | 521 | 11.9 + 12.1 | 1.66 |

TABLE 1-continued
| structure | MW | MS-ESI | Rt (HPLC) [min] | example |
|---|---|---|---|---|
| 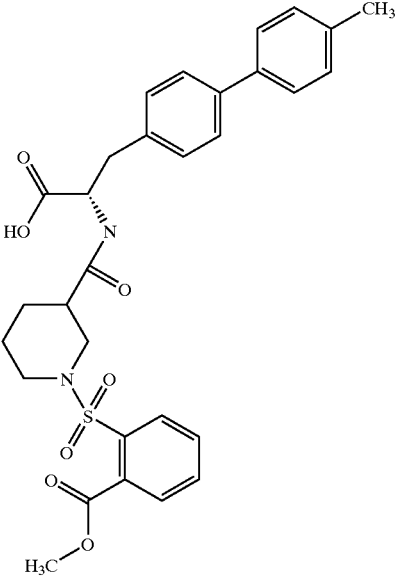 | 564.66 | 565 | 11.1 + 11.4 | 1.67 |
| 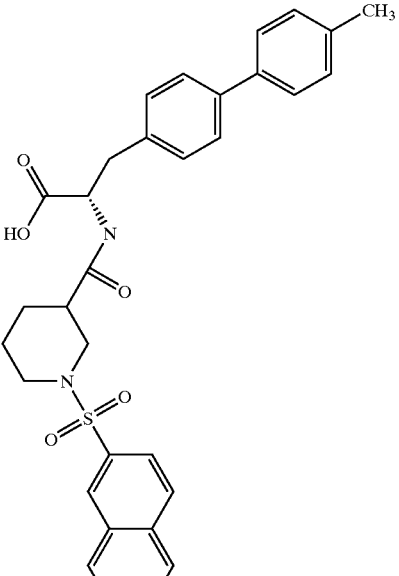 | 556.68 | 557 | 12.5 + 12.7 | 1.68 |

TABLE 1-continued
| structure | MW | MS-ESI | Rt (HPLC) [min] | example |
|---|---|---|---|---|
| 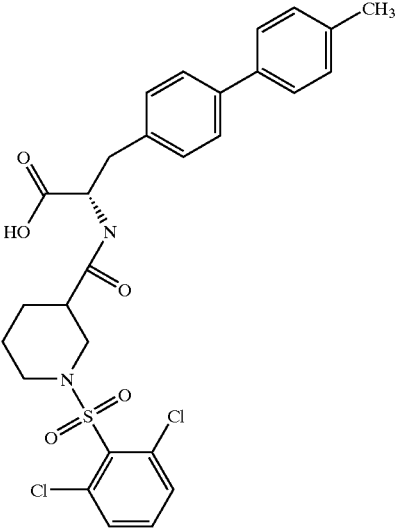 | 575.51 | 576 | 12.1 + 12.3 | 1.69 |
| 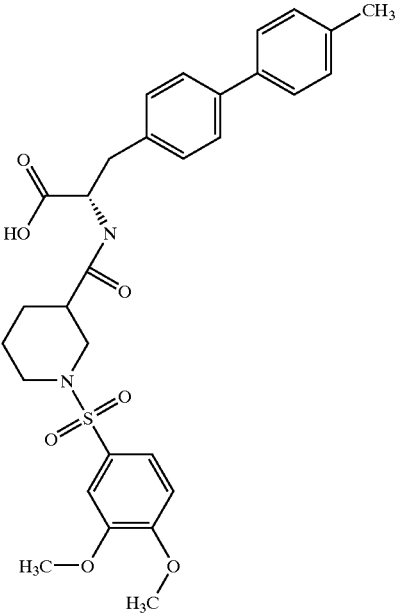 | 566.67 | 567 | 11.0 + 11.3 | 1.70 |

TABLE 1-continued

| structure | MW | MS-ESI | Rt (HPLC) [min] | example |
|---|---|---|---|---|
| 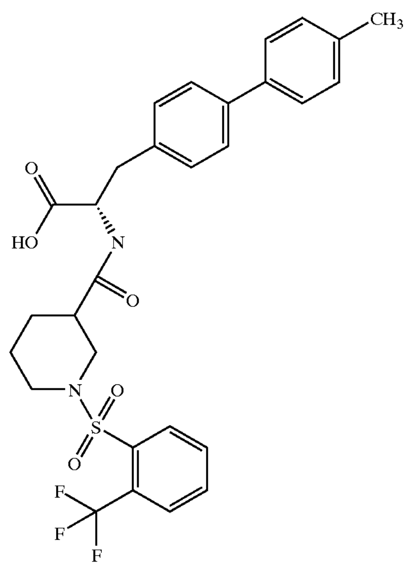 | 574.62 | 575 | 12.0 + 12.2 | 1.71 |
| 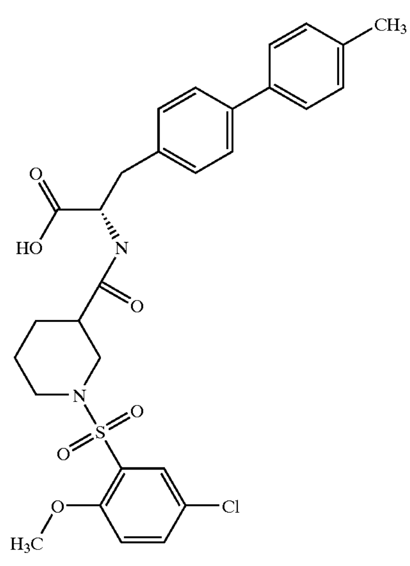 | 571.09 | 572 | 11.3 + 11.6 | 1.72 |

TABLE 1-continued
| structure | MW | MS-ESI | Rt (HPLC) [min] | example |
|---|---|---|---|---|
| 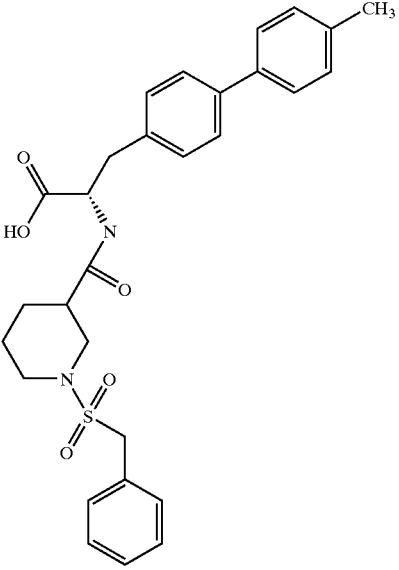 | 520.65 | 521 | 12.0 + 12.3 | 1.73 |
| 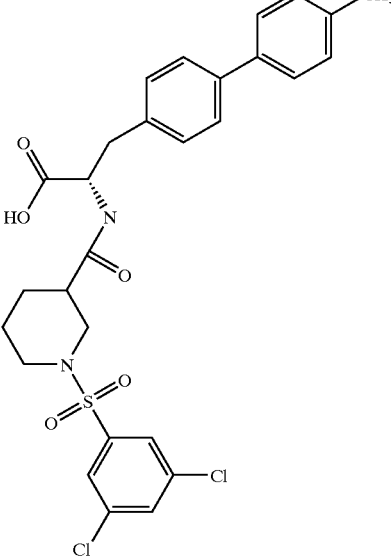 | 575.51 | 576 | 13.2 | 1.74 |

TABLE 1-continued
| structure | MW | MS-ESI | Rt (HPLC) [min] | example |
|---|---|---|---|---|
| 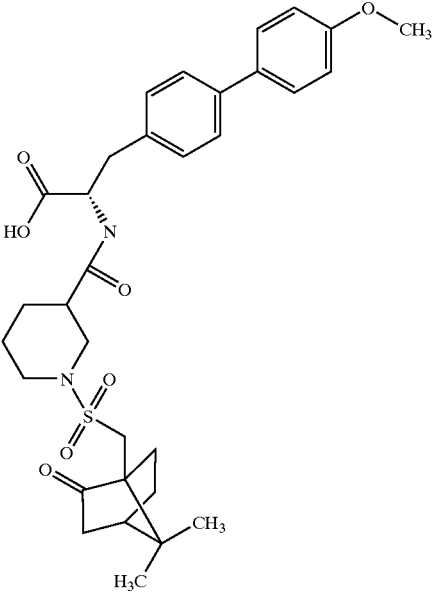 | 596.74 | 597 | 11.0 + 11.2 | 1.75 |
| 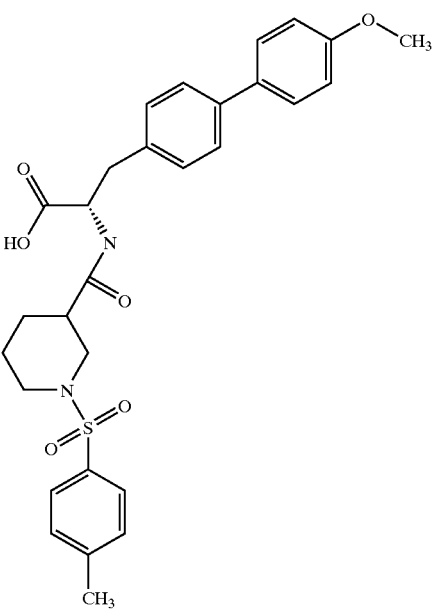 | 536.65 | 537 | 11.0 + 11.3 | 1.76 |

TABLE 1-continued
| structure | MW | MS-ESI | Rt (HPLC) [min] | example |
|---|---|---|---|---|
| 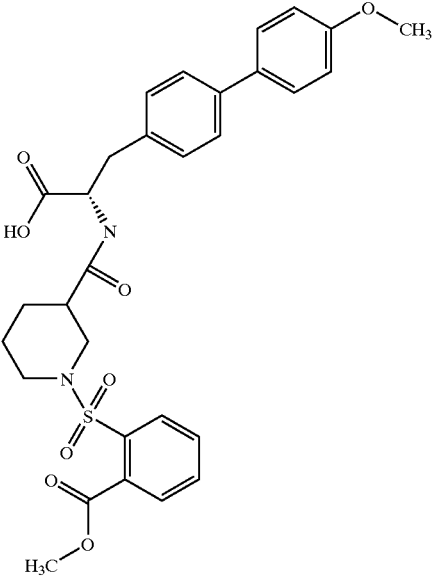 | 580.65 | 581 | 10.4 + 10.7 | 1.77 |
| 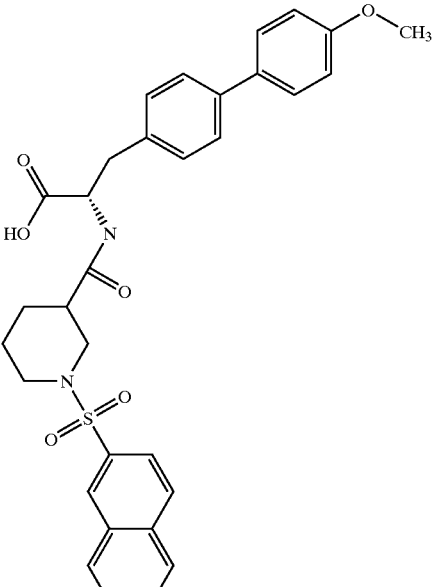 | 572.68 | 573 | 11.7 + 12.0 | 1.78 |

TABLE 1-continued
| structure | MW | MS-ESI | Rt (HPLC) [min] | example |
|---|---|---|---|---|
| 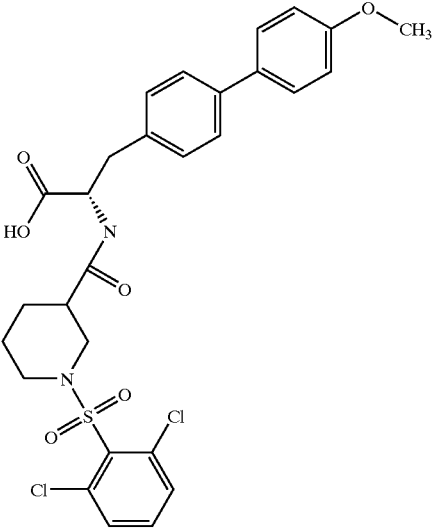 | 591.51 | 592 | 11.3 + 11.6 | 1.79 |
| 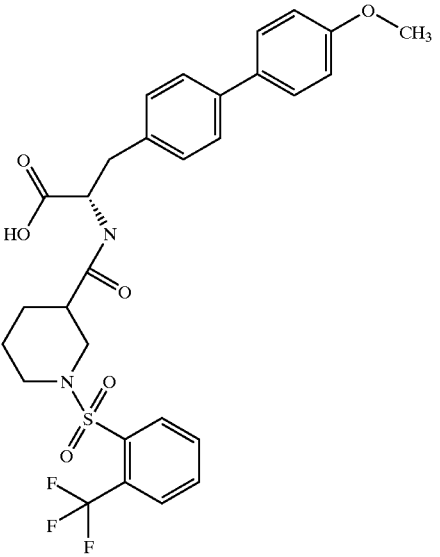 | 590.62 | 591 | 11.2 + 11.5 | 1.80 |

TABLE 1-continued

| structure | MW | MS-ESI | Rt (HPLC) [min] | example |
|---|---|---|---|---|
| 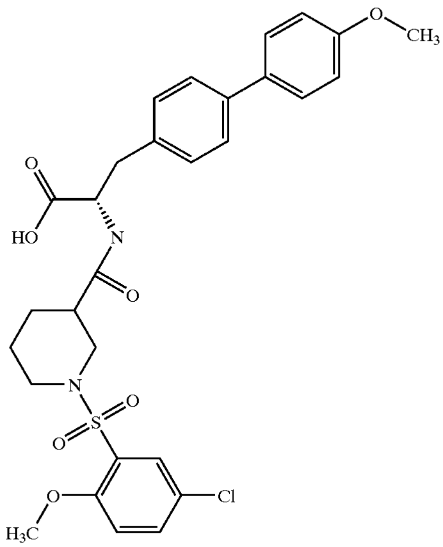 | 587.09 | 588 | 11.3 + 11.5 | 1.81 |
| 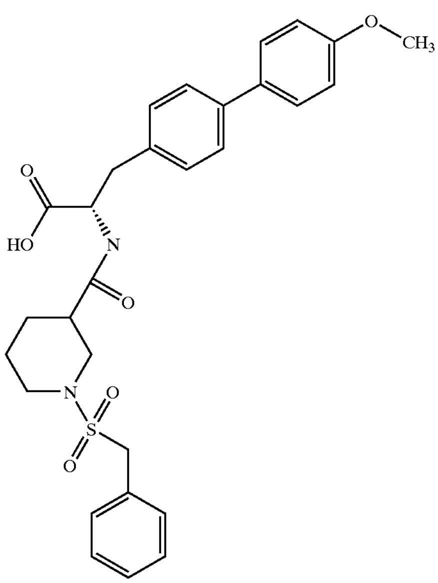 | 536.65 | 537 | 10.5 + 10.8 | 1.82 |

TABLE 1-continued

| structure | MW | MS-ESI | Rt (HPLC) [min] | example |
|---|---|---|---|---|
| 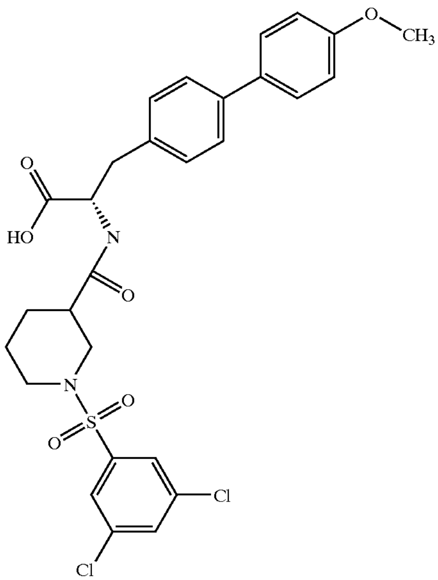 | 591.51 | 592 | 12.3 + 12.5 | 1.83 |
| 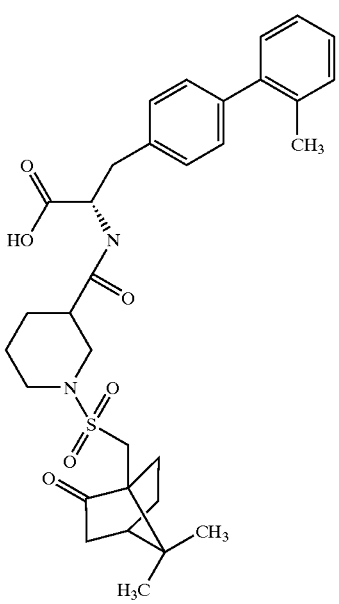 | 580.74 | 581 | 11.6 + 11.8 | 1.84 |

TABLE 1-continued
| structure | MW | MS-ESI | Rt (HPLC) [min] | example |
|---|---|---|---|---|
| 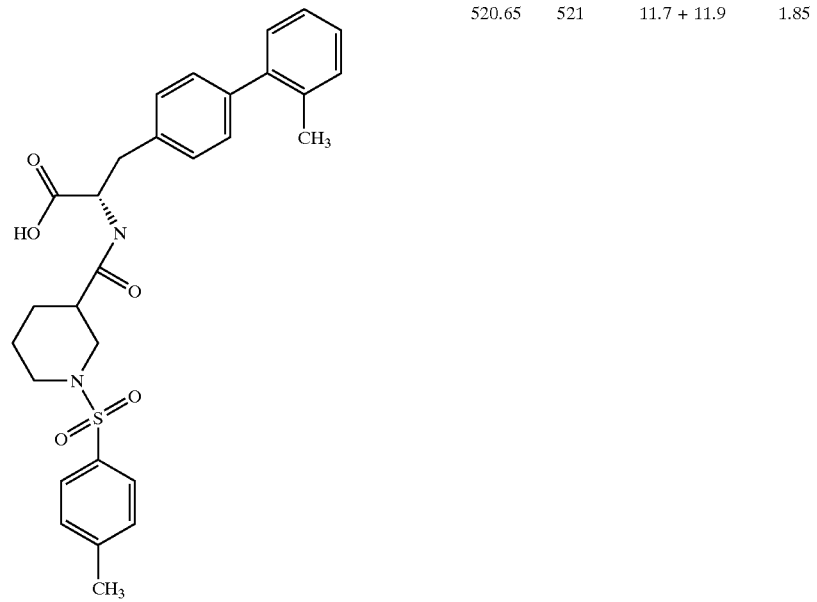 | 520.65 | 521 | 11.7 + 11.9 | 1.85 |
| 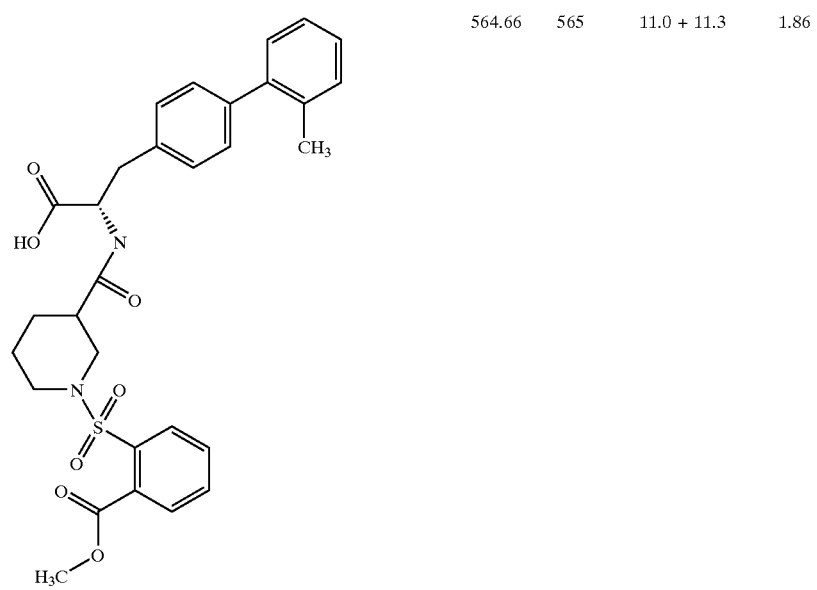 | 564.66 | 565 | 11.0 + 11.3 | 1.86 |

TABLE 1-continued
| structure | MW | MS-ESI | Rt (HPLC) [min] | example |
|---|---|---|---|---|
| 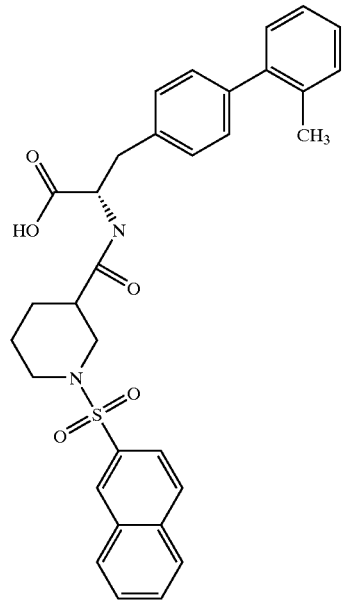 | 556.68 | 557 | 12.4 + 12.5 | 1.87 |
| 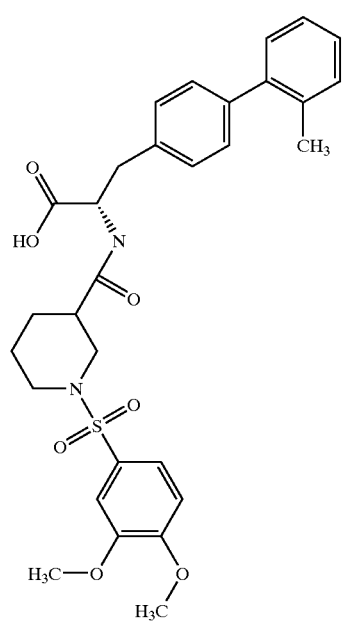 | 566.67 | 567 | 10.9 + 11.1 | 1.88 |

TABLE 1-continued

| structure | MW | MS-ESI | Rt (HPLC) [min] | example |
|---|---|---|---|---|
| 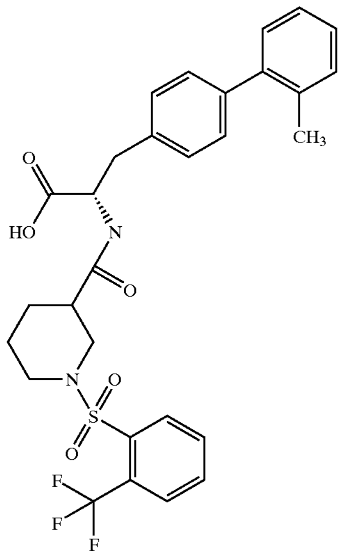 | 574.62 | 575 | 11.8 + 12.1 | 1.89 |
| 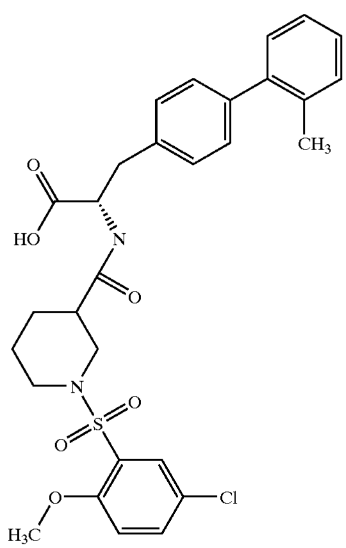 | 571.09 | 572 | 11.8 + 12.1 | 1.90 |

TABLE 1-continued
| structure | MW | MS-ESI | Rt (HPLC) [min] | example |
|---|---|---|---|---|
| 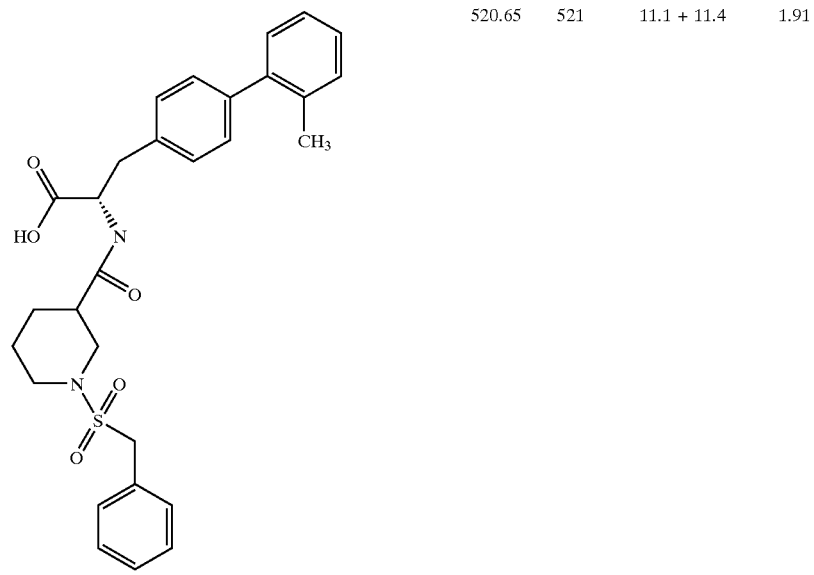 | 520.65 | 521 | 11.1 + 11.4 | 1.91 |
| 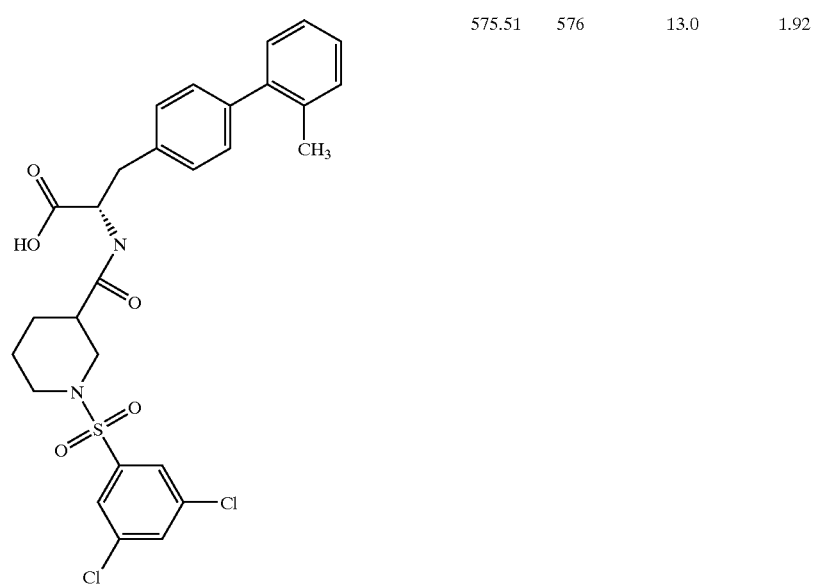 | 575.51 | 576 | 13.0 | 1.92 |

TABLE 1-continued

| structure | MW | MS-ESI | Rt (HPLC) [min] | example |
|---|---|---|---|---|
| 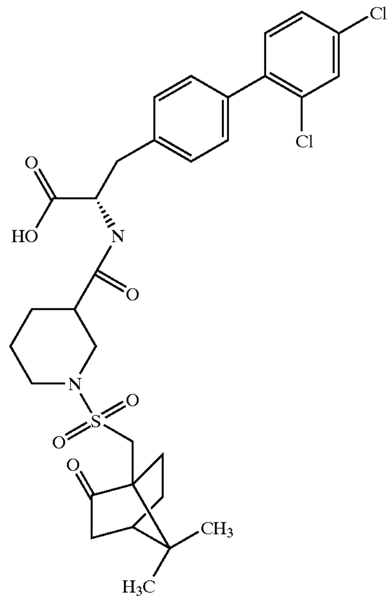 | 635.61 | 636 | 12.6 + 12.8 | 1.93 |
| 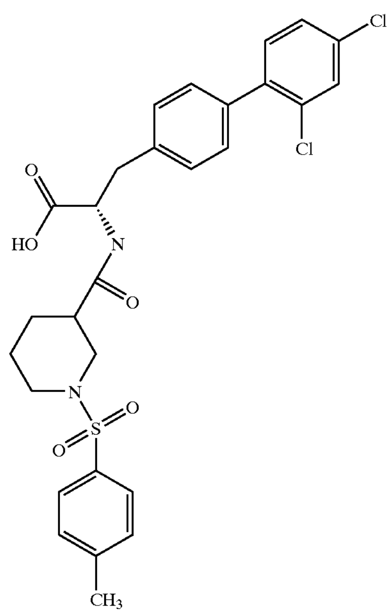 | 575.51 | 576 | 12.7 + 12.9 | 1.94 |

TABLE 1-continued
| structure | MW | MS-ESI | Rt (HPLC) [min] | example |
|---|---|---|---|---|
| 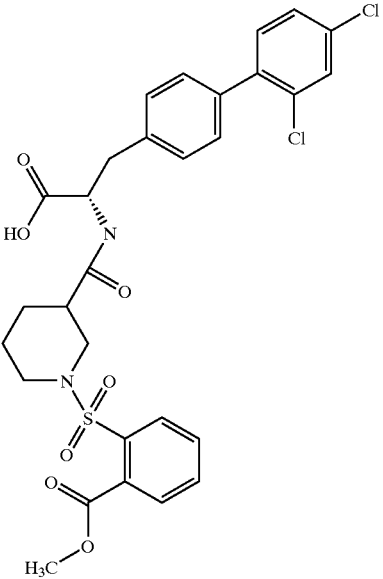 | 619.52 | 620 | 11.9 + 12.2 | 1.95 |
| 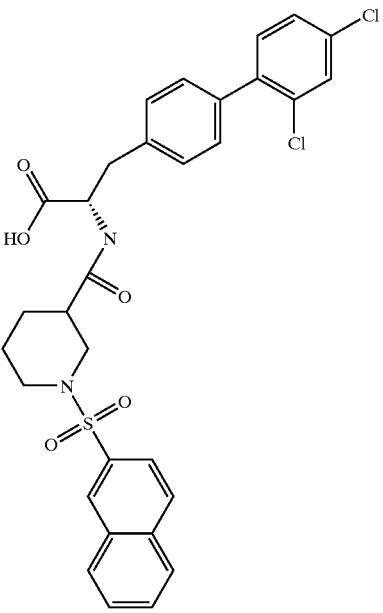 | 611.54 | 612 | 13.2 + 13.5 | 1.96 |

TABLE 1-continued

| structure | MW | MS-ESI | Rt (HPLC) [min] | example |
|---|---|---|---|---|
| 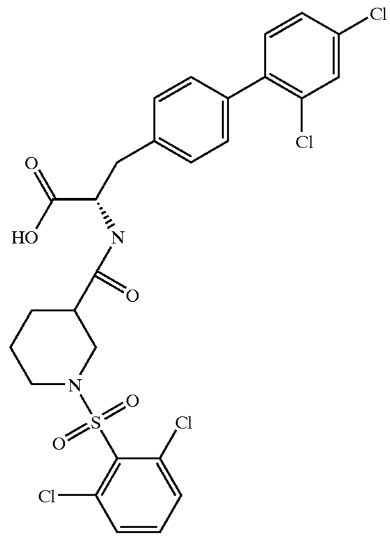 | 630.37 | 631 | 12.8 + 13.1 | 1.97 |
| 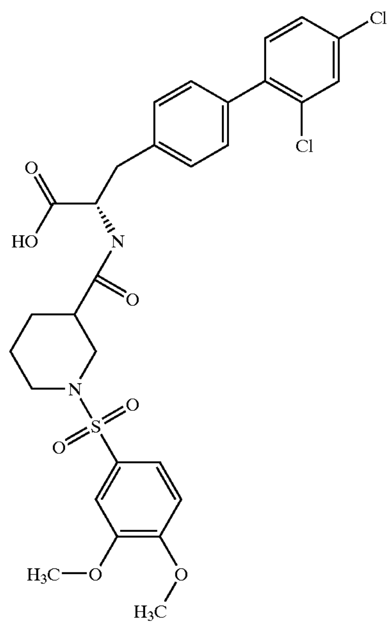 | 621.54 | 622 | 9.6 | 1.98 |

TABLE 1-continued

| structure | MW | MS-ESI | Rt (HPLC) [min] | example |
|---|---|---|---|---|
| 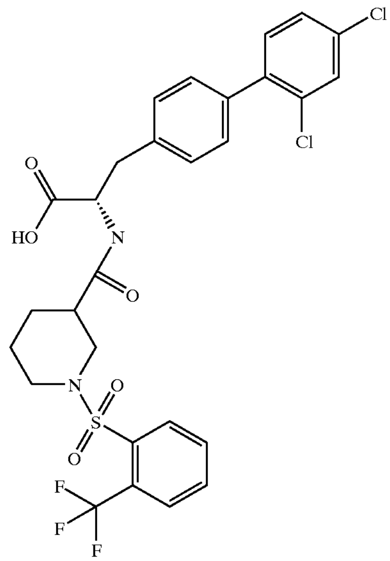 | 629.48 | 630 | 10.7 | 1.99 |
| 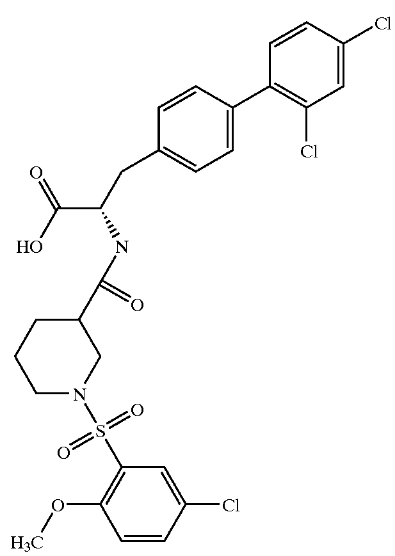 | 625.95 | 626 | 10.9 | 1.100 |

TABLE 1-continued
| structure | MW | MS-ESI | Rt (HPLC) [min] | example |
|---|---|---|---|---|
| 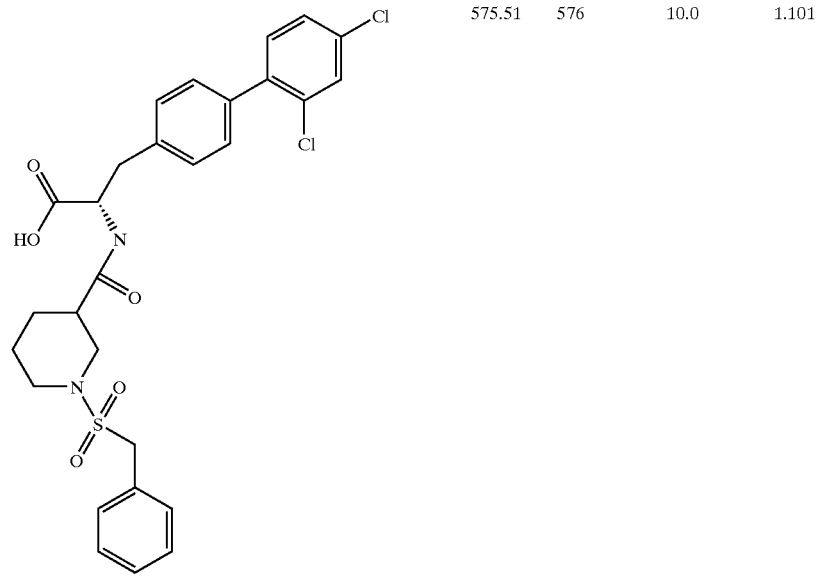 | 575.51 | 576 | 10.0 | 1.101 |
| 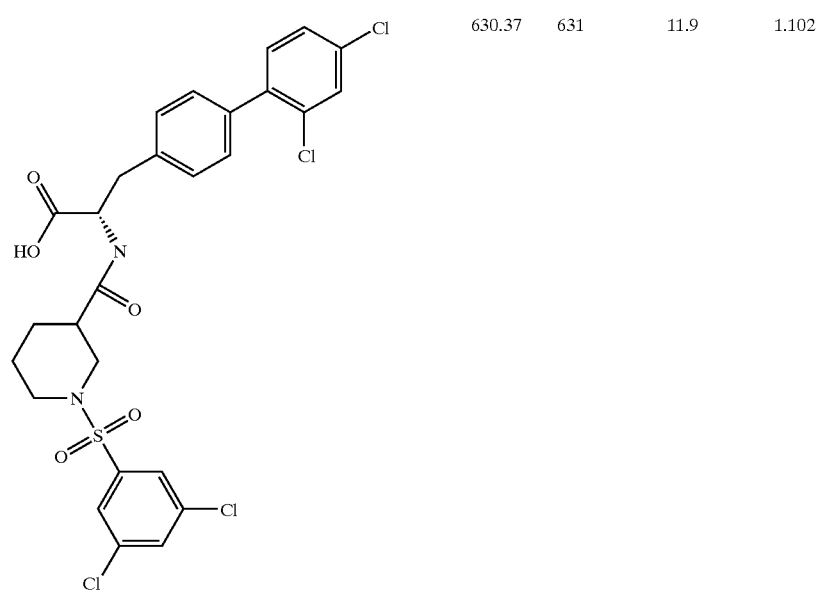 | 630.37 | 631 | 11.9 | 1.102 |

TABLE 1-continued
| structure | MW | MS-ESI | Rt (HPLC) [min] | example |
|---|---|---|---|---|
| 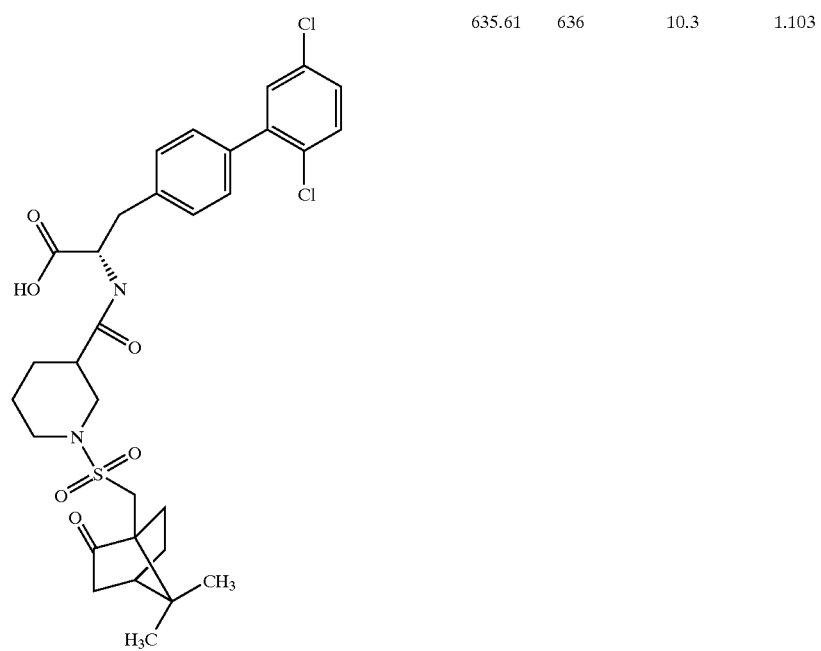 | 635.61 | 636 | 10.3 | 1.103 |
| 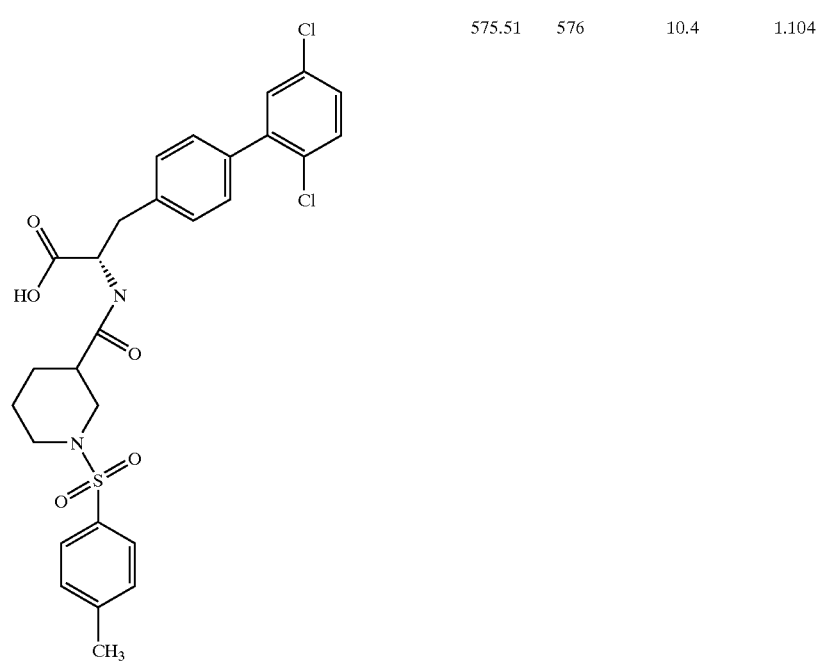 | 575.51 | 576 | 10.4 | 1.104 |

TABLE 1-continued

| structure | MW | MS-ESI | Rt (HPLC) [min] | example |
|---|---|---|---|---|
| (structure) | 619.52 | 620 | 9.3 | 1.105 |
| (structure) | 611.54 | 612 | 11.0 | 1.106 |

TABLE 1-continued
| structure | MW | MS-ESI | Rt (HPLC) [min] | example |
|---|---|---|---|---|
| 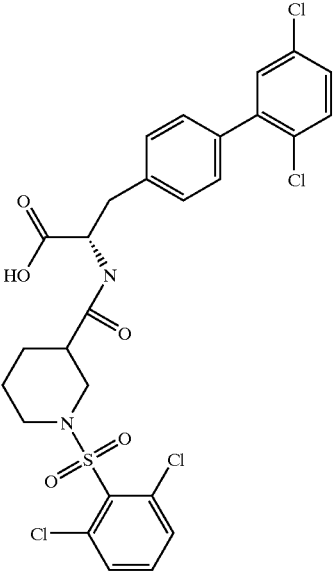 | 630.37 | 631 | 10.6 | 1.107 |
| 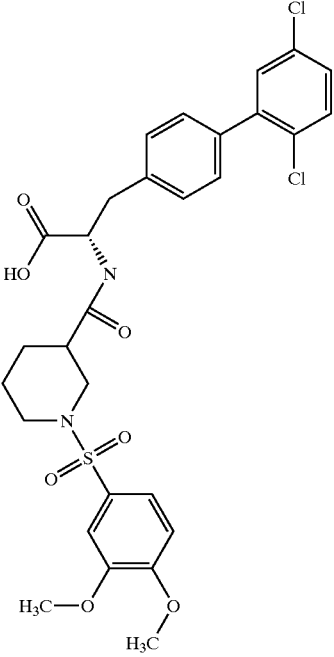 | 621.54 | 622 | 8.8 + 9.2 | 1.108 |

TABLE 1-continued

| structure | MW | MS-ESI | Rt (HPLC) [min] | example |
|---|---|---|---|---|
| 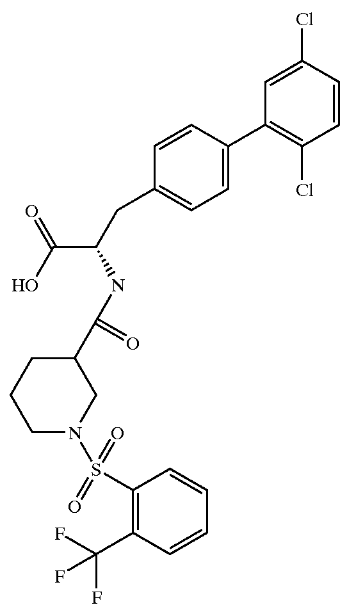 | 629.48 | 630 | 10.3 | 1.109 |
| 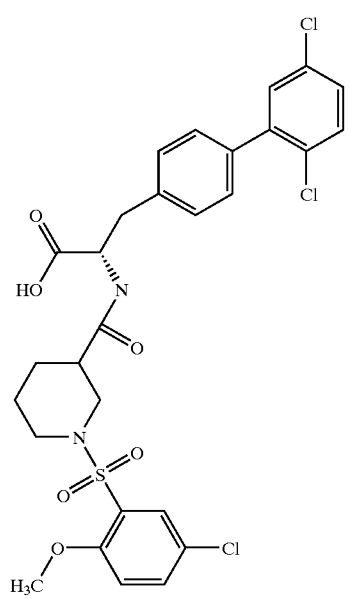 | 625.95 | 626 | 10.0 + 10.5 | 1.110 |

TABLE 1-continued
| structure | MW | MS-ESI | Rt (HPLC) [min] | example |
|---|---|---|---|---|
| 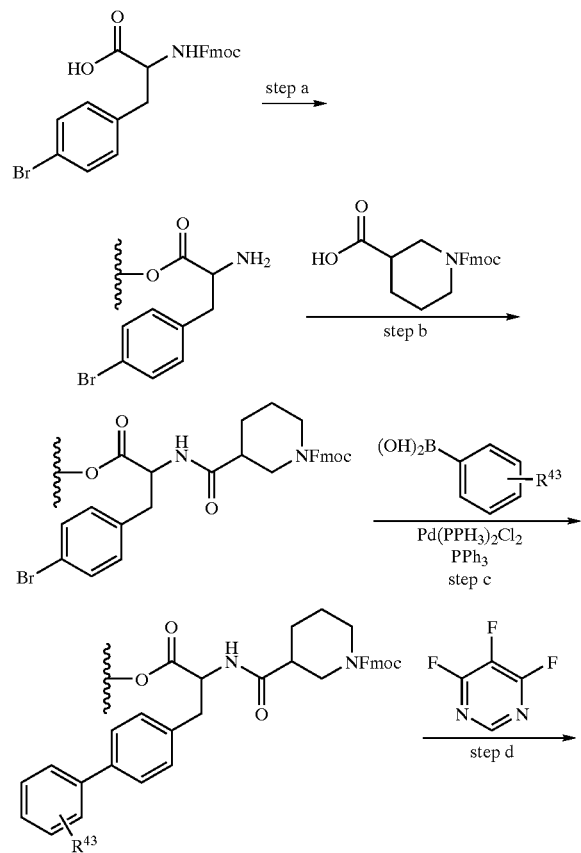 | 630.37 | 631 | 11.5 | 1.111 |
Example 2
General synthesis scheme:
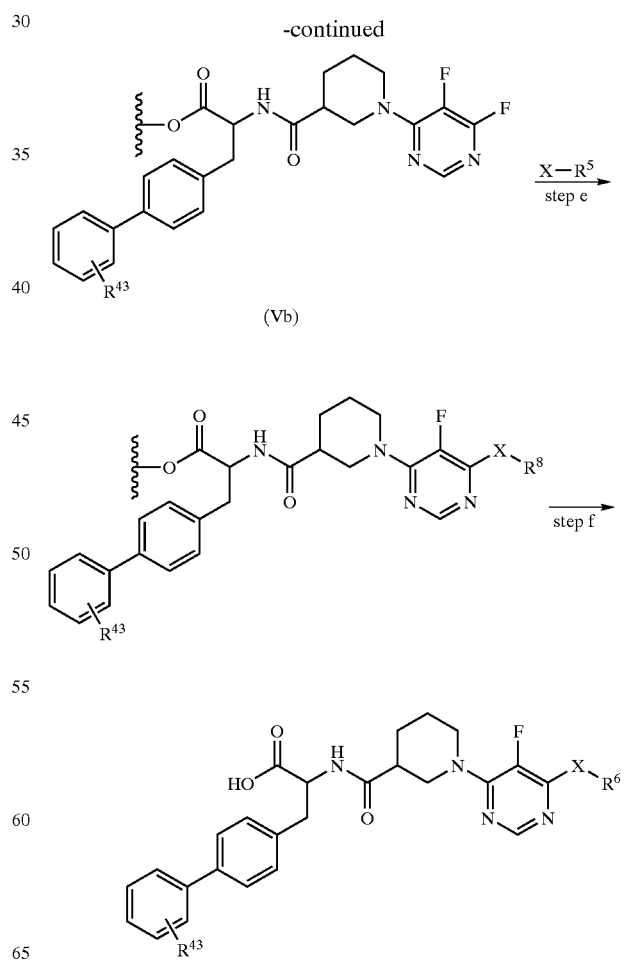

Example 2.1

(2S-3-(2',5'dichloro[1,1'-biphenyl]-4-yl)-2-{[(1-{5-fluoro-6-[(2-pyridinylmethyl)-amino]-4-pyrimidinyl}-3-piperidinyl)carbonyl]amino}propanoic acid

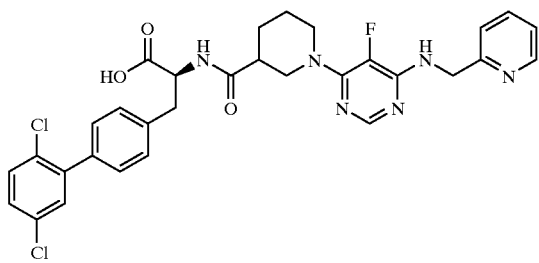

Step a 1.2 g of Wang polystyrene resin (Rapp-Polymere, Tübingen; loading 0.96 mmol/g) are swollen in dimethylformamide. The solvent is filtered off with suction and a solution of 957 mg of (2S)-3-(4-bromophenyl)-2-(9-fluorenylmethoxycarbonylamino)-propionic acid in 8 ml dimethylformamide is added. After shaking at room temperature for 15 minutes, the suspension is treated with 304 µl of pyridine and 478 mg of 2,6-dichlorobenzoyl chloride. It is shaken overnight at room temperature. The derivatized resin is then washed with dimethylformamide, methanol and dichloromethane. The derivatized resin is treated with 15 ml of a 20% strength piperidine solution in Dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane.

Step b

To a solution of 1.188 g of (3R,S)-N-(9-Fluorenylmethoxycarbonyl)piperidin-3-carboxylic acid (amino acid reagent) in 7 ml dimethylformamide 1.331 g O-(7-azabenzotriazol-1-yl)1,1,3,3-tetramethyluronium hexafluorophosphate and 616 µl diisopropylethylamine were added. After shaking the mixture for 15 minutes, the derivatized resin was treated with this solution for 4 hours at room temperature. The derivatized resin is then washed with dimethylformamide and tetrahydrofurane.

Step c

The derivatized resin is suspended in 7 ml of xylene, treated with 1.414 g of 2,5-dichlorobenzeneboronic acid (boronic acid reagent) and a solution of 1.571 g sodium carbonate in 7 ml of water and shaken for 5 minutes at room temperature. 217 mg of bis-(triphenylphosphane)-palladium (II) chloride and 162 mg of triphenylphosphane are then added and the mixture is stirred overnight at 85° C. The derivatized resin is then washed with tetrahydrofurane/water 1:1, 0.25 M aqueous hydrochloric acid, water, dimethylformamide, methanol, tetrahydrofurane and dichloromethane.

Step d

The derivatized resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane. The derivatized resin is treated with a solution of 400 µl of diisopropylethylamine in 12 ml dimethylformamide and a solution of 1.223 g of 4,5,6-trifluoropyrimidine in 12 ml dimethylformamide. It is shaken for 5 hours at room temperature. The derivatized resin is then washed with dimethylformamide.

Step e 986 mg of pyridin-2-yl-methylamine (amine reagent) in 12 ml dimethylformamide were added to the derivatized resin and the mixture is shaken overnight at room temperature. The derivatized resin is then washed with dimethylformamide, tetrahydrofurane, dichloromethane.

Step f

For removal of the product, the derivatized resin is shaken with 10 ml of trifluoroacetic acid/dichloromethane 1:1 for 1 hour, filtered off. The filtrate is concentrated in vacuo. 102 mg of the title compound are obtained.

Mass spectrometry (ESI): 624.

Retention time (HPLC):

$^1$H-NMR (400 MHz, CDCl$_3$) (diastereomer A=H, diastereomer B=H') δ=8.68–8.48 (2×d, 1H+1H', pyridinyl-H+pyridinyl-H'), 8.32 (m, 1H+1H', pyridinyl-H+pyridinyl-H'), 8.22 (s, 1H, pyrimidinyl-H), 8.02 (m, 1H+1H', pyridinyl-H+pyridinyl-H'), 8.01 (s, 1H', pyrimidinyl-H'), 7.76 (m, 1H+1H', pyridinyl-H+pyridinyl-H'), 7.43–7.21 (m, 7H+7H', aryl-H+aryl-H'), 5.10 (m, 2H, pyridinyl-CH$_2$), 5.06 (m, 2H, pyridinyl-CH$_2$), 4.80 (m, 1H+1H', H-2+H'-2), 3.92 (m, 2H+2H', NCHa+NCH'a+NCHb+NCH'b), 3.72 (m, 1H, NCHc), 3.63 (m, 1H', NCH'c), 3.44 (m, 1H, NCHd), 3.33 (dd, 1H, H-3a), 3.30 (m, 1H', NCH'd), 3.25 (dd, 1H', H'-3a), 3.04 (dd, 1H, H-3b), 3.02 (dd, 1H', H'3-b), 2.58 (m, 1H+1H', COCH+COCH'), 1.90–1.75 (m, 4H+4H', 2×CH$_2$+2×CH'$_2$).

Example 2.2

(2S)-3-(2',5'-dichloro[1,1'-biphenyl]-4-yl)-2-[({1-[5-fluoro-6-(1-piperazinyl)-4-pyrimidinyl]-3-piperidinyl}carbonyl)amino]propanoic acid

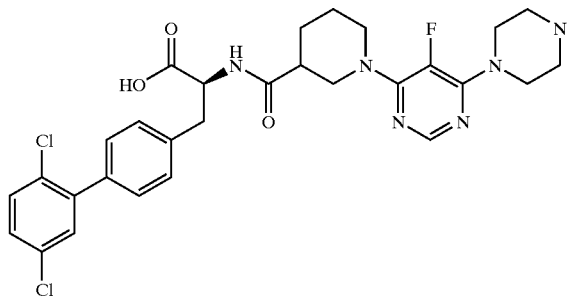

(2S)-3-(2',5'-dichloro[1,1'-biphenyl]-4-yl)-2-[({1-[5-fluoro-6-(piperazinyl)-4-pyrimidinyl]-3-piperidinyl}carbonyl)amino]propanoic acid is prepared according to the procedure of example 2.1, with the exception that piperazine is used as amine reagent instead pyridin-2-yl-methylamine.

Mass spectrometry (ESI): 602.

Retention time (HPLC): 8.0+8.4.

Example 2.3

(2S)-3-(2',5'-dichloro[1,1'-biphenyl]-4-yl)-2-[({1-[5-fluoro-6-(4-morpholinyl)-4-pyrimidinyl]-3-piperidinyl}carbonyl)amino]propanoic acid

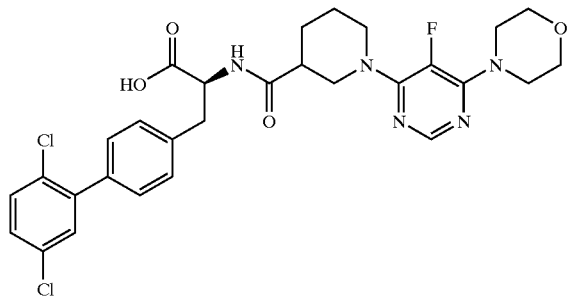

(2S)-3-(2',5'dichloro[1,1'-biphenyl]-4-yl)-2-[({1-[5-fluoro-6-(4-morpholinyl)-4-pyrimidinyl]-3-piperidinyl}carbonyl)amino]propanoic acid is prepared according to the procedure of example 1.1, with the exception that morpholine is used as amine reagent instead of pyridin-2-yl-methylamine.

Mass spectrometry (ESI): 603.

Retention time (HPLC): 9.4+9.6.

According to the procedure of example 2.1 following compounds shown in table 2 were prepared with the exception that optionally different boronic acids were used as boronic acid reagent instead of 2,5-dichlorobenzeneboronic acid and optionally different amines were used as amine reagent instead of pyridin-2-yl-methylamine.

TABLE 2

| structure | MW | MS-ESI | Rt (HPLC) [min] | example |
|---|---|---|---|---|
| 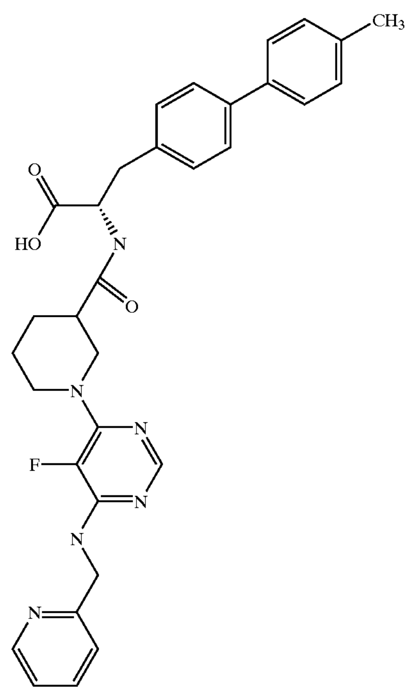 | 568.65 | 569 | 7.6 + 7.8 | 2.4 |

TABLE 2-continued
| structure | MW | MS-ESI | Rt (HPLC) [min] | example |
|---|---|---|---|---|
| 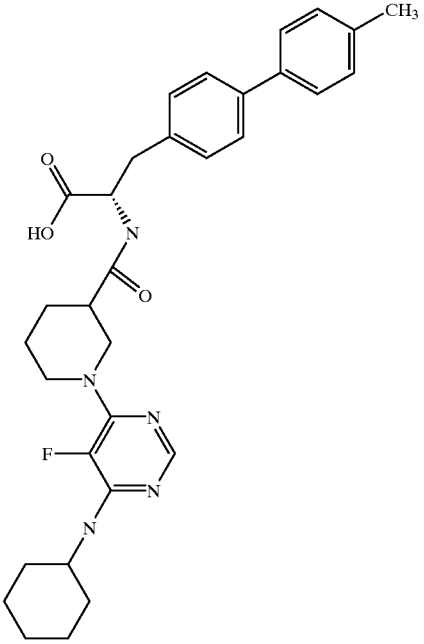 | 559.68 | 560 | 9.8 + 10.1 | 2.5 |
| 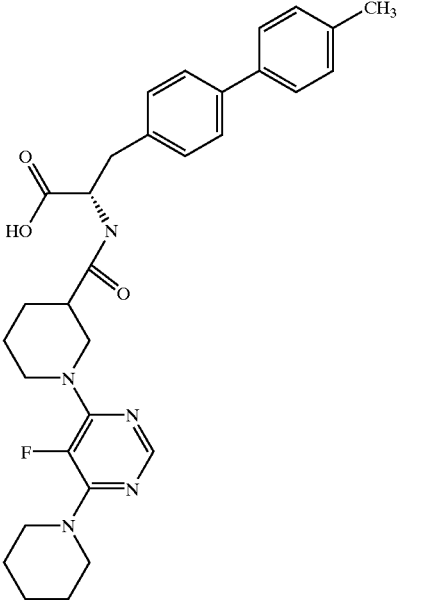 | 545.66 | 546 | 9.6 + 10.1 | 2.6 |

TABLE 2-continued
| structure | MW | MS-ESI | Rt (HPLC) [min] | example |
|---|---|---|---|---|
| 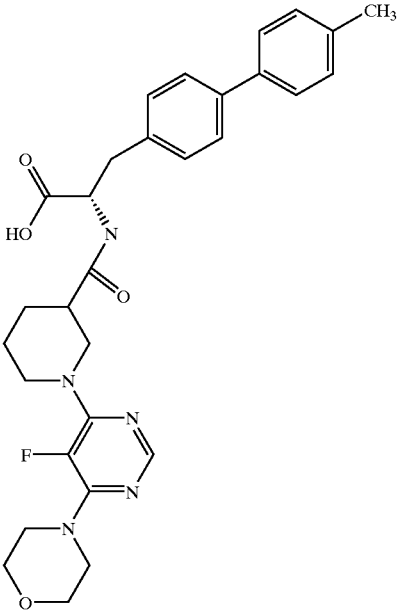 | 547.63 | 548 | 9.0 | 2.7 |
| 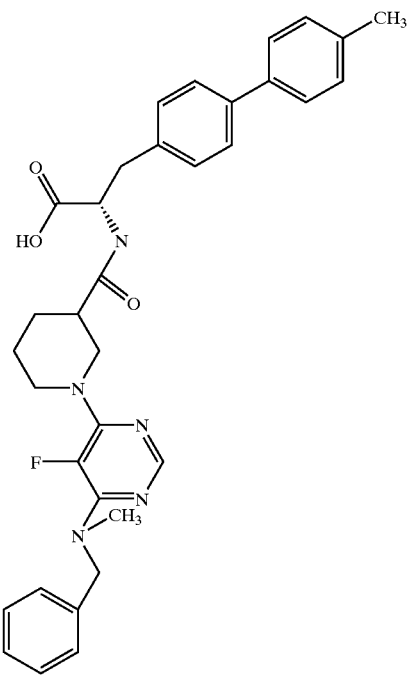 | 581.69 | 582 | 10.4 + 10.5 | 2.8 |

TABLE 2-continued
| structure | MW | MS-ESI | Rt (HPLC) [min] | example |
|---|---|---|---|---|
| 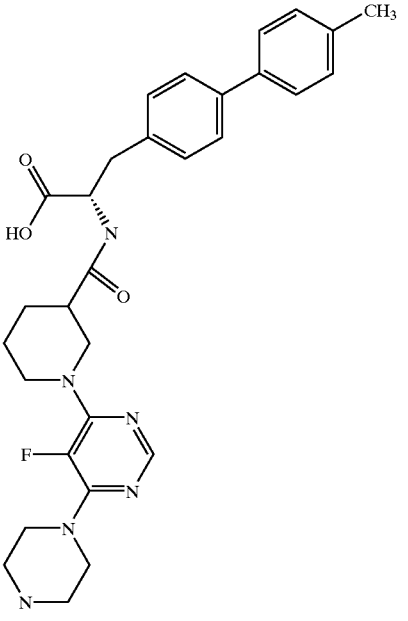 | 546.64 | 547 | 7.4 + 7.7 | 2.9 |
| 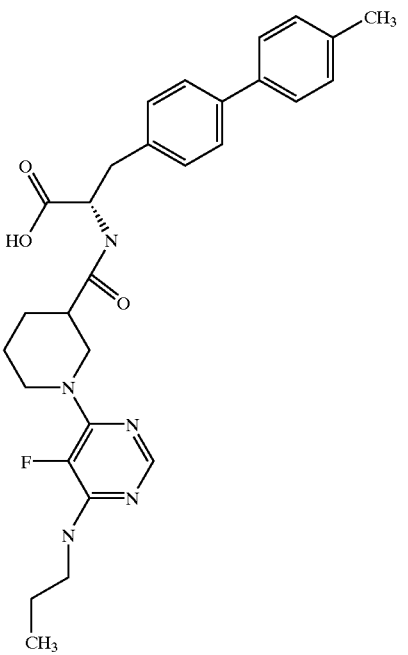 | 519.62 | 520 | 8.9 | 2.10 |

TABLE 2-continued
| structure | MW | MS-ESI | Rt (HPLC) [min] | example |
|---|---|---|---|---|
| 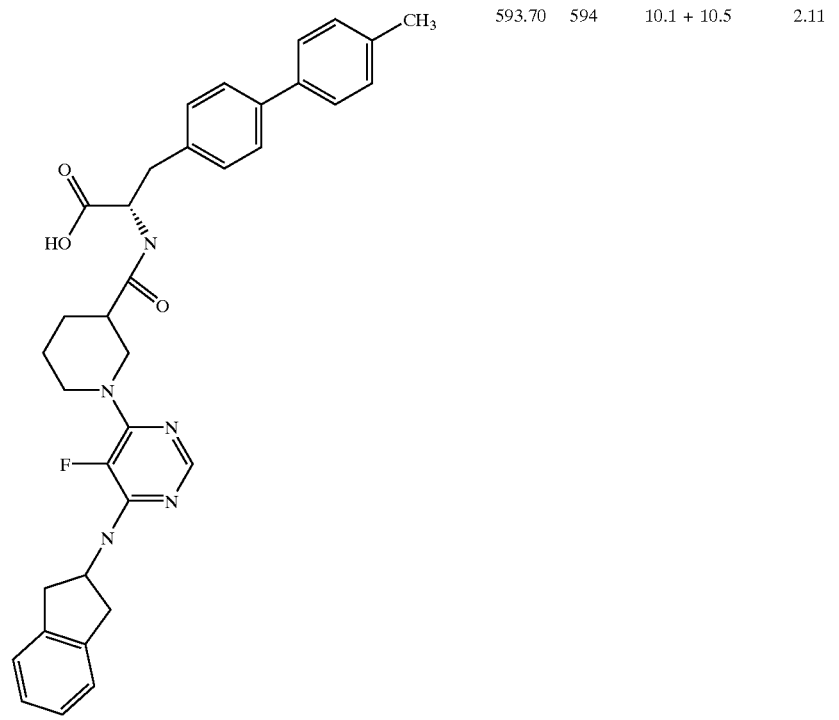 | 593.70 | 594 | 10.1 + 10.5 | 2.11 |
| 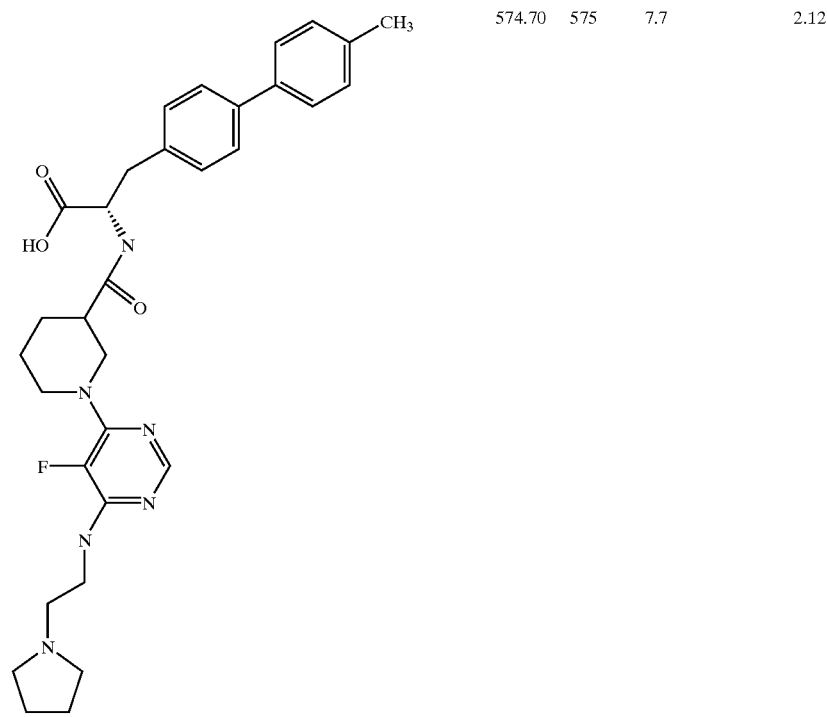 | 574.70 | 575 | 7.7 | 2.12 |

TABLE 2-continued
| structure | MW | MS-ESI | Rt (HPLC) [min] | example |
|---|---|---|---|---|
| 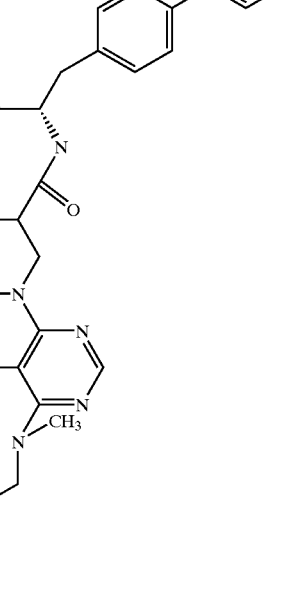 | 547.67 | 548 | 10.1 | 2.13 |
| 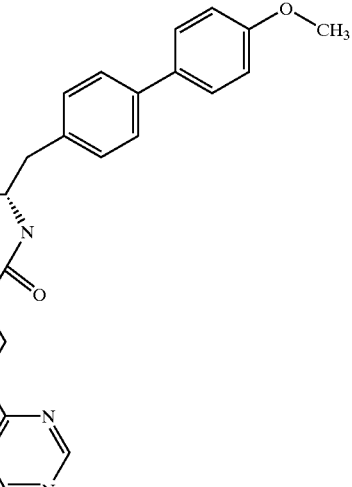 | 584.65 | 585 | 7.2 | 2.14 |

TABLE 2-continued
| structure | MW | MS-ESI | Rt (HPLC) [min] | example |
|---|---|---|---|---|
| 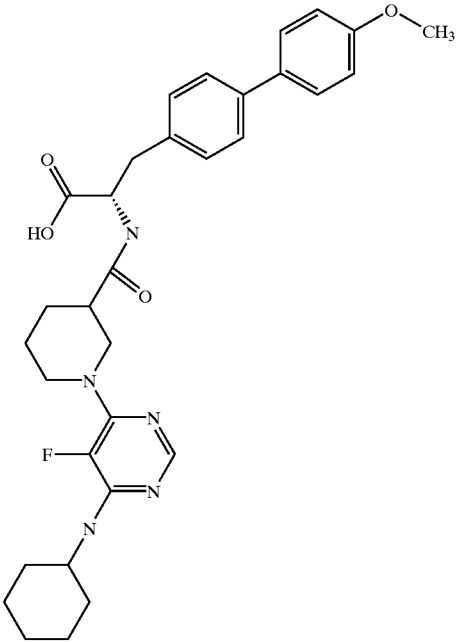 | 575.68 | 576 | 9.1 | 2.15 |
| 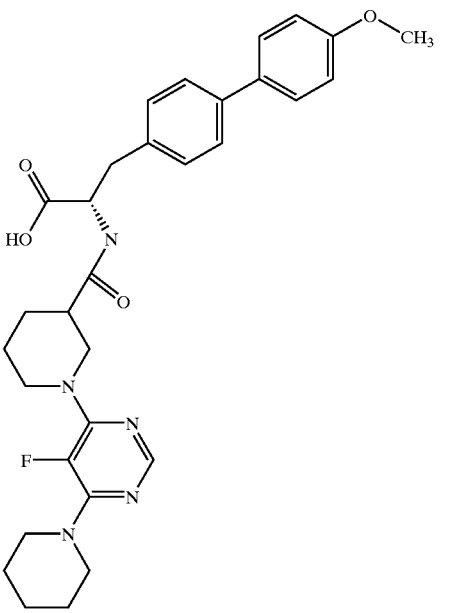 | 561.65 | 562 | 9.1 | 2.16 |

TABLE 2-continued
| structure | MW | MS-ESI | Rt (HPLC) [min] | example |
|---|---|---|---|---|
| 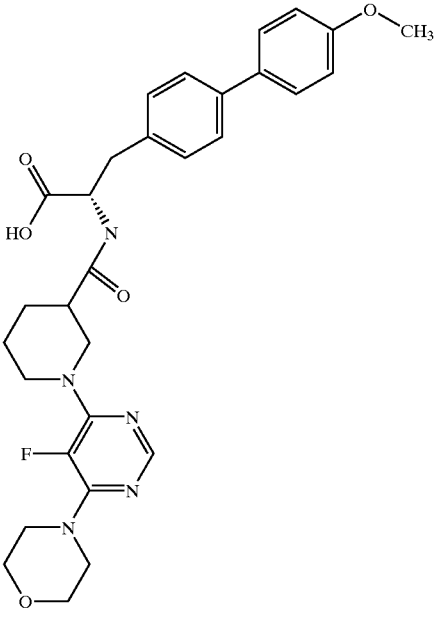 | 563.63 | 564 | 8.3 | 2.17 |
| 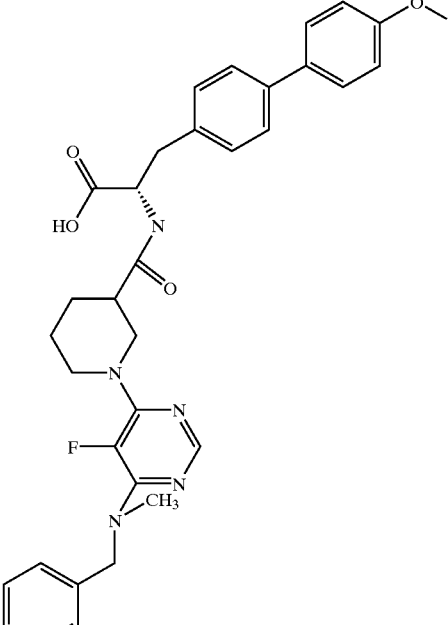 | 597.69 | 598 | 9.7 | 2.18 |

TABLE 2-continued
| structure | MW | MS-ESI | Rt (HPLC) [min] | example |
|---|---|---|---|---|
| 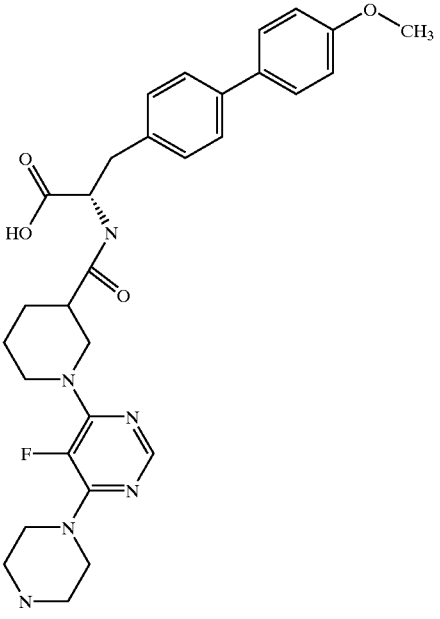 | 562.64 | 563 | 6.9 | 2.19 |
| 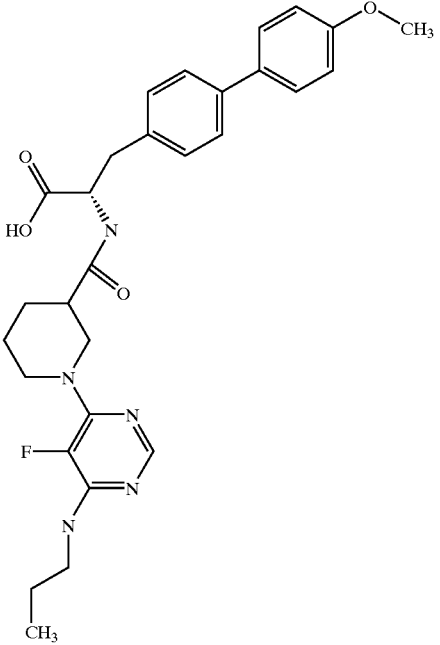 | 535.62 | 536 | 8.2 | 2.20 |

TABLE 2-continued

| structure | MW | MS-ESI | Rt (HPLC) [min] | example |
|---|---|---|---|---|
| 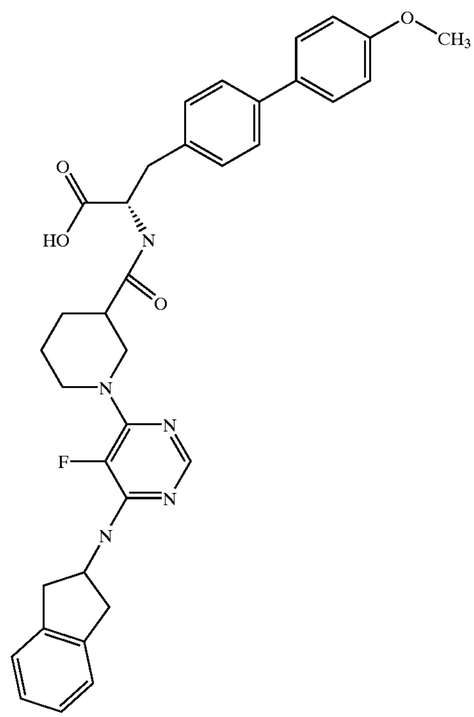 | 609.70 | 610 | 9.8 | 2.21 |
| 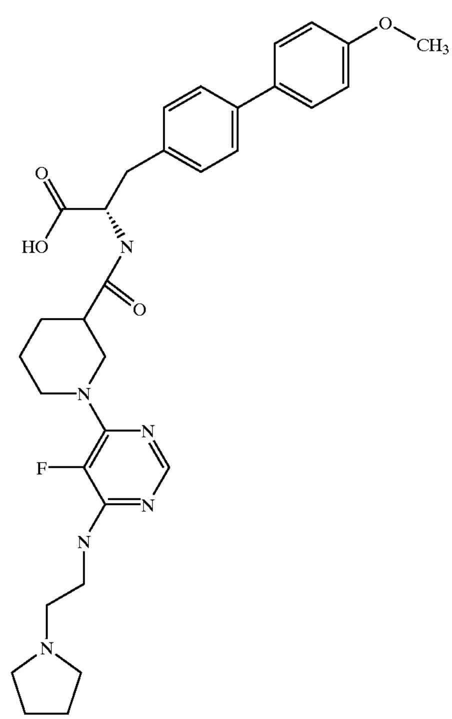 | 590.70 | 591 | 7.1 | 2.22 |

TABLE 2-continued
| structure | MW | MS-ESI | Rt (HPLC) [min] | example |
|---|---|---|---|---|
| 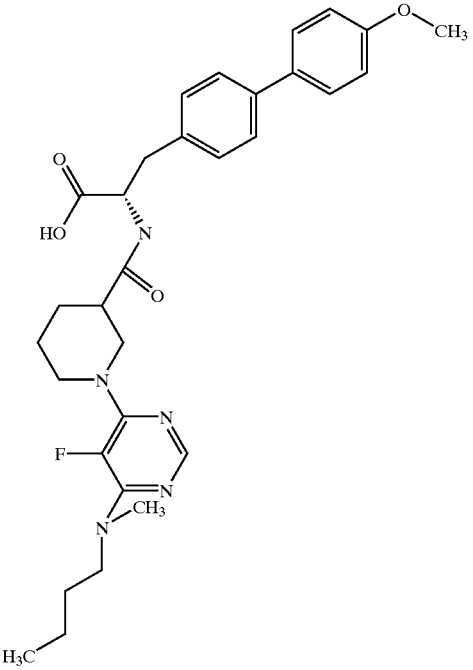 | 563.67 | 564 | 9.5 | 2.23 |
| 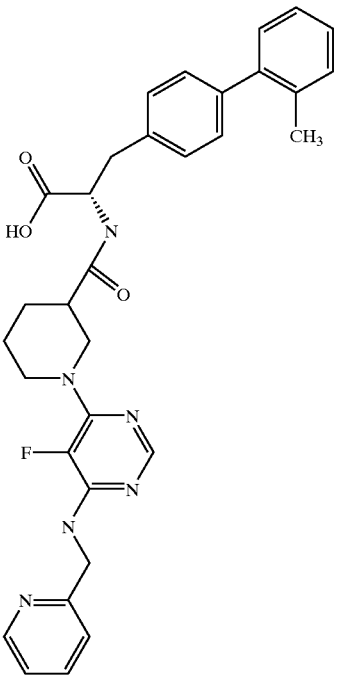 | 568.65 | 569 | 7.3 | 2.24 |

TABLE 2-continued

| structure | MW | MS-ESI | Rt (HPLC) [min] | example |
|---|---|---|---|---|
| 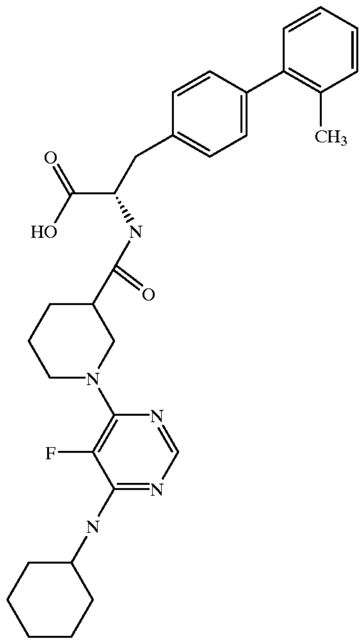 | 559.68 | 560 | 9.6 | 2.25 |
| 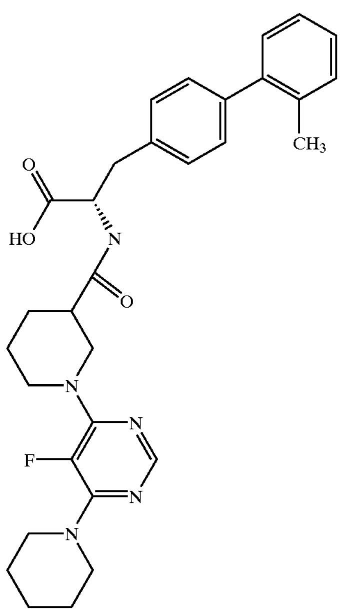 | 545.66 | 546 | 9.4 | 2.26 |

TABLE 2-continued

| structure | MW | MS-ESI | Rt (HPLC) [min] | example |
|---|---|---|---|---|
| 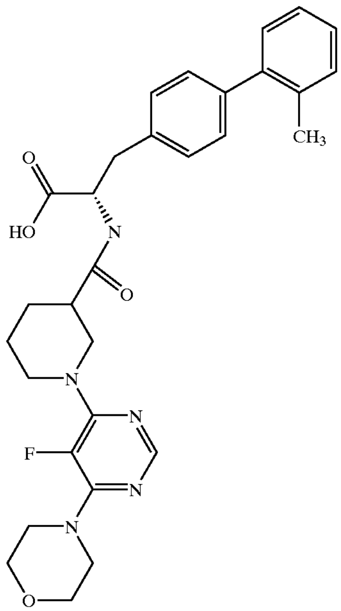 | 547.63 | 548 | 8.8 | 2.27 |
| 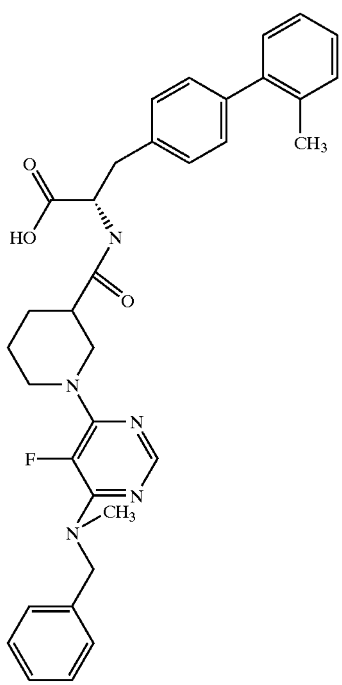 | 581.69 | 582 | 10.2 + 10.4 | 2.28 |

TABLE 2-continued
| structure | MW | MS-ESI | Rt (HPLC) [min] | example |
|---|---|---|---|---|
| 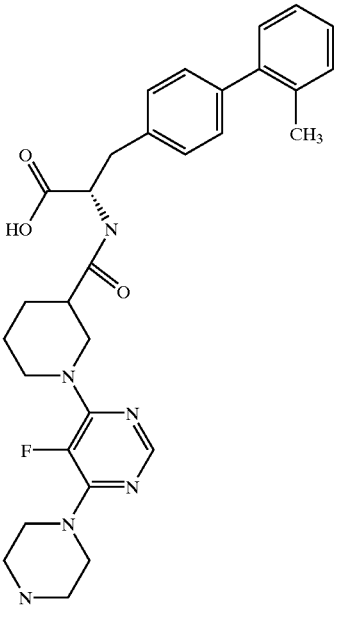 | 546.64 | 547 | 6.8 + 7.3 | 2.29 |
| 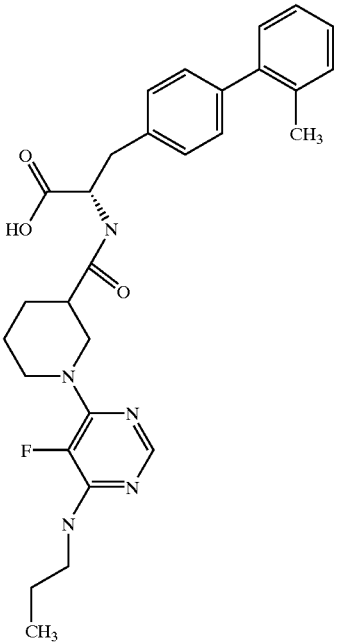 | 519.62 | 520 | 8.4 + 8.7 | 2.30 |

TABLE 2-continued
| structure | MW | MS-ESI | Rt (HPLC) [min] | example |
|---|---|---|---|---|
| 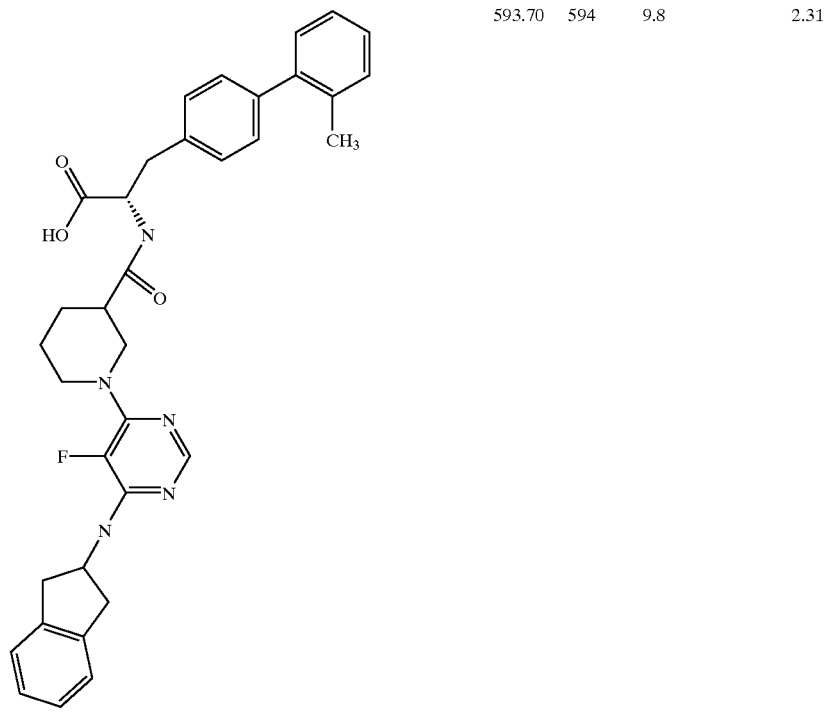 | 593.70 | 594 | 9.8 | 2.31 |
| 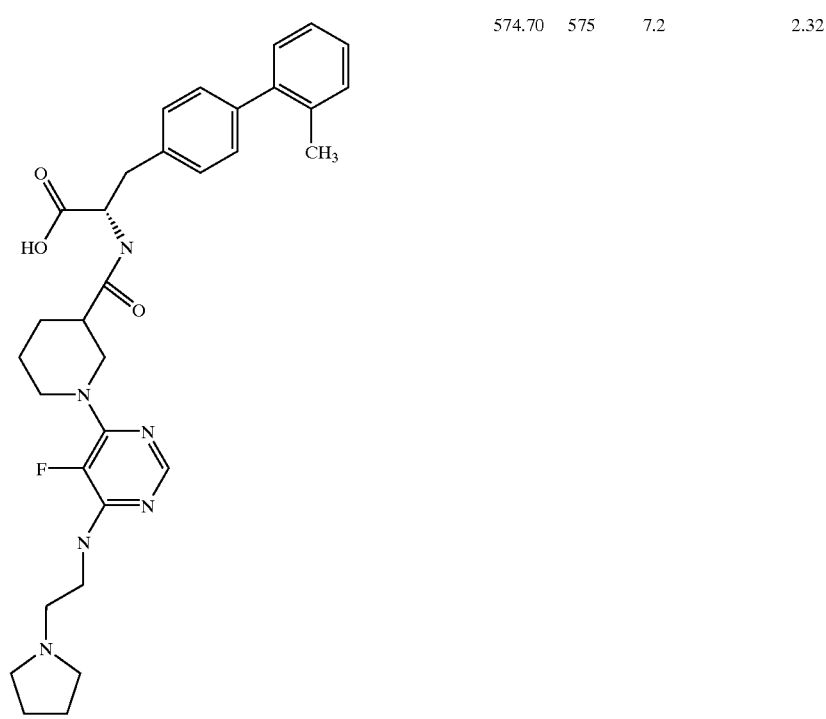 | 574.70 | 575 | 7.2 | 2.32 |

TABLE 2-continued
| structure | MW | MS-ESI | Rt (HPLC) [min] | example |
|---|---|---|---|---|
| 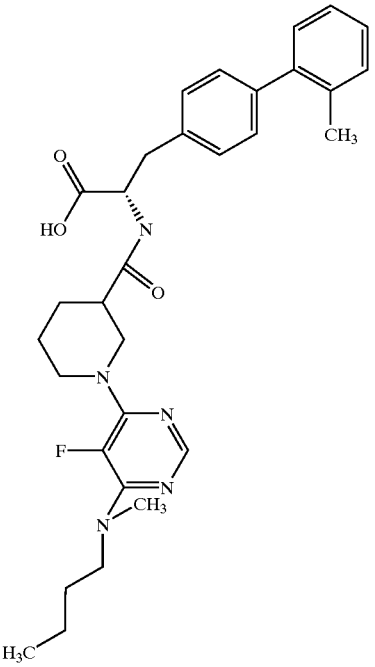 | 547.67 | 548 | 9.6 | 2.33 |
| 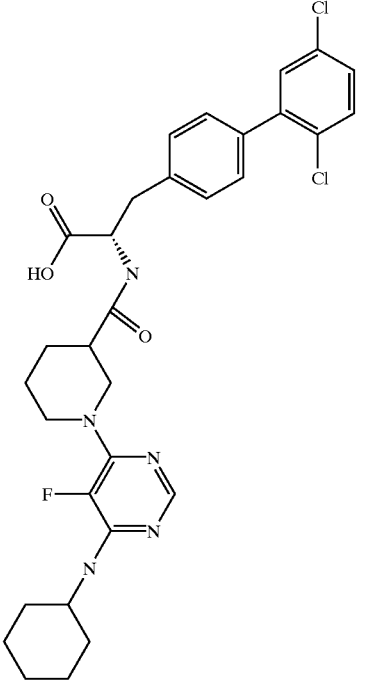 | 614.55 | 615 | 10.3 + 10.6 | 2.34 |

TABLE 2-continued
| structure | MW | MS-ESI | Rt (HPLC) [min] | example |
|---|---|---|---|---|
| 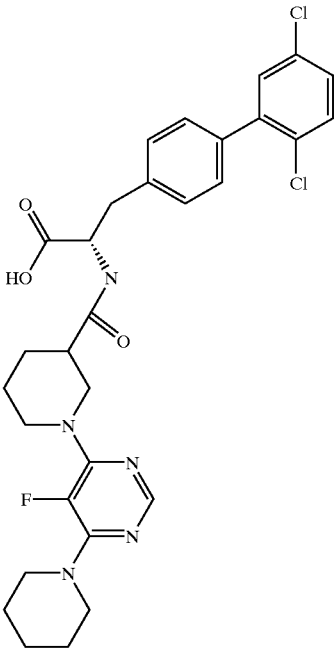 | 600.52 | 601 | 10.3 | 2.35 |
| 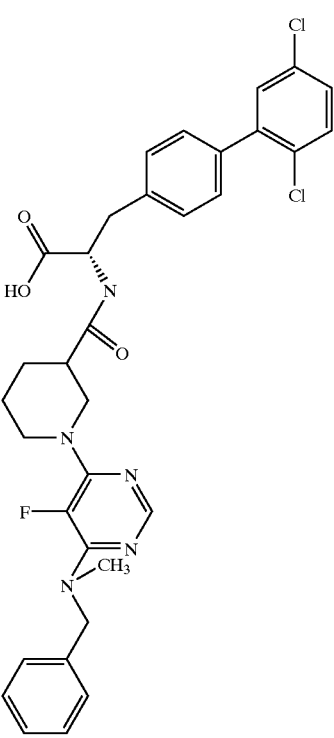 | 636.55 | 637 | 10.9 + 11.0 | 2.36 |

TABLE 2-continued
| structure | MW | MS-ESI | Rt (HPLC) [min] | example |
|---|---|---|---|---|
| 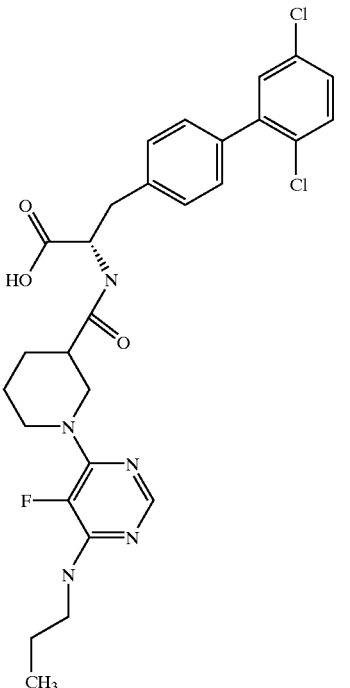 | 574.48 | 575 | 9.4 + 9.6 | 2.37 |
| 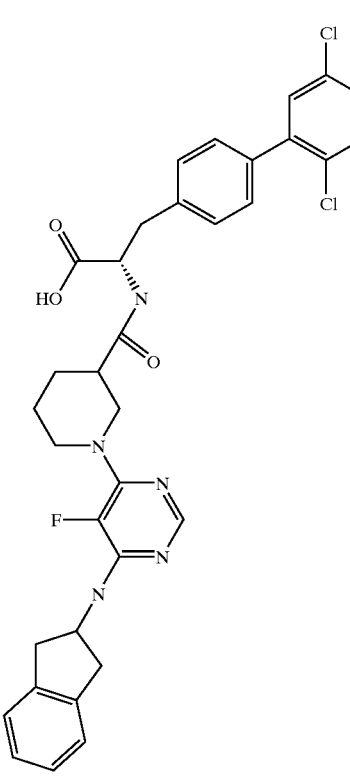 | 648.56 | 649 | 10.6 + 10.8 | 2.38 |

TABLE 2-continued
| structure | MW | MS-ESI | Rt (HPLC) [min] | example |
|---|---|---|---|---|
| 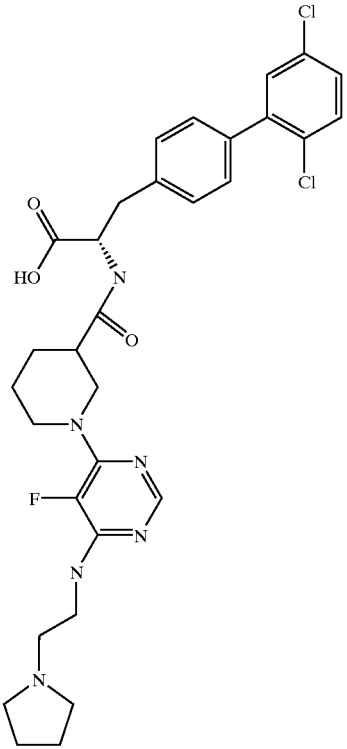 | 629.56 | 630 | 7.9 + 8.5 | 2.39 |
| 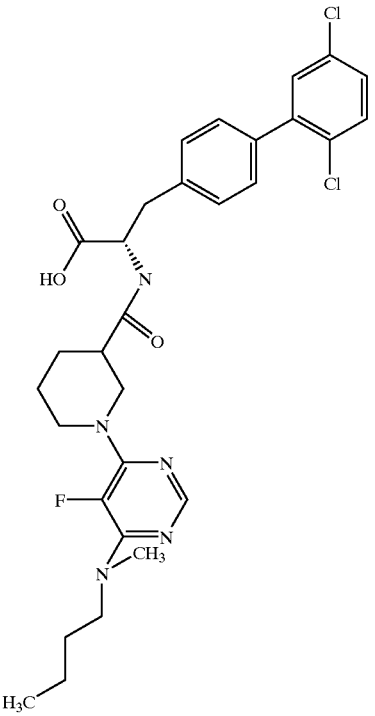 | 602.53 | 603 | 10.5 + 10.6 | 2.40 |

TABLE 2-continued
| structure | MW | MS-ESI | Rt (HPLC) [min] | example |
|---|---|---|---|---|
| 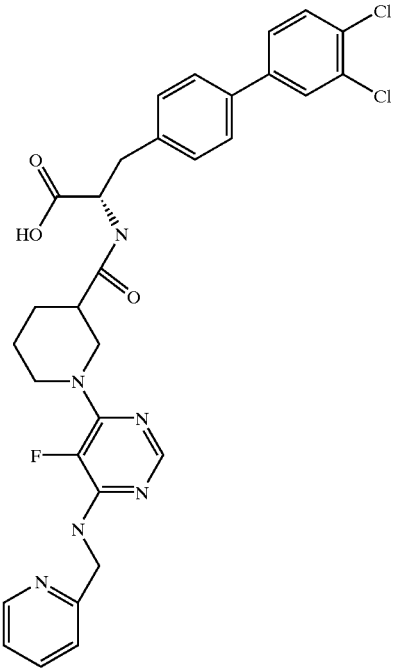 | 623.51 | 624 | 8.4 + 8.9 | 2.41 |
| 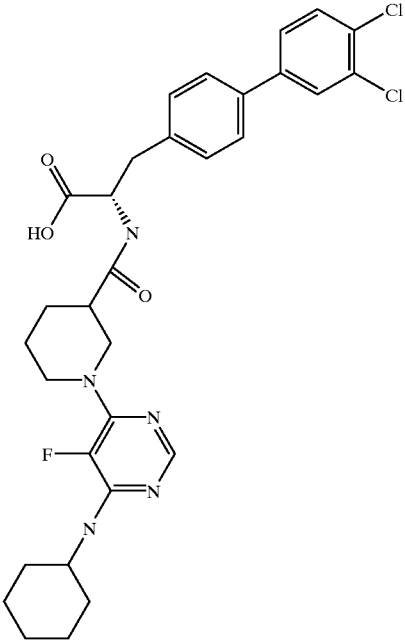 | 614.55 | 615 | 10.4 + 10.7 | 2.42 |

TABLE 2-continued

| structure | MW | MS-ESI | Rt (HPLC) [min] | example |
|---|---|---|---|---|
| 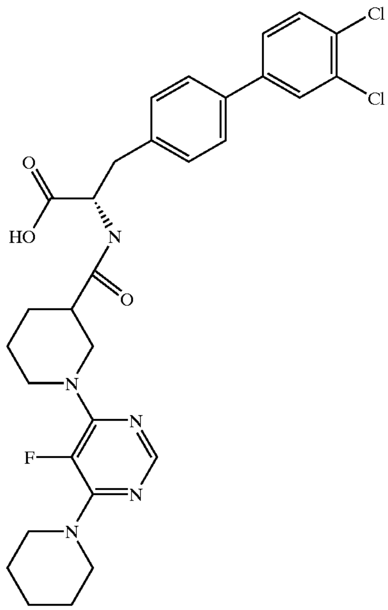 | 600.52 | 601 | 10.5 + 10.9 | 2.43 |
| 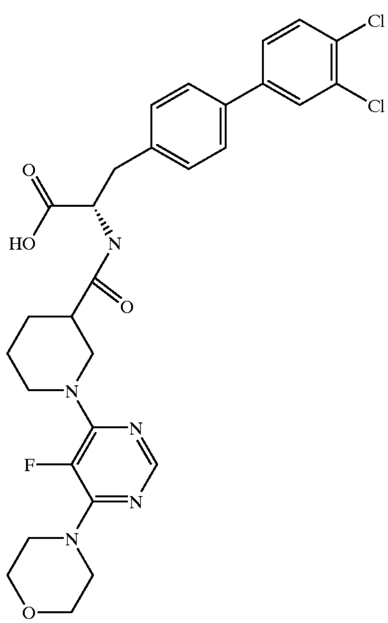 | 602.49 | 603 | 9.9 | 2.44 |

TABLE 2-continued
| structure | MW | MS-ESI | Rt (HPLC) [min] | example |
|---|---|---|---|---|
| 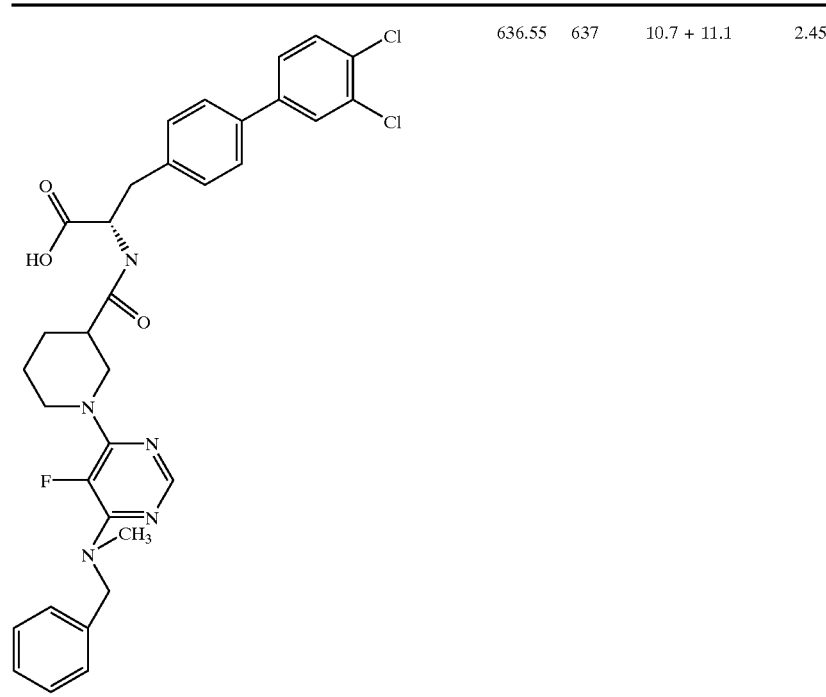 | 636.55 | 637 | 10.7 + 11.1 | 2.45 |
| 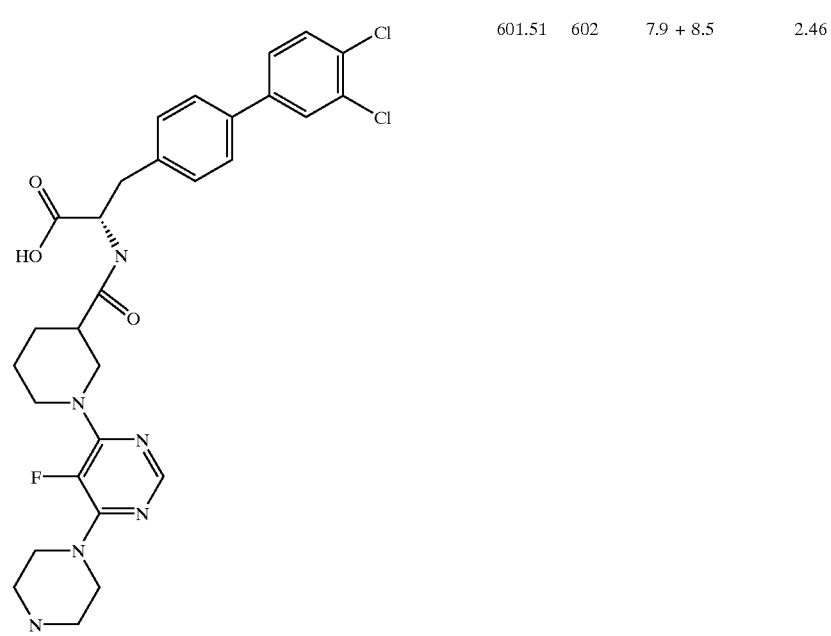 | 601.51 | 602 | 7.9 + 8.5 | 2.46 |

TABLE 2-continued
| structure | MW | MS-ESI | Rt (HPLC) [min] | example |
|---|---|---|---|---|
| 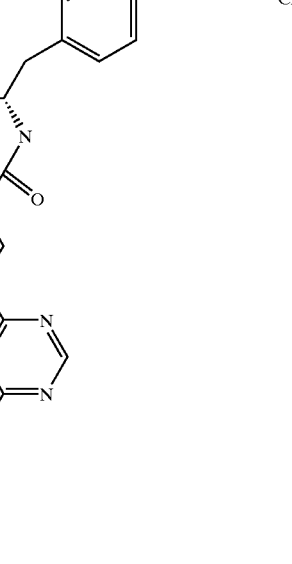 | 574.48 | 575 | 9.4 + 10.1 | 2.47 |
| 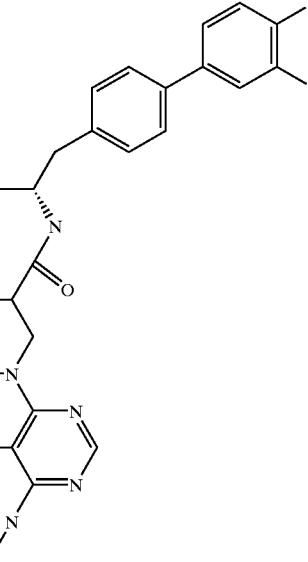 | 648.56 | 649 | 10.7 + 11.1 | 2.48 |

TABLE 2-continued
| structure | MW | MS-ESI | Rt (HPLC) [min] | example |
|---|---|---|---|---|
| 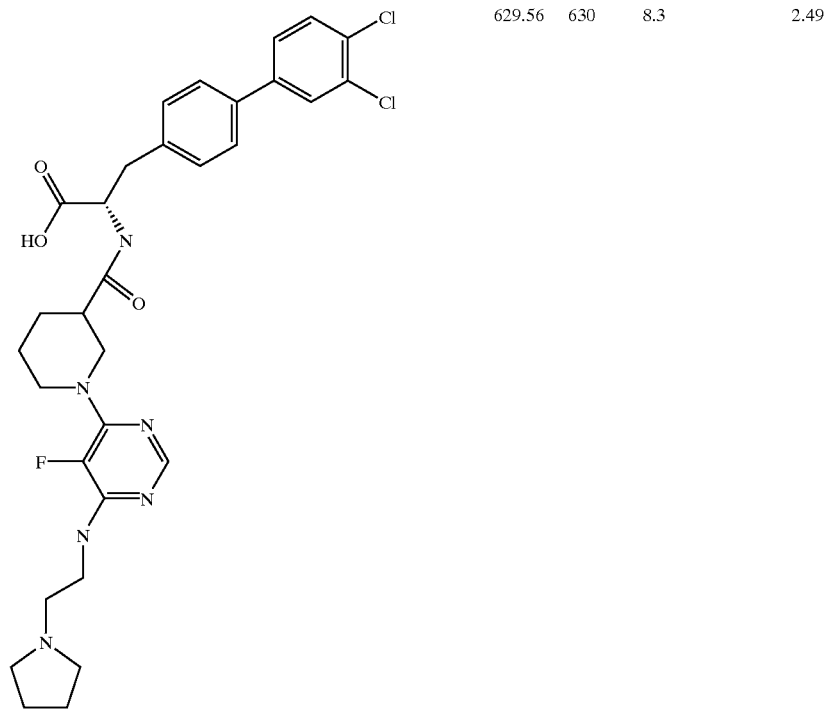 | 629.56 | 630 | 8.3 | 2.49 |
| 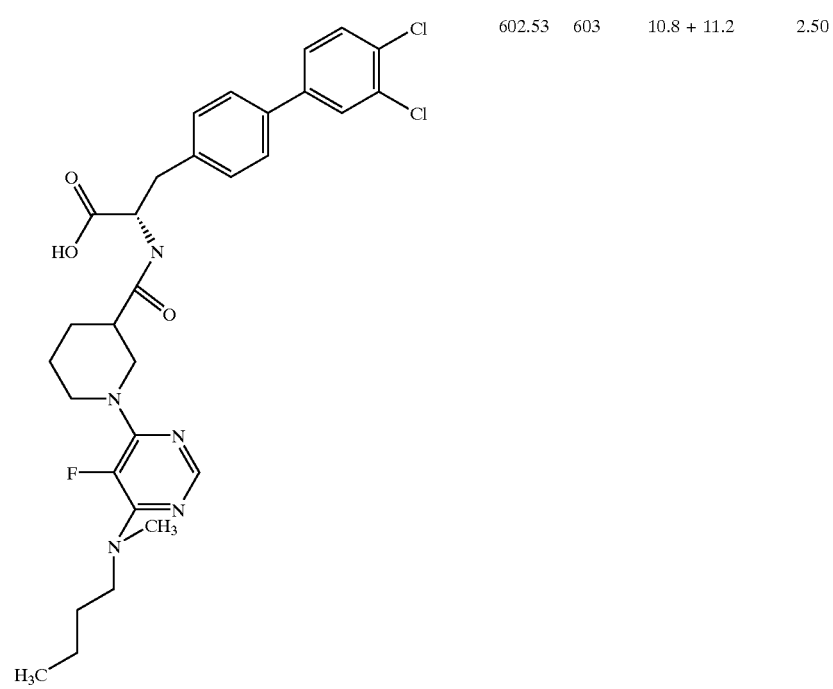 | 602.53 | 603 | 10.8 + 11.2 | 2.50 |

TABLE 2-continued
| structure | MW | MS-ESI | Rt (HPLC) [min] | example |
| --- | --- | --- | --- | --- |
| 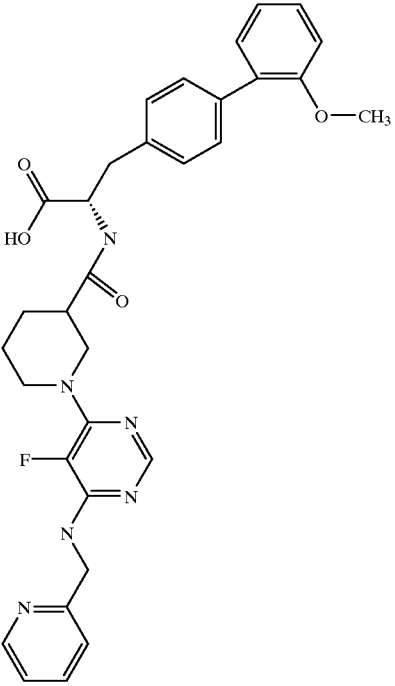 | 584.65 | 585 | 7.0 + 7.6 | 2.51 |
| 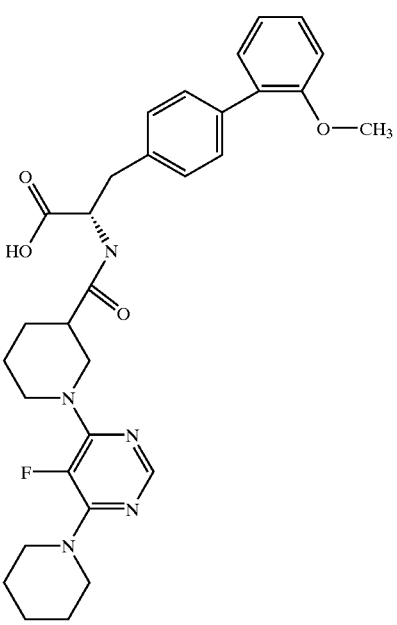 | 561.65 | 562 | 8.9 + 9.5 | 2.52 |

TABLE 2-continued
| structure | MW | MS-ESI | Rt (HPLC) [min] | example |
|---|---|---|---|---|
| 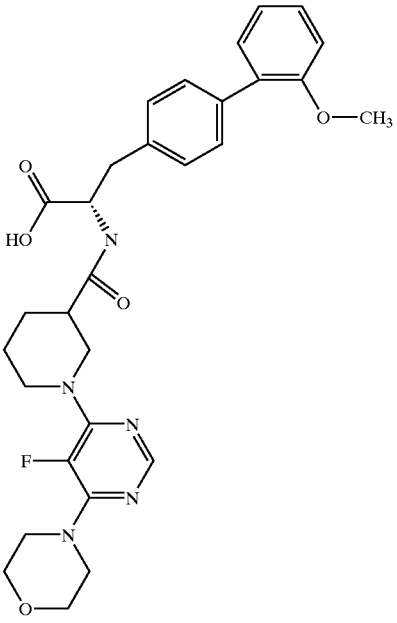 | 563.63 | 564 | 8.3 + 8.5 | 2.53 |
| 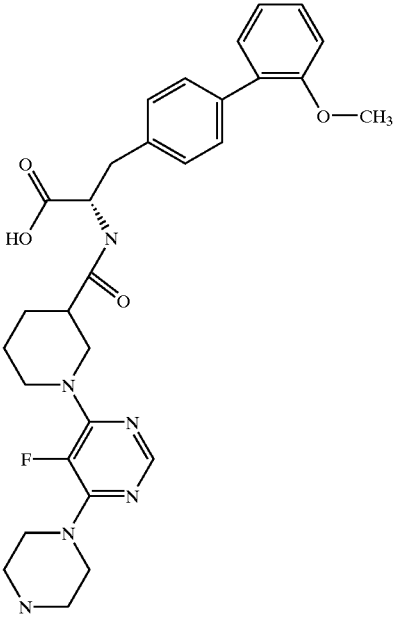 | 562.64 | 563 | 6.5 + 6.9 | 2.54 |

TABLE 2-continued
| structure | MW | MS-ESI | Rt (HPLC) [min] | example |
|---|---|---|---|---|
| 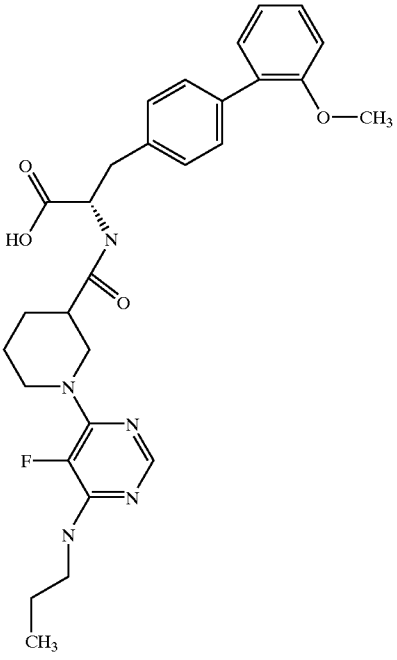 | 535.62 | 536 | 8.0 + 8.6 | 2.55 |
| 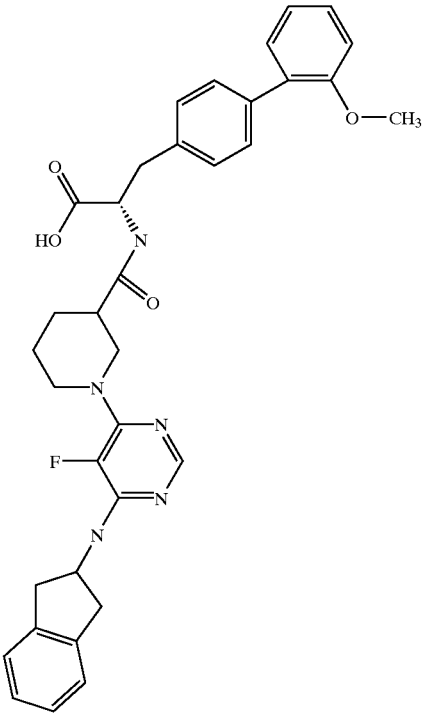 | 609.70 | 610 | 9.5 + 9.7 | 2.56 |

Example 3

General synthesis scheme (in case that A is single-foldly substituted by halogen):

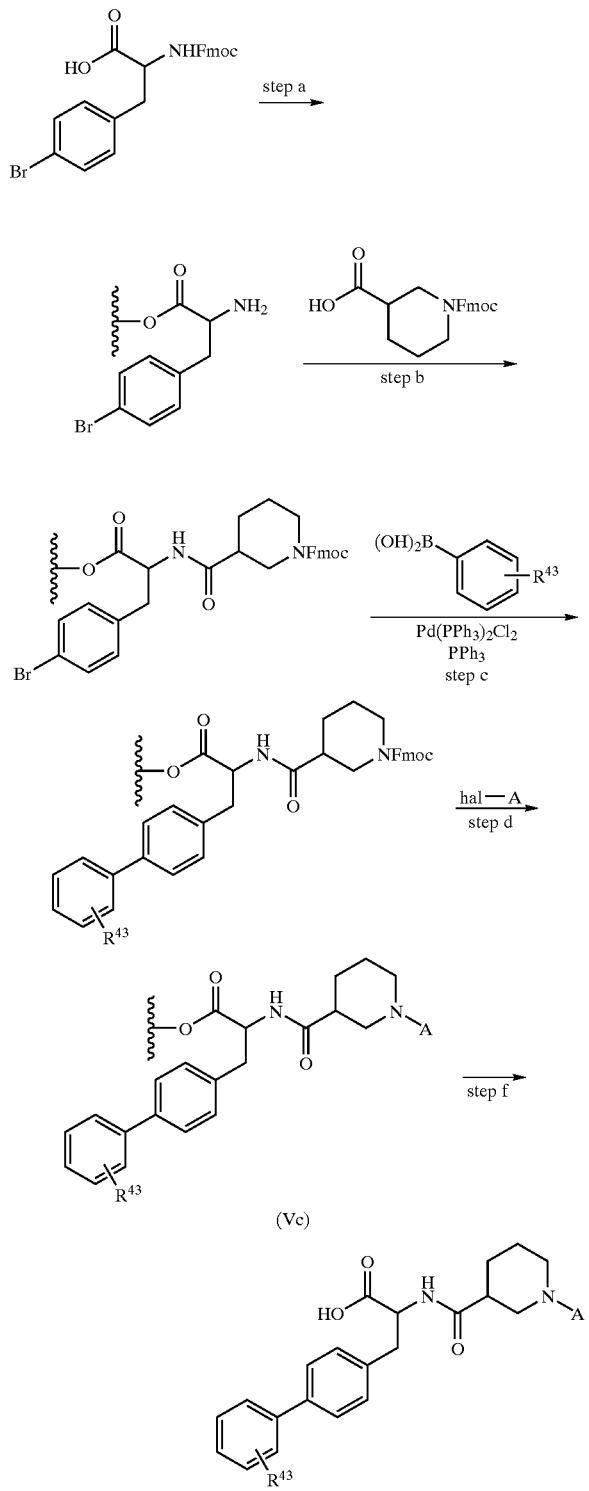

In the abovementioned scheme, hal stands for a leaving group such as a halogen, tosyl, mesyl or triflate.

Example 3.1

(2S)-3-(2',5'-dichloro[1,1'-biphenyl]-4-yl)-2-({[1-(2-pyrimidinyl)-3-piperidinyl]carbonyl}amino) propanoic acid

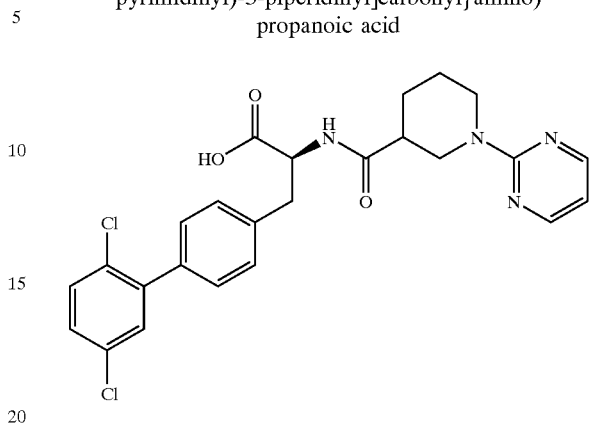

Step a 1.2 g of Wang polystyrene resin (Rapp-Polymere, Tübingen; loading 0.96 mmol/g) are swollen in dimethylformamide. The solvent is filtered off with suction and a solution of 957 mg of (2S)-3-(4-bromophenyl)-2-(9-fluorenylmethoxycarbonylamino)-propionic acid in 8 ml dimethylformamide is added. After shaking at room temperature for 15 minutes, the suspension is treated with 304 l of pyridine and 478 mg of 2,6-dichlorobenzoyl chloride. It is shaken overnight at room temperature. The resin is then washed with dimethylformamide , methanol and dichloromethane The resin is treated with 15 ml of a 20% strength piperidine solution in Dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane.

Step b

To a solution of 1.188 g of (3R,S)-N-(9-Fluorenylmethoxycarbonyl)-piperidin-3-carboxylic acid (amino acid reagent) in 7 ml dimethylformamide 1.331 g O-(7-azabenzotriazol-1-yl)1,1,3,3-tetramethyluronium hexafluorophosphate and 616 μl diisopropylethylamine were added. After shaking the mixture for 15 minutes, the resin was treated with this solution for 4 hours at room temperature. The resin is then washed with dimethylformamide and tetrahydrofurane.

Step c

The resin is suspended in 7 ml of xylene, treated with 1.414 g of 2,5-dichlorobenzeneboronic acid (boronic acid reagent) and a solution of 1.571 g sodium carbonate in 7 ml of water and shaken for 5 minutes at room temperature. 217 mg of bis-(triphenylphosphane)-palladium(II) chloride and 162 mg of triphenylphosphane are then added and the mixture is stirred overnight at 85° C. The resin is then washed with tetrahydrofurane/water 1:1, 0.25 M aqueous hydrochloric acid, water, dimethylformamide, methanol, tetrahydrofurane and dichloromethane.

Step d

The resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane. The resin is treated with a solution of 600 µl of diisopropylethylamine in 6 ml dimethylformamide and a solution of 1.956 g 2-chloropyrimidine (halogen-heterocycle reagent) in 6 ml dimethylformamide. It is shaken overnight at 85° C. (reaction conditions). The resin is then washed with dimethylformamide, methanol, tetrahydrofurane, dichloromethane.

Step f

For removal of the product, the resin is shaken with 10 ml of trifluoroacetic acid/dichloromethane 1:1 for 1 hour, filtered off. The filtrate is concentrated. 98 mg of the title compound are obtained.

Mass spectrometry (ESI): 500.

Retention time (HPLC): 9.9.

Example 3.2

(2S)-2-({[1-(1H-benzimidazol-2-yl)-3-piperidinyl]carbonyl}amino)-3-(2',5'-dichloro-[1,1'-biphenyl]-4-yl)propanoic acid

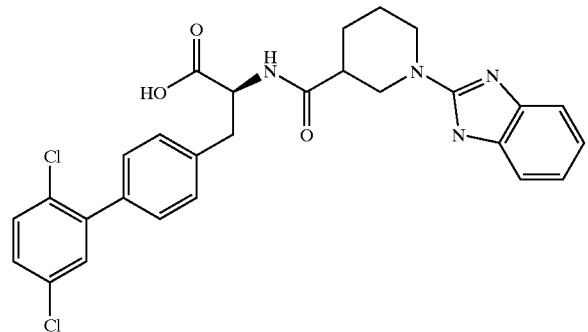

(S)-2-({[1-(1H-benzimidazol-2-yl)-3-piperidinyl]carbonyl}amino)-3-(2',5'-dichloro-[1,1'-biphenyl]-4-yl)propanoic acid is prepared according to the procedure of example 3.1, with the exception that 2-chloro-1H-benzimidazole is used as halogen-heterocycle reagent instead of 2-chloropyrimidine at 105° C. overnight (reaction conditions).

Mass spectrometry (ESI): 538.

Retention time (HPLC): 8.8+8.9.

Example 33

(2S)-3-(2',5'-dichloro[1,1'-biphenyl]yl)-2-({[1-(5-nitro-2-pyridinyl)-3-piperidinyl]carbonyl}amino)propanoic acid

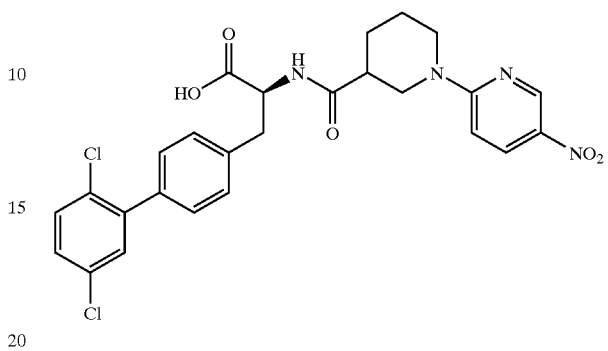

(2S)-3-(2',5'-dichloro[1,1'-biphenyl]-4-yl)-2-({[1-(5-nitro-2-pyridinyl)-3-piperidinyl]carbonyl}amino)propanoic acid is prepared according to the procedure of example 3.1, with the exception that 2-chloro-5-nitro-pyridine is used as halogen-heterocycle reagent instead of 2-chloropyrimidine.

Mass spectrometry (ESI): 544.

Retention time (HPLC): 10.9+11.2.

Example 4

General synthesis scheme:

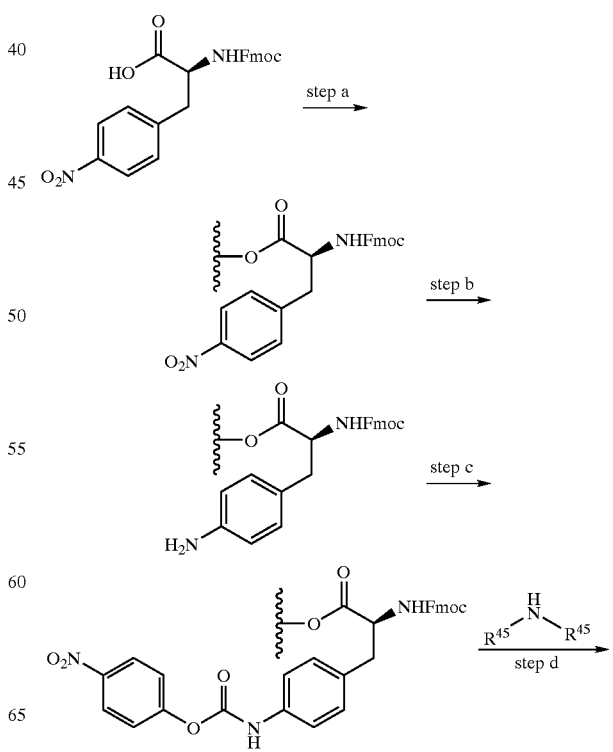

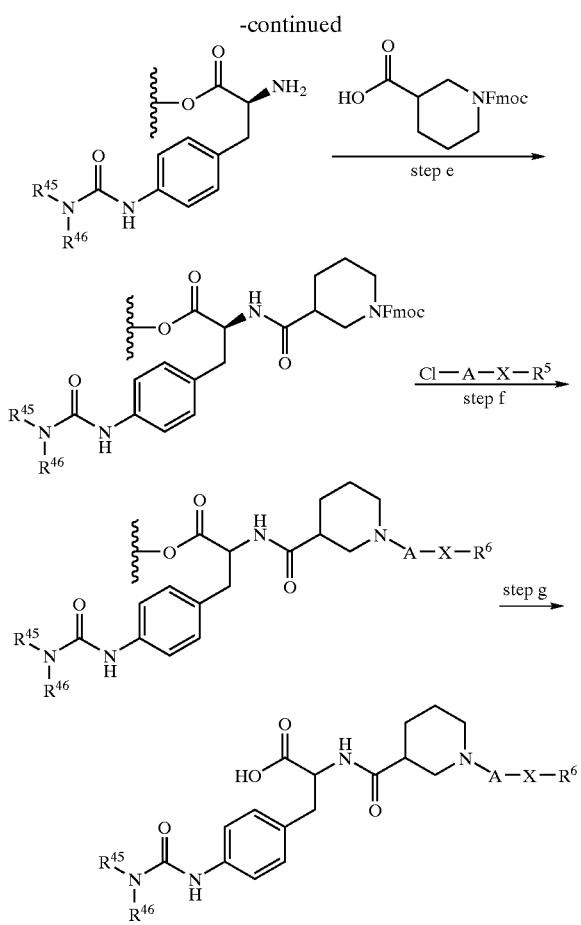

Example 4.1

N-{[1-(2-methoxybenzoyl)-3-piperidinyl]carbonyl}-4-{[(4methyl-1-piperazinyl)carbonyl]amino}-L-phenylalanine

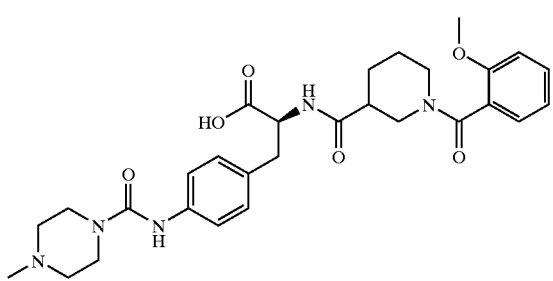

Step a 1.2 g of Wang polystyrene resin (Rapp-Polymere, Tübingen; loading 0.96 mmol/g) are swollen in dimethylformamide. The solvent is filtered off with suction and a solution of 920 mg of 4-nitro-L-phenylalanine in 8 ml dimethylformamide is added. After shaking at room temperature for 15 minutes, the suspension is treated with 304 µl of pyridine and 478 mg of 2,6-dichlorobenzoyl chloride. It is shaken overnight at room temperature. The resin is then washed with dimethylformamide, methanol and dichloromethane.

Step b

The resin is treated with a solution of 5.4 g of tin(II) chloride dihydrate in 12 ml of N-methylpyrrolidone and shaken overnight at room temperature. The resin is then washed with N-methylpyrrolidone, methanol, tetrahydrofuran and dichloromethane.

Step c

A solution of 577 µl diisopropylethylamine in 5 ml dichloromethane and 1.3 g 4-nitrophenylchloroformic acid ester in 5 ml tetrahydrofuran is subsequently given to the resin. After shaking at room temperature for 45 minutes, it is washed with tetrahydrofuran and N-methylpyrrolidone.

Step d

A solution of 774 mg of N-methylpiperazine (amine reagent) and 1.3 ml of diisopropylethylamine in 6 ml N-methylpyrrolidone is added to the rest After shaking for 2 h, the resin is washed with dimethylformamide, methanol, tetrahydrofuran and dichloromethane.

Step e

A solution of 867 mg O-7-azabenzotriazol-1-yl)1,1,3,3-tetramethyluronium hexafluorophosphate in 5.7 ml and 397 µl diisopropylethylamine were added to a solution of 801 mg of (3R,S)-N-(9-Fluorenylmethoxycarbonyl)-piperidin-3-carboxylic acid in 5.7 ml dimethylformamide. After shaking the mixture for 15 minutes, the resin was treated with this solution for 4 hours at room temperature. The resin is then washed with dimethylformamide and tetrahydrofuran.

Step f

The derivatized resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofurane. The derivatized resin is treated with a solution of 1.6 ml of diisopropylethylamine in 12 ml tetrahydrofurane and a solution of 1.361 g of 2-methoxybenzoylchloride (acylating/sulfonylating/carbamoylating reagent) in 12 ml tetrahydrofurane. It is shaken overnight at room temperature. The derivatized resin is then washed with dimethylformamide, methanol, tetrahydrofurane and dichloromethane.

Step g

For removal of the product, the derivatized resin is shaken with 10 ml of trifluoroacetic acid/dichloromethane 1:1 for 1 hour, filtered off. The filtrate is concentrated in vacuo and purified on silica gel. 93 mg of the title compound are obtained.

Mass spectrometry (ESI): 552.

Retention time (HPLC): 4.5.

TABLE 3

| structure | MW | MS-ESI | Rt (HPLC) [min] | example |
|---|---|---|---|---|
| 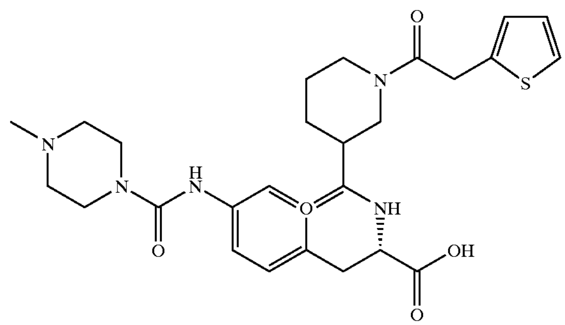 | 541.67 | 542 | 1.6 | 4.2 |
| 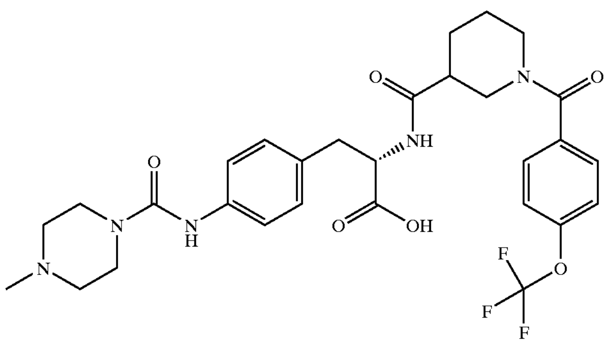 | 605.62 | 606 | 2.0 | 4.3 |
| 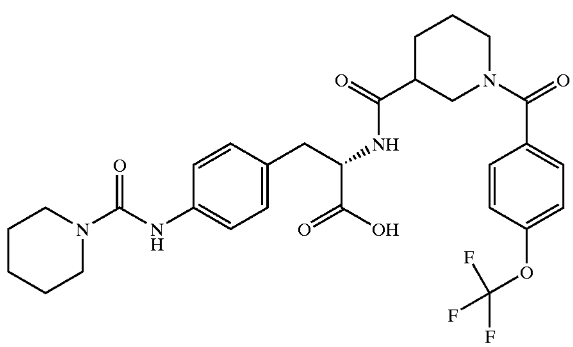 | 590.60 | 591 | 2.9 | 4.4 |
| 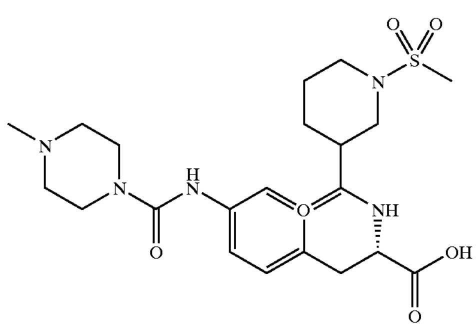 | 495.60 | 496 | 0.3 | 4.5 |

TABLE 3-continued

| structure | MW | MS-ESI | Rt (HPLC) [min] | example |
|---|---|---|---|---|
| 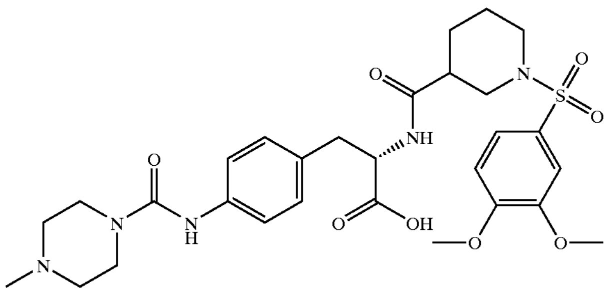 | 617.73 | 618 | 1.8 | 4.6 |
| 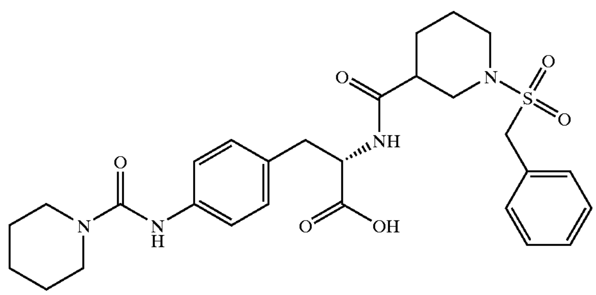 | 556.69 | 557 | 2.8 | 4.7 |
| 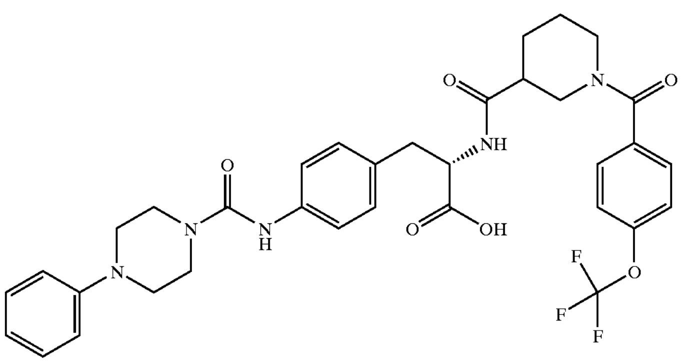 | 667.69 | 668 | 3.1 | 4.8 |
| 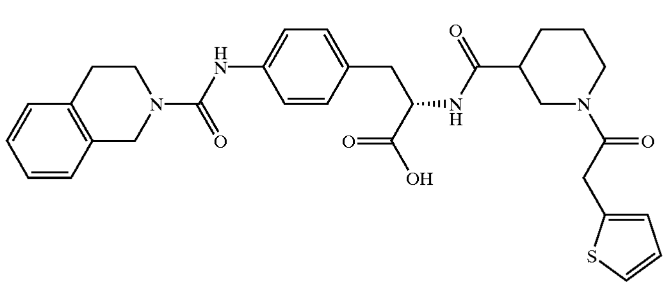 | 574.70 | 575 | 2.8 | 4.9 |

TABLE 3-continued
| structure | MW | MS-ESI | Rt (HPLC) [min] | example |
|---|---|---|---|---|
| 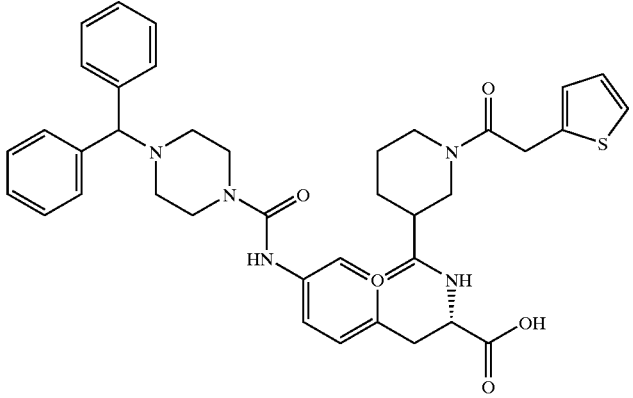 | 693.87 | 694 | 2.6 | 4.10 |
| 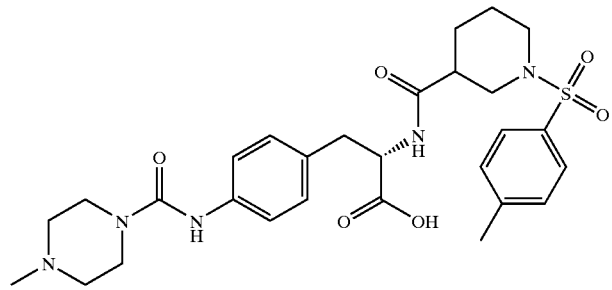 | 571.70 | 572 | 2.0 | 4.11 |
| 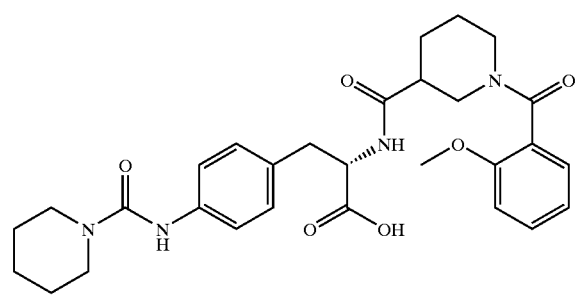 | 536.63 | 537 | 2.6 | 4.12 |
| 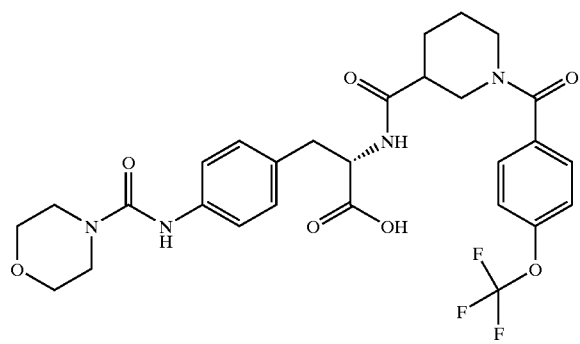 | 592.58 | 593 | 2.6 | 4.13 |

TABLE 3-continued

| structure | MW | MS-ESI | Rt (HPLC) [min] | example |
|---|---|---|---|---|
| 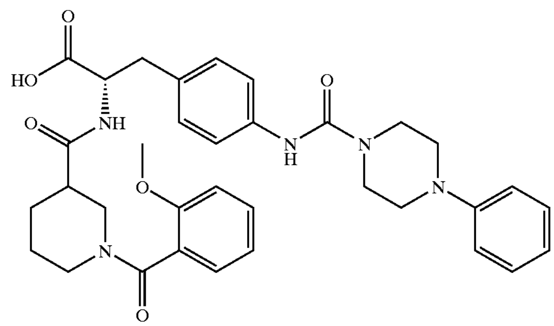 | 613.72 | 614 | 2.8 | 4.14 |
| 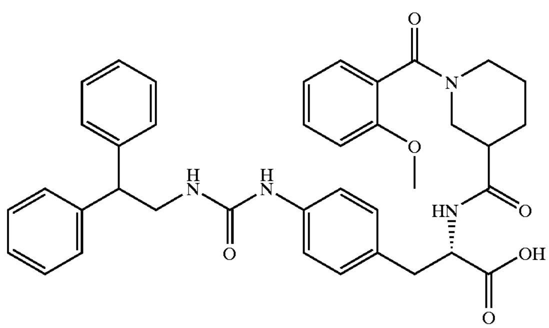 | 648.77 | 649 | 3.0 | 4.15 |
| 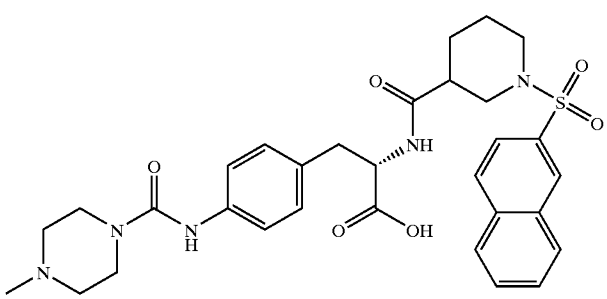 | 607.73 | 608 | 2.2 | 4.16 |
| 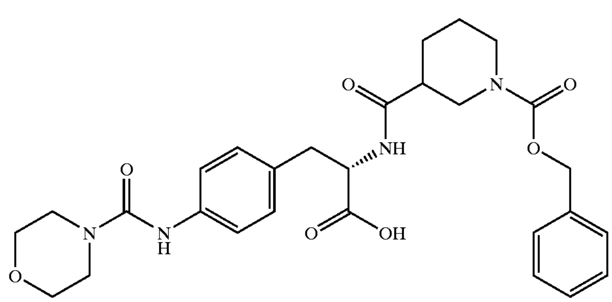 | 538.61 | 539 | 2.6 | 4.17 |

TABLE 3-continued
| structure | MW | MS-ESI | Rt (HPLC) [min] | example |
|---|---|---|---|---|
| 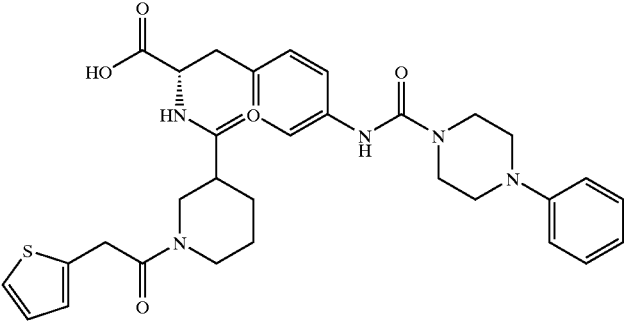 | 603.75 | 604 | 2.8 | 4.18 |
| 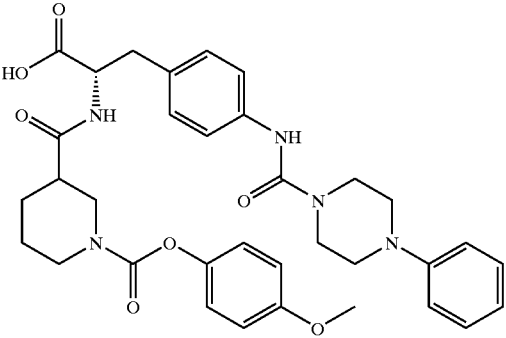 | 629.72 | 630 | 3.0 | 4.19 |
| 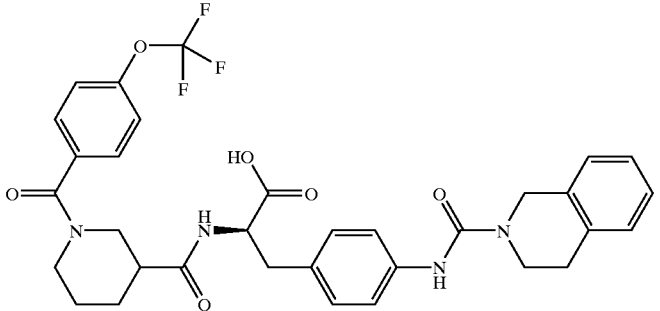 | 638.65 | 639 | 3.1 | 4.20 |
| 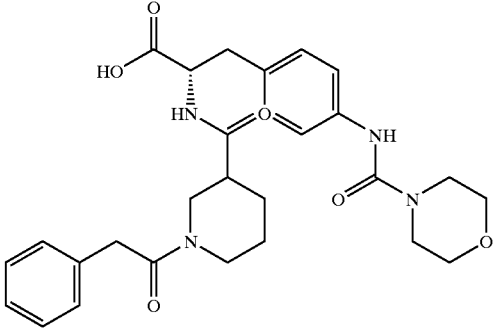 | 522.61 | 523 | 2.3 | 4.21 |

TABLE 3-continued

| structure | MW | MS-ESI | Rt (HPLC) [min] | example |
|---|---|---|---|---|
| 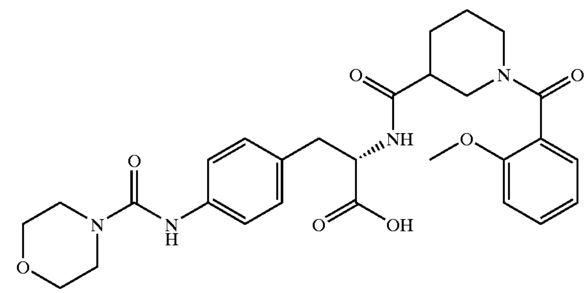 | 538.61 | 539 | 2.2 | 4.22 |
| 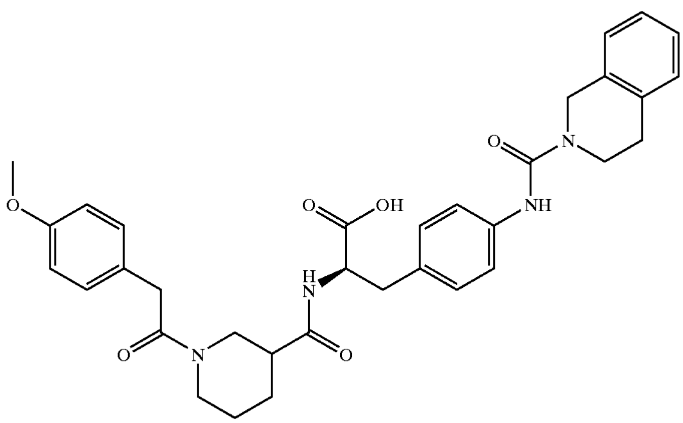 | 598.71 | 599 | 2.8 | 4.23 |
| 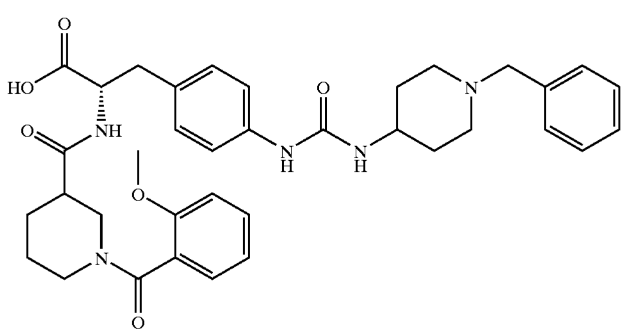 | 641.77 | 642 | 2.0 | 4.24 |
| 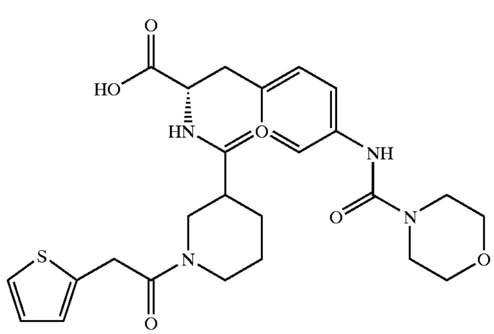 | 528.63 | 529 | 2.3 | 4.25 |

TABLE 3-continued

| structure | MW | MS-ESI | Rt (HPLC) [min] | example |
|---|---|---|---|---|
| 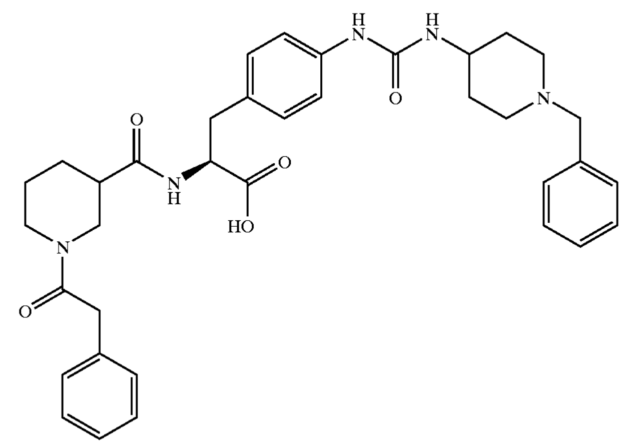 | 625.77 | 626 | 2.0 | 4.26 |
| 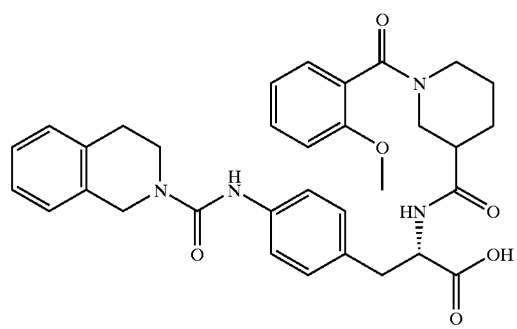 | 584.68 | 585 | 2.8 | 4.27 |
| 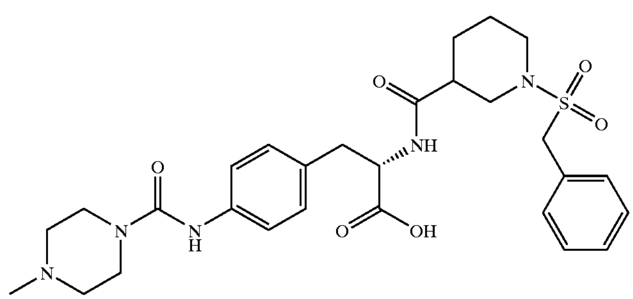 | 571.70 | 572 | 1.8 | 4.28 |
| 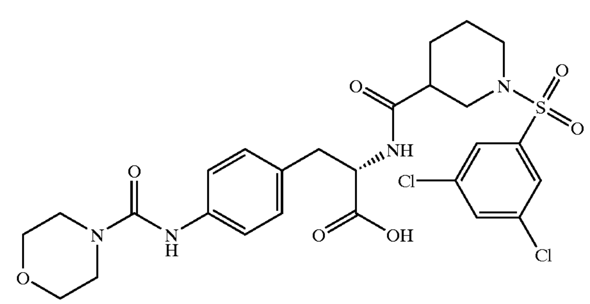 | 613.52 | 613 | 2.8 | 4.29 |

TABLE 3-continued
| structure | MW | MS-ESI | Rt (HPLC) [min] | example |
|---|---|---|---|---|
| 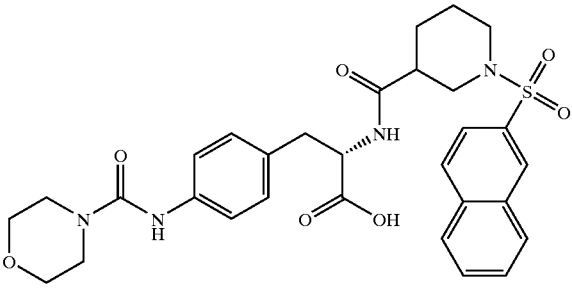 | 594.69 | 595 | 2.7 | 4.30 |
| 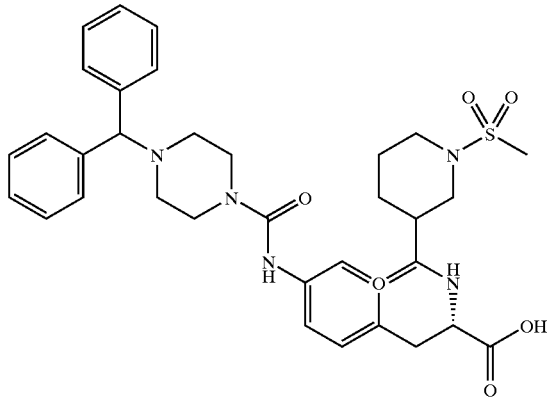 | 647.80 | 648 | 2.4 | 4.31 |
| 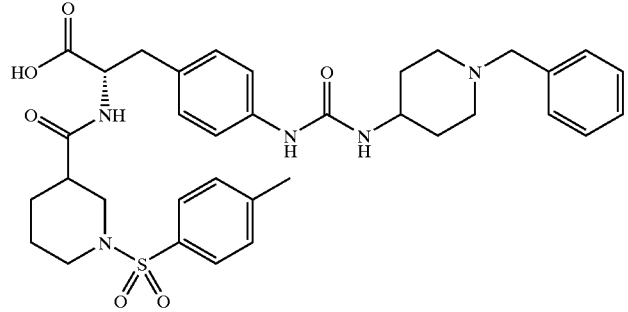 | 661.83 | 662 | 2.2 | 4.32 |
| 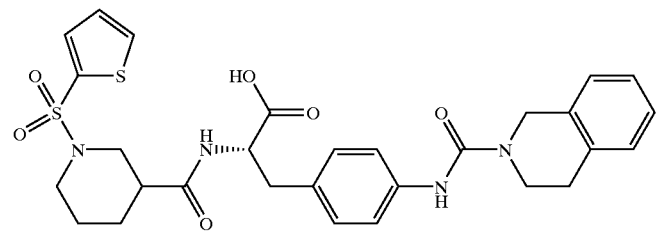 | 596.73 | 597 | 2.9 | 4.33 |

TABLE 3-continued
| structure | MW | MS-ESI | Rt (HPLC) [min] | example |
|---|---|---|---|---|
| 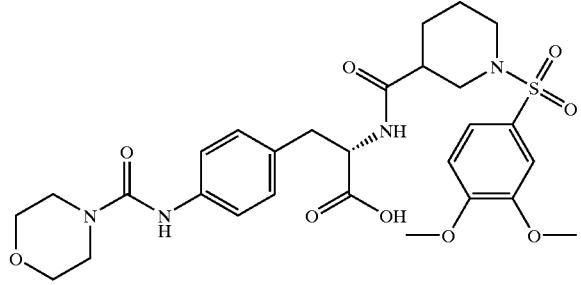 | 604.68 | 605 | 2.4 | 4.34 |
| 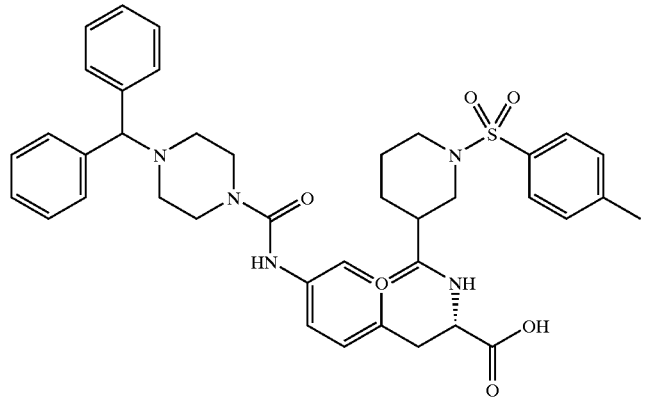 | 723.90 | 724 | 2.8 | 4.35 |
| 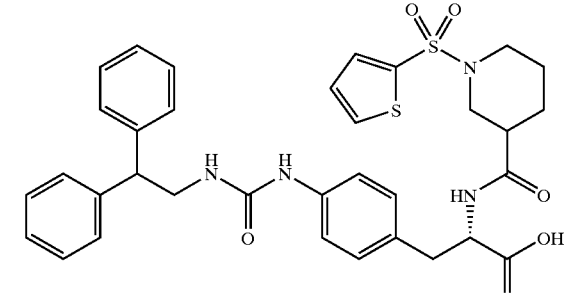 | 660.82 | 661 | 3.1 | 4.36 |
| 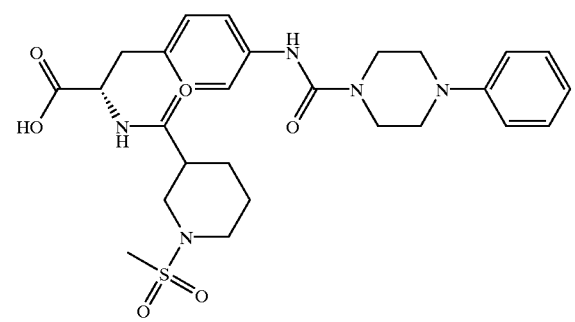 | 557.67 | 558 | 2.6 | 4.37 |

TABLE 3-continued
| structure | MW | MS-ESI | Rt (HPLC) [min] | example |
|---|---|---|---|---|
| 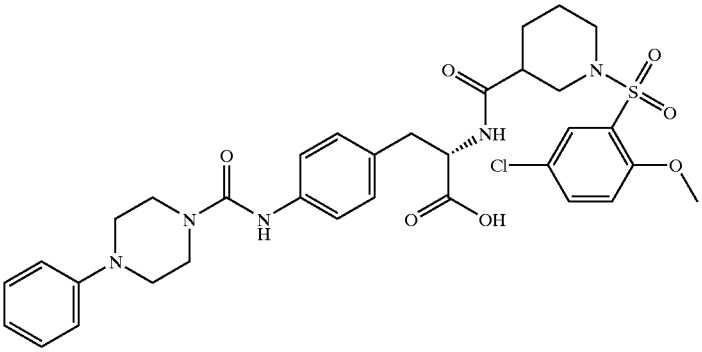 | 684.22 | 684 | 3.1 | 4.38 |
| 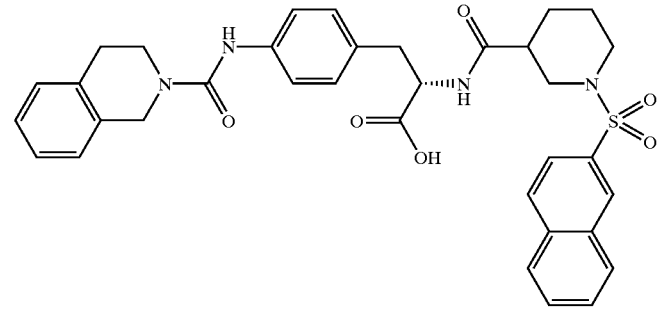 | 640.76 | 641 | 3.1 | 4.39 |
| 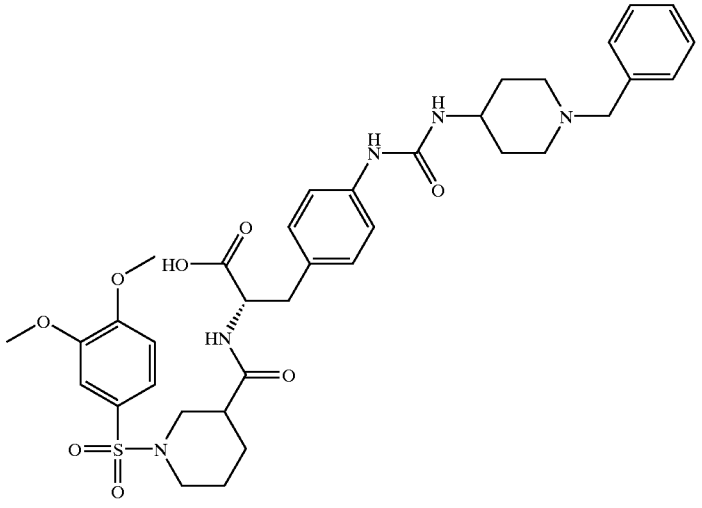 | 707.85 | 708 | 2.1 | 4.40 |
| 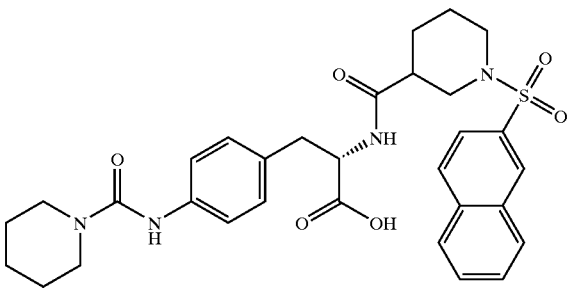 | 592.72 | 593 | 3.0 | 4.41 |

TABLE 3-continued
| structure | MW | MS-ESI | Rt (HPLC) [min] | example |
|---|---|---|---|---|
| 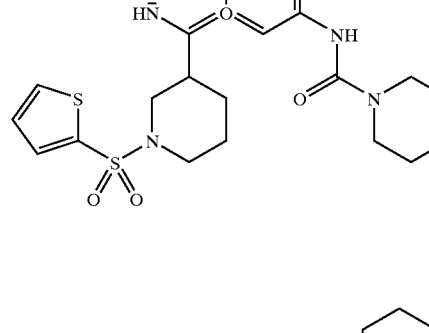 | 550.66 | 551 | 2.4 | 4.42 |
| 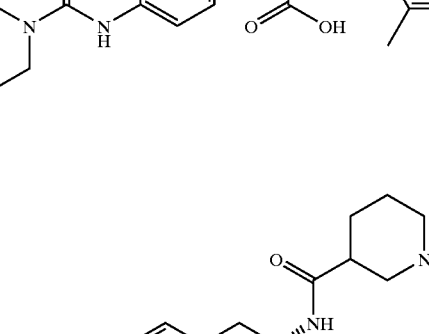 | 558.66 | 559 | 2.6 | 4.43 |
| 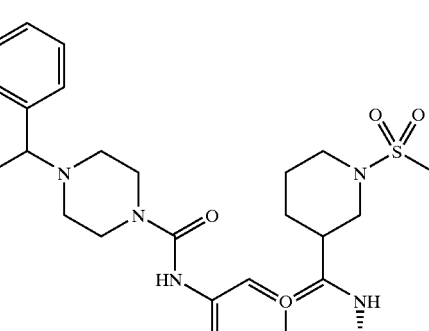 | 558.66 | 559 | 2.5 | 4.44 |
| 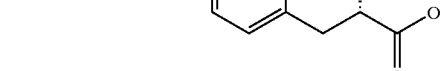 | 769.92 | 770 | 2.7 | 4.45 |

TABLE 3-continued
| structure | MW | MS-ESI | Rt (HPLC) [min] | example |
|---|---|---|---|---|
| 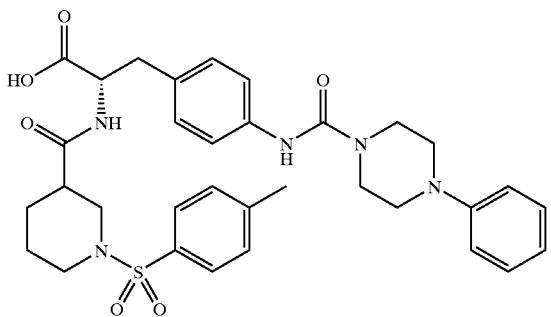 | 633.77 | 634 | 3.0 | 4.46 |
| 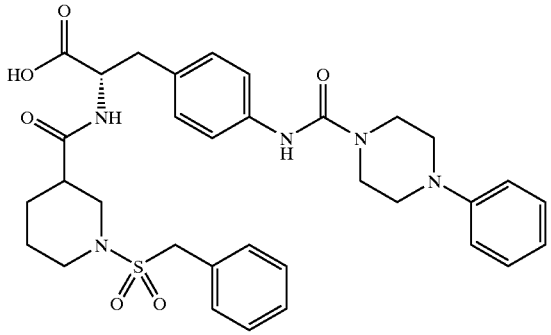 | 633.77 | 634 | 2.9 | 4.47 |
| 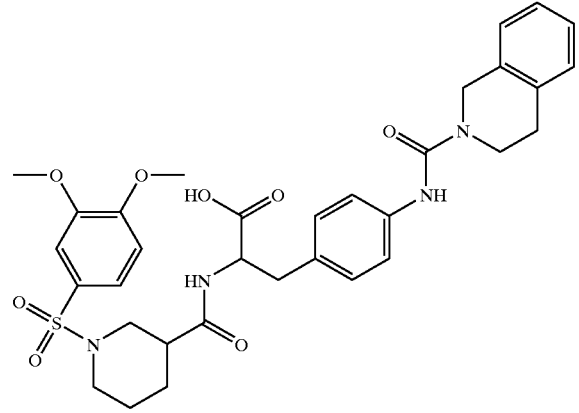 | 650.76 | 651 | 2.9 | 4.48 |
| 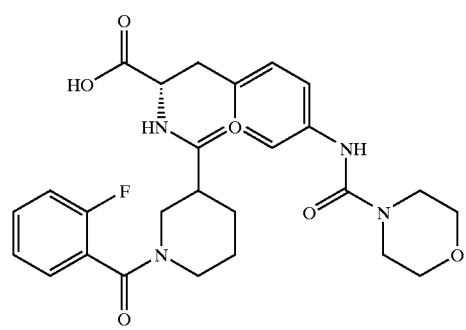 | 526.57 | 527 | 2.2 | 4.49 |

TABLE 3-continued

| structure | MW | MS-ESI | Rt (HPLC) [min] | example |
|---|---|---|---|---|
| 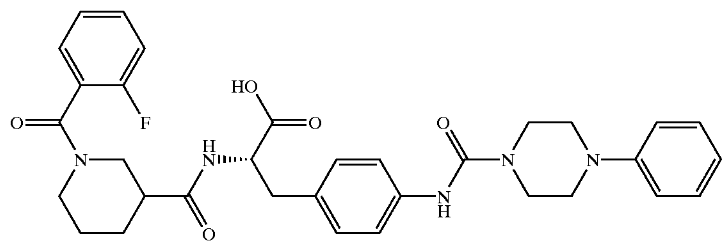 | 601.68 | 602 | 2.7 | 4.50 |
| 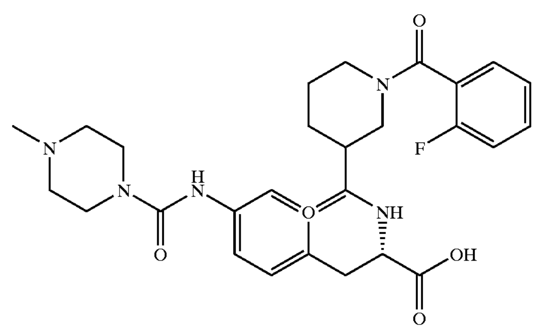 | 539.61 | 540 | 1.5 | 4.51 |
| 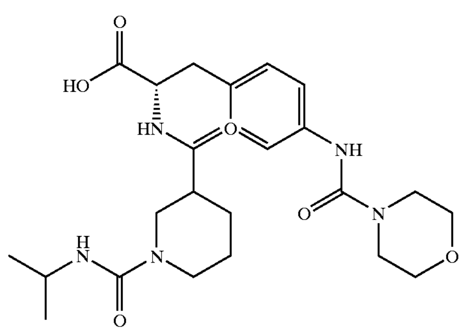 | 489.58 | 490 | 2.0 | 4.52 |
| 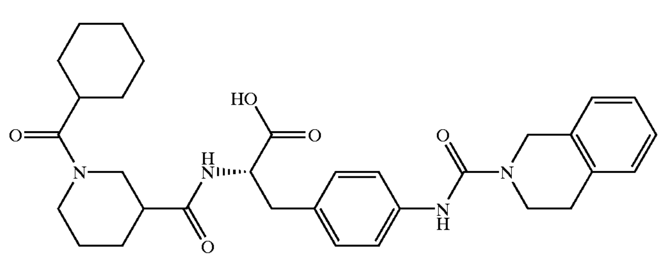 | 560.70 | 561 | 2.9 | 4.53 |
| 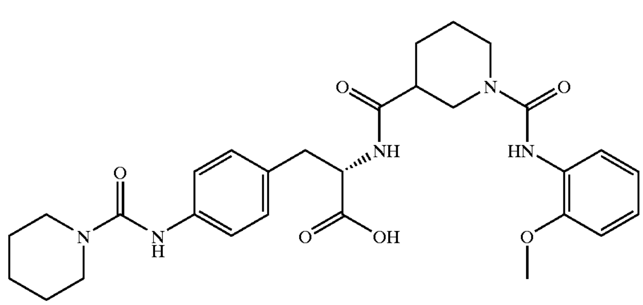 | 551.65 | 552 | 2.7 | 4.54 |

TABLE 3-continued
| structure | MW | MS-ESI | Rt (HPLC) [min] | example |
|---|---|---|---|---|
| 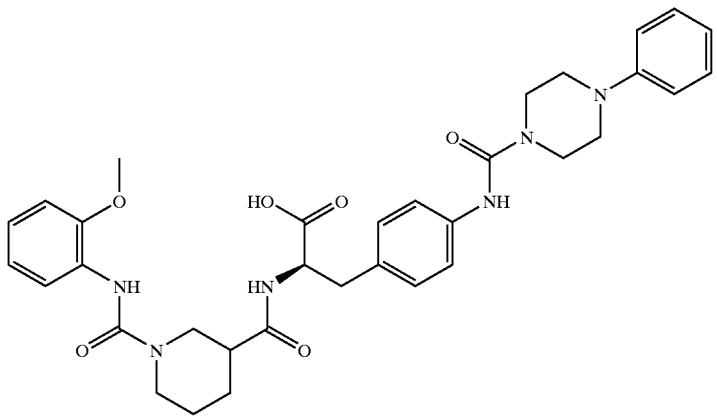 | 628.73 | 629 | 2.8 | 4.55 |
| 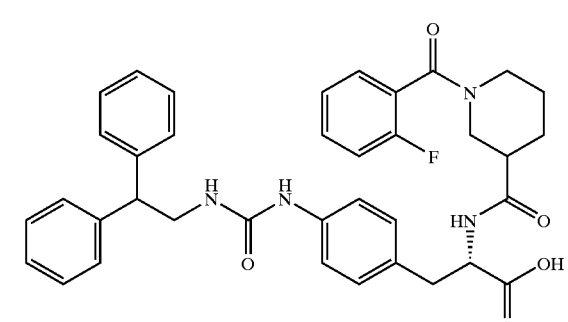 | 636.73 | 637 | 3.0 | 4.56 |
| 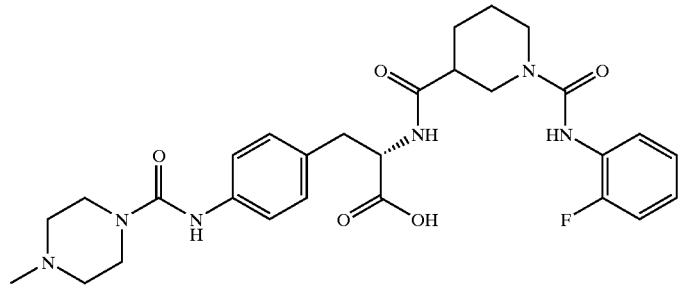 | 554.63 | 555 | 1.4 | 4.57 |
| 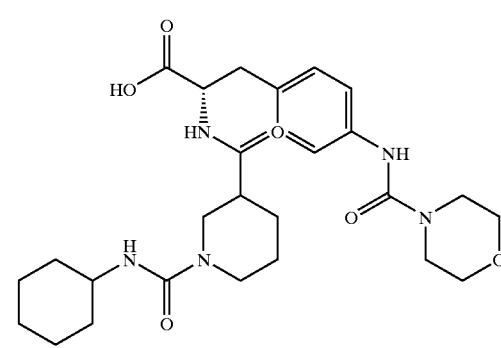 | 529.64 | 530 | 2.3 | 4.58 |

| structure | MW | MS-ESI | Rt (HPLC) [min] | example |
|---|---|---|---|---|
| 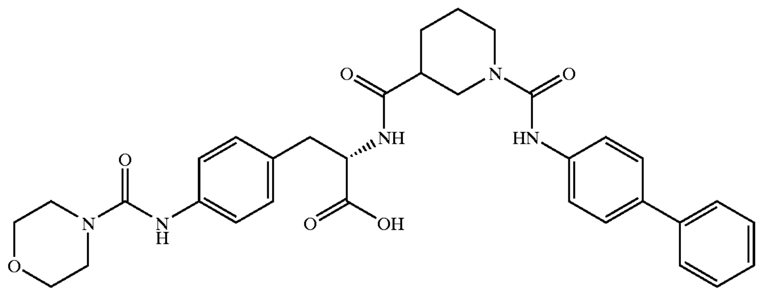 | 599.69 | 600 | 2.7 | 4.59 |
| 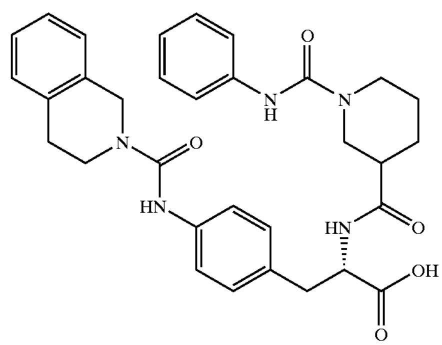 | 569.67 | 570 | 2.8 | 4.60 |
| 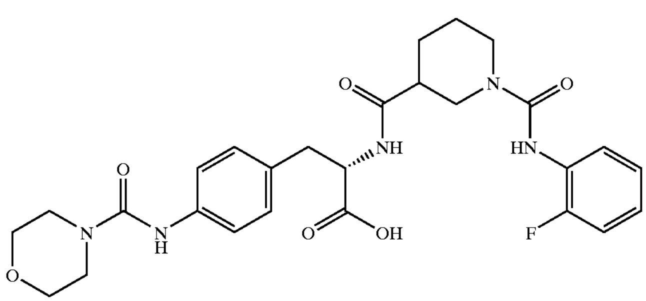 | 541.58 | 542 | 2.2 | 4.61 |
| 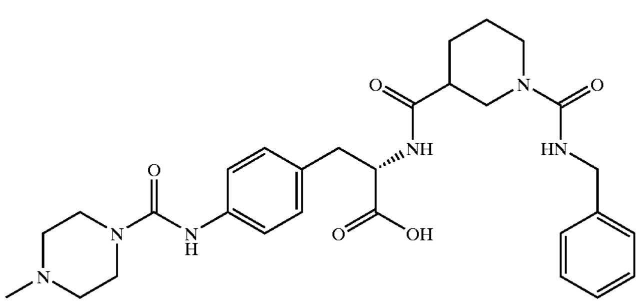 | 550.66 | 551 | 1.6 | 4.62 |

TABLE 3-continued

| structure | MW | MS-ESI | Rt (HPLC) [min] | example |
|---|---|---|---|---|
| 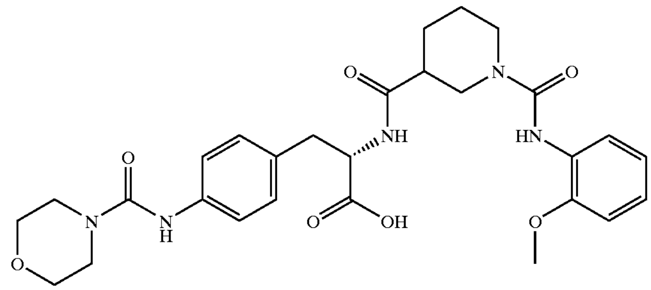 | 553.62 | 554 | 2.3 | 4.63 |

*The retention times were determined by high-performance liquid chromatography (HPLC) by means of UV absorption at 210–216 nm. An acetonitrile/water mixture with 0.05% formic acid was used as eluent with the following method:
0 min. = 10% acetontril, 3 min. = 95% acetonitril, 5.50 min = 95% acetonitril, 5.60 min. = 10% acetonitril.

Example 5

General synthesis scheme:

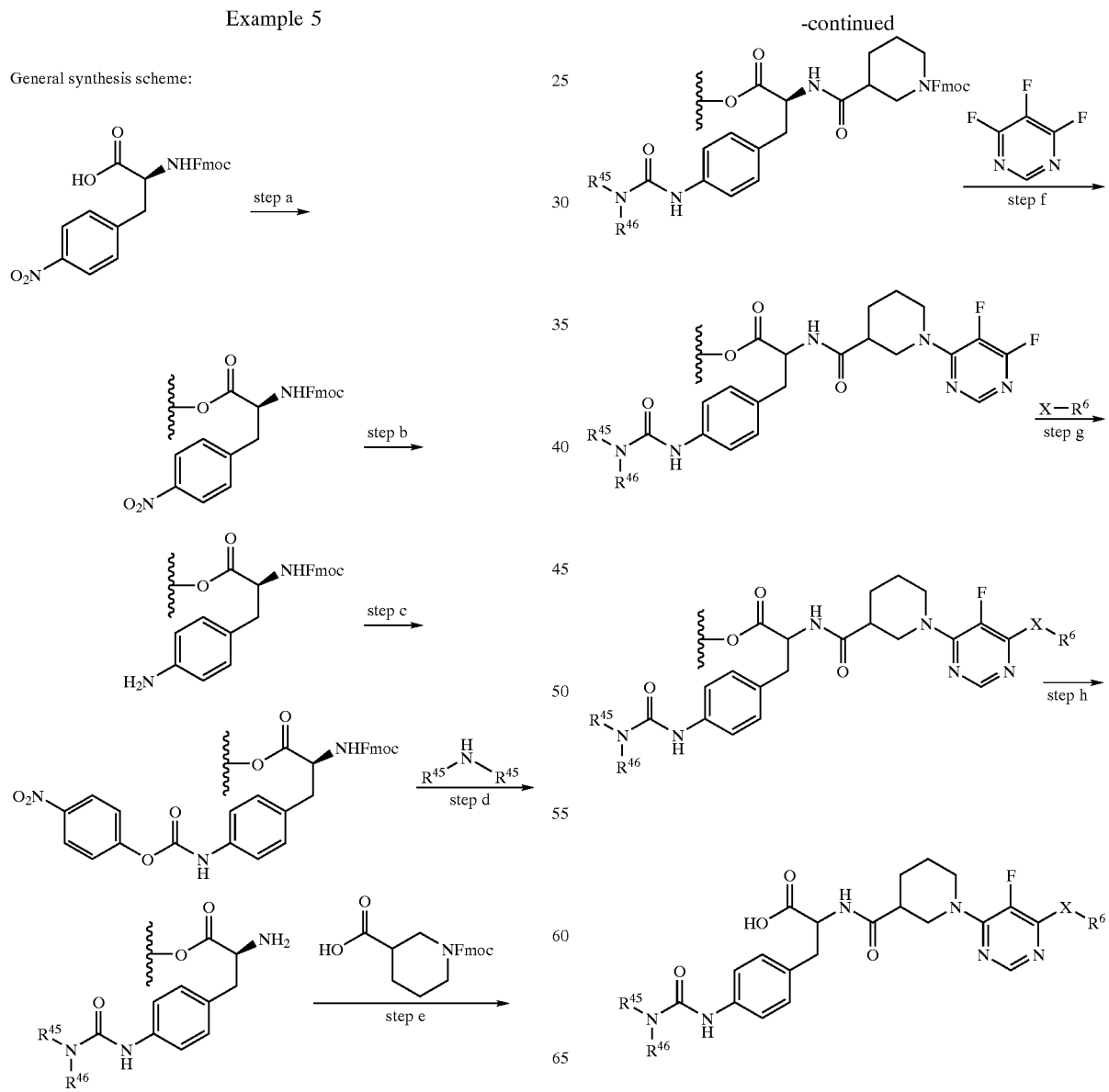

Example 5.1

N-({1-[5-fluoro-6-(4-morpholinyl)-4-pyrimidinyl-3-piperidinyl}carbonyl)-4-{[(4-methyl-1-piperazinyl)carbonyl]amino}-L-phenylalanine

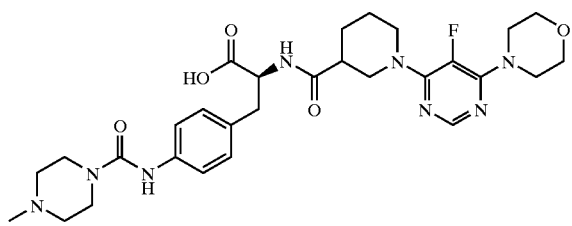

Step a 1.2 g of Wang polystyrene resin (Rapp-Polymere, Tübingen; loading 0.96 mmol/g) are swollen in dimethylformamide. The solvent is filtered off with suction and a solution of 920 mg of 4-nitro-L-phenylalanine in 8 ml dimethylformamide is added. After shaking at room temperature for 15 minutes, the suspension is treated with 304 µl of pyridine and 478 mg of 2,6-dichlorobenzoyl chloride. It is shaken overnight at room temperature. The resin is then washed with dimethylformamide, methanol and dichloromethane.

Step b

The resin is treated with a solution of 5.4 g of tin(II) chloride dihydrate in 12 ml of N-methylpyrrolidone and shaken overnight at room temperature. The resin is then washed with N-methylpyrrolidone, methanol, tetrahydrofuran and dichloromethane.

Step c

A solution of 577 µl diisopropylethylamine in 5 ml dichloromethane and 1.3 g 4-nitrophenylchloroformic acid ester in 5 ml tetrahydrofuran is subsequently given to the resin. After shaking at room temperature for 45 minutes, it is washed with tetrahydrofuran and N-methylpyrrolidone.

Step d

A solution of 774 mg of N-methylpiperazine (amine reagent) and 1.3 ml of diisopropylethylamine in 6 ml N-methylpyrrolidone is added to the resin. After shaking for 2 h, the resin is washed with dimethylformamide, methanol, tetrahydrofuran and dichloromethane.

Step e

A solution of 867 mg O-(7-azabenzotriazol-1-yl)1,1,3,3-tetramethyluronium hexafluorophosphate in 5.7 ml and 397 µl diisopropylethylamine were added to a solution of 801 mg of (3R,S)-N-(9-Fluorenylmethoxycarbonyl)-piperidin-3-carboxylic acid in 5.7 ml dimethylformamide. After shaking the mixture for 15 minutes, the resin was treated with this solution for 4 hours at room temperature. The resin is then washed with dimethylformamide and tetrahydrofuran.

Step f

The derivatized resin is treated with 15 ml of a 20% strength piperidine solution in dimethylformamide and shaken at room temperature for 10 minutes. It is then washed 3 times with dimethylformamide and further 15 ml of a 20% strength piperidine solution in dimethylformamide are added. After shaking for 20 minutes, it is washed with dimethylformamide and tetrahydrofuran. The derivatized resin is treated with a solution of 400 µl of diisopropylethylamine in 12 ml dimethylformamide and a solution of 1.223 g of 4,5,6-trifluoropyrimidine in 12 ml dimethylformamide. It is shaken for 5 hours at room temperature. The derivatized resin is then washed with dimethylformamide.

Step g 794 mg of morpholine (amine reagent) in 12 ml dimethylformamide were added to the derivatized resin and the mixture is shaken overnight at room temperature. The derivatized resin is then washed with dimethylformamide, tetrahydrofuran, dichloromethane.

Step h

For removal of the product, the derivatized resin is shaken with 10 ml of trifluoroacetic acid/dichloromethane 1:1 for 1 hour, filtered off. The filtrate is concentrated in vacuo and purified on silica gel. 100 mg of the title compound are obtained.

Mass spectrometry (ESI): 599.

Retention time (HPLC): 4.1.

TABLE 4

| structure | MW | MS-ESI | Rt (HPLC) [min]* | example |
|---|---|---|---|---|
| 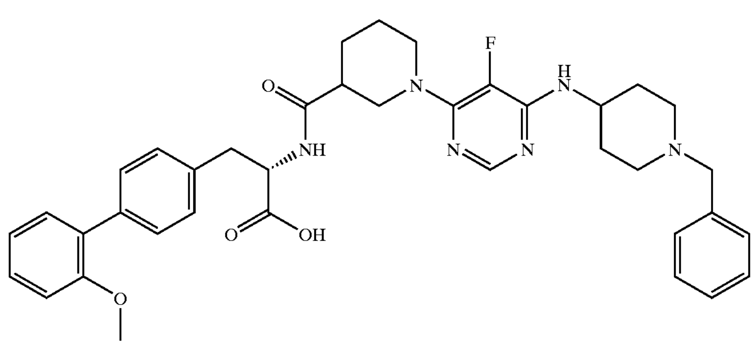 | 666.80 | 667 | 2.3 + 2.4 | 5.2 |

TABLE 4-continued
| structure | MW | MS-ESI | Rt (HPLC) [min]* | example |
|---|---|---|---|---|
| 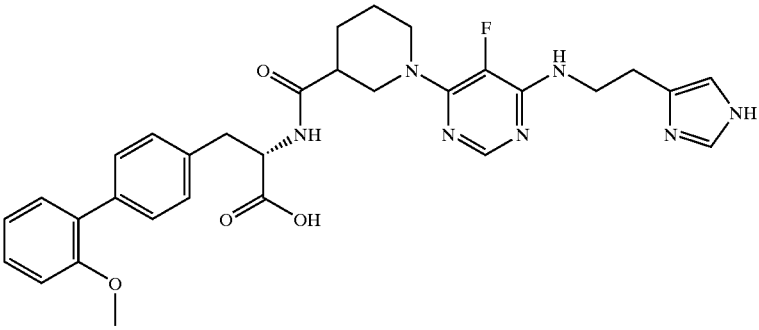 | 587.66 | 588 | 2.2 + 2.3 | 5.3 |
| 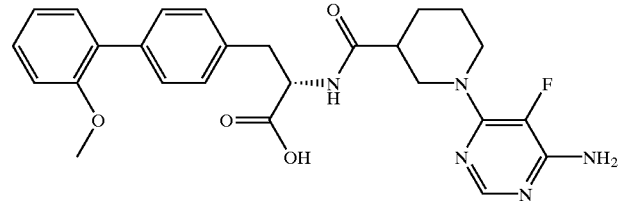 | 493.54 | 494 | 2.4 + 2.5 | 5.4 |
| 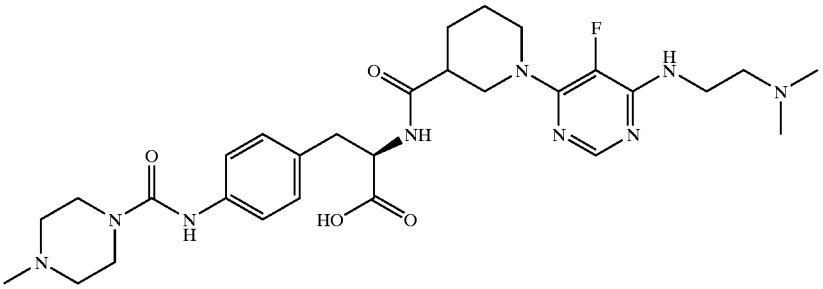 | 599.71 | 600 | 0.3 + 0.4 | 5.5 |

TABLE 4-continued
| structure | MW | MS-ESI | Rt (HPLC) [min]* | example |
|---|---|---|---|---|
| 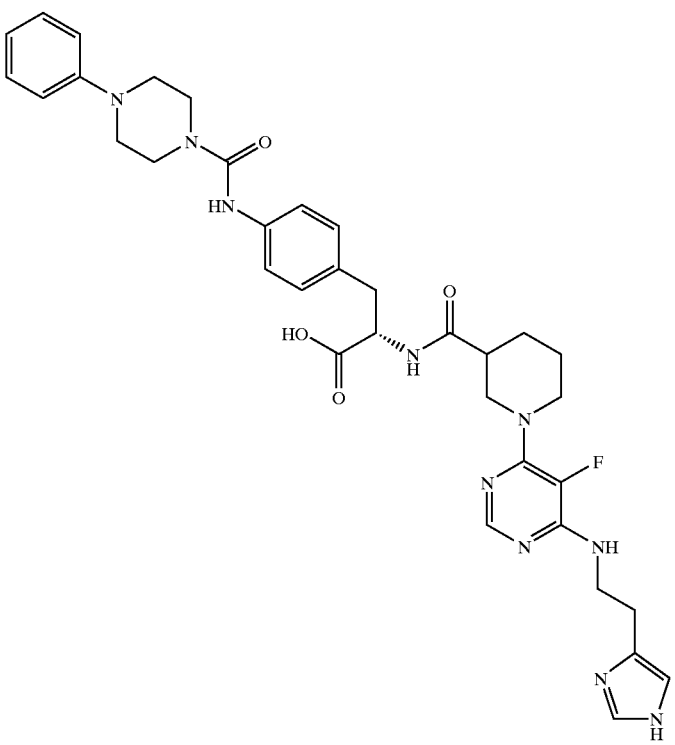 | 684.78 | 685 | 2.1 | 5.6 |
| 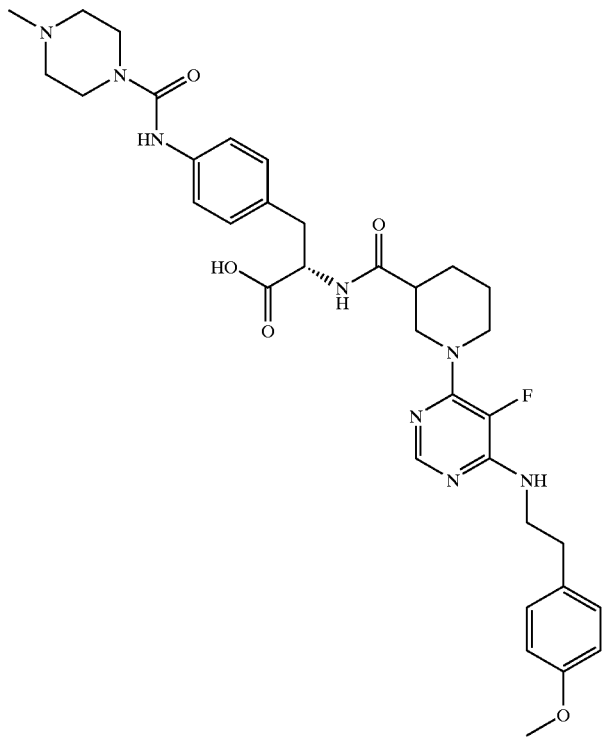 | 662.77 | 663 | 2.0 | 5.7 |

TABLE 4-continued
| structure | MW | MS-ESI | Rt (HPLC) [min]* | example |
|---|---|---|---|---|
| 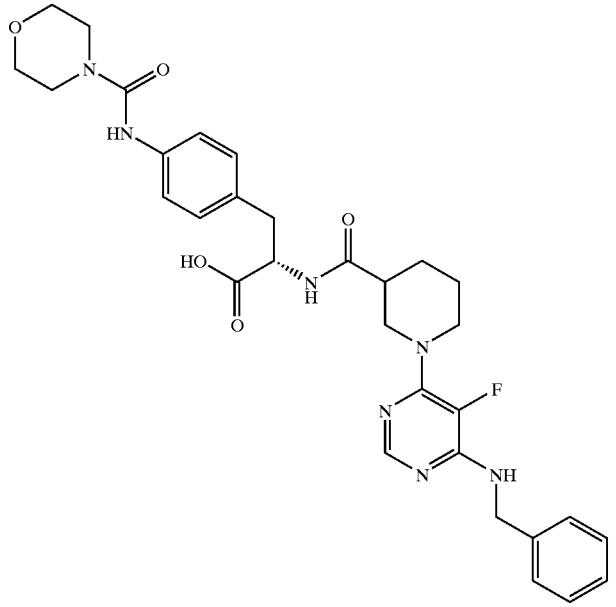 | 605.67 | 606 | 2.6 | 5.8 |
| 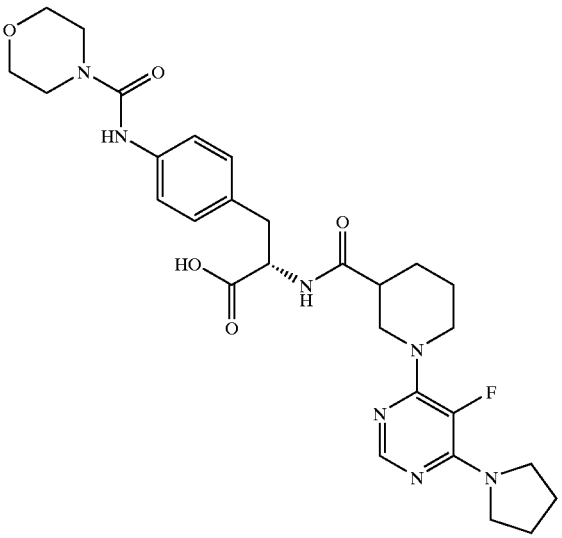 | 569.64 | 570 | 2.2 | 5.9 |

TABLE 4-continued
| structure | MW | MS-ESI | Rt (HPLC) [min]* | example |
|---|---|---|---|---|
| 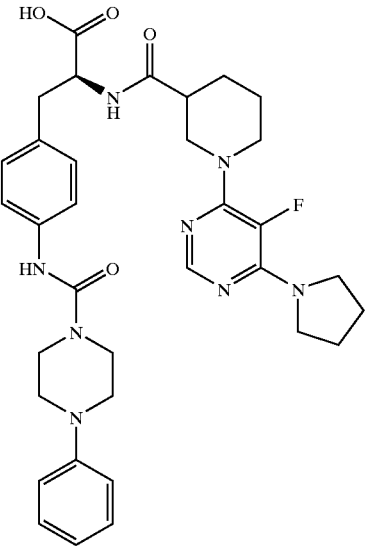 | 644.76 | 645 | 2.7 | 5.10 |
| 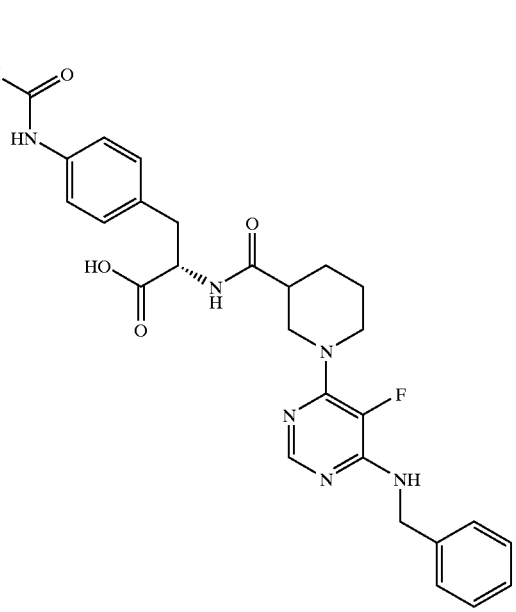 | 618.72 | 619 | 2.0 | 5.11 |

TABLE 4-continued

| structure | MW | MS-ESI | Rt (HPLC) [min]* | example |
|---|---|---|---|---|
| 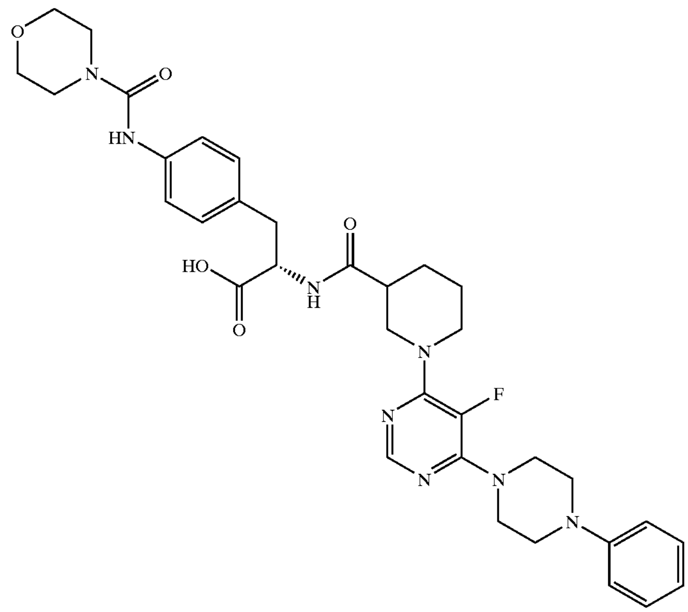 | 660.75 | 661 | 2.8 | 5.12 |
| 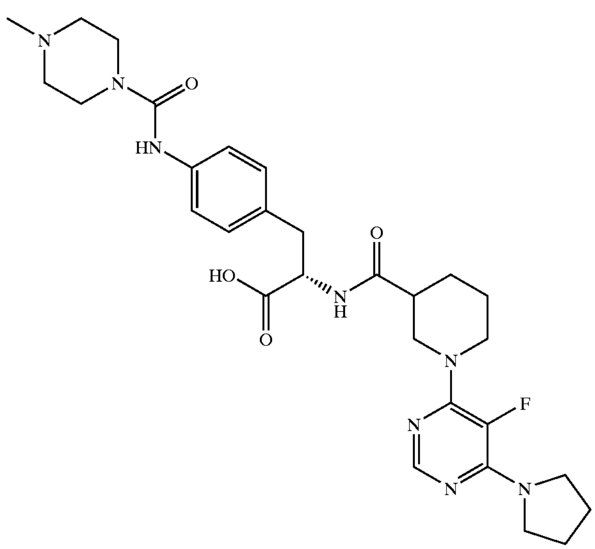 | 582.68 | 583 | 1.7 | 5.13 |

TABLE 4-continued
| structure | MW | MS-ESI | Rt (HPLC) [min]* | example |
|---|---|---|---|---|
| 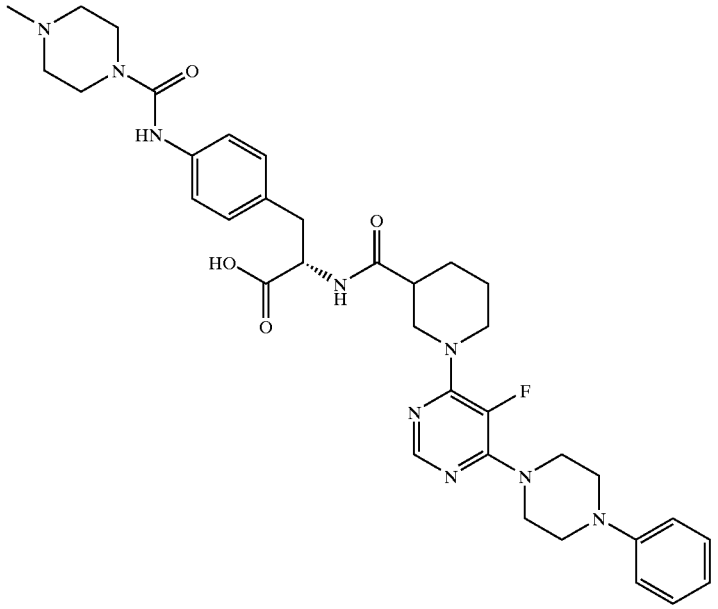 | 673.80 | 674 | 2.2 | 5.14 |
| 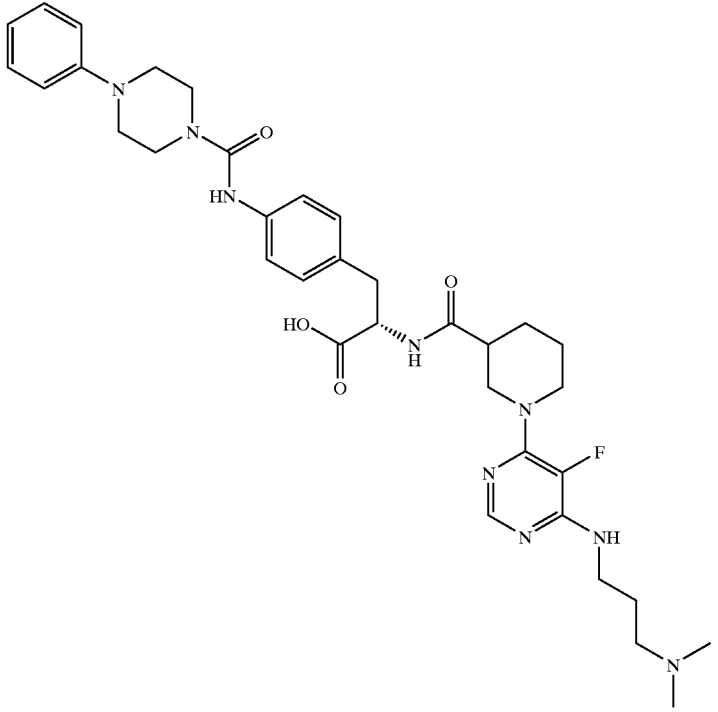 | 675.81 | 676 | 2.1 | 5.15 |

TABLE 4-continued
| structure | MW | MS-ESI | Rt (HPLC) [min]* | example |
|---|---|---|---|---|
| 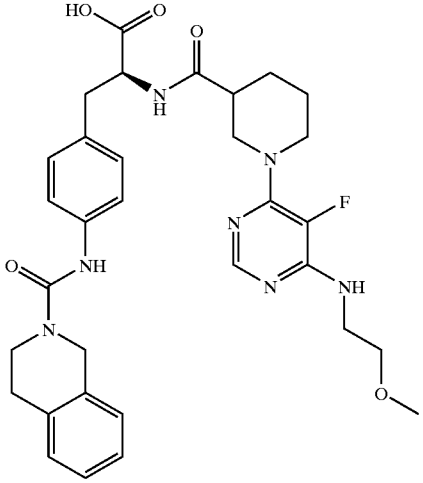 | 619.70 | 620 | 2.7 | 5.16 |
| 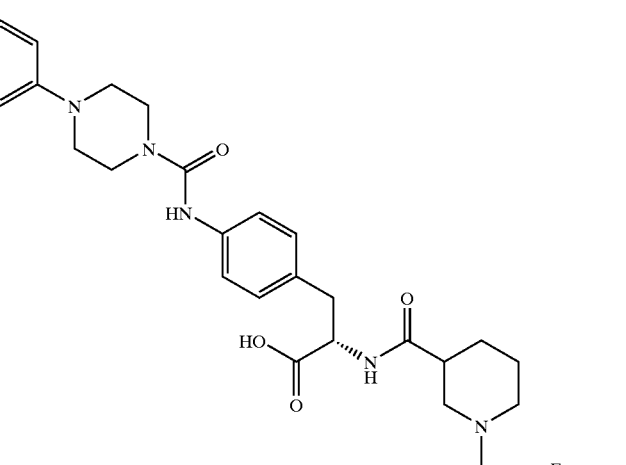 | 676.82 | 677 | 3.1 | 5.17 |

TABLE 4-continued
| structure | MW | MS-ESI | Rt (HPLC) [min]* | example |
|---|---|---|---|---|
| 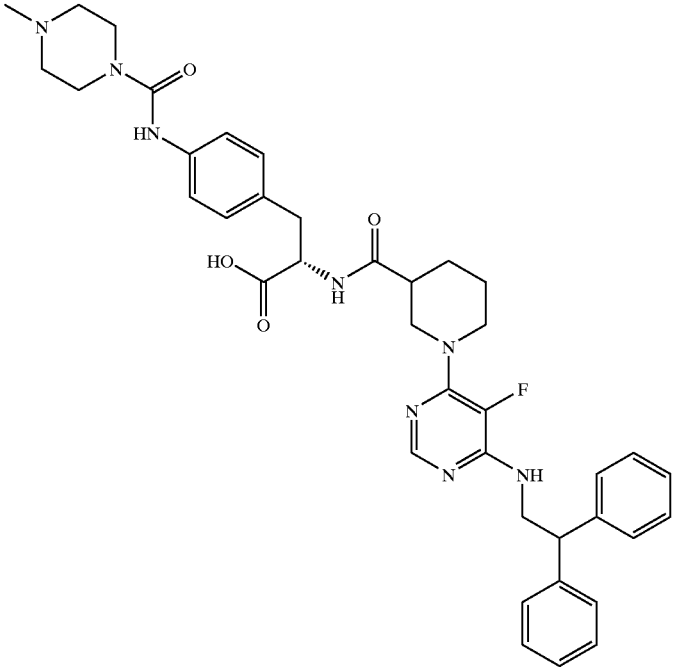 | 708.84 | 709 | 2.4 | 5.18 |
| 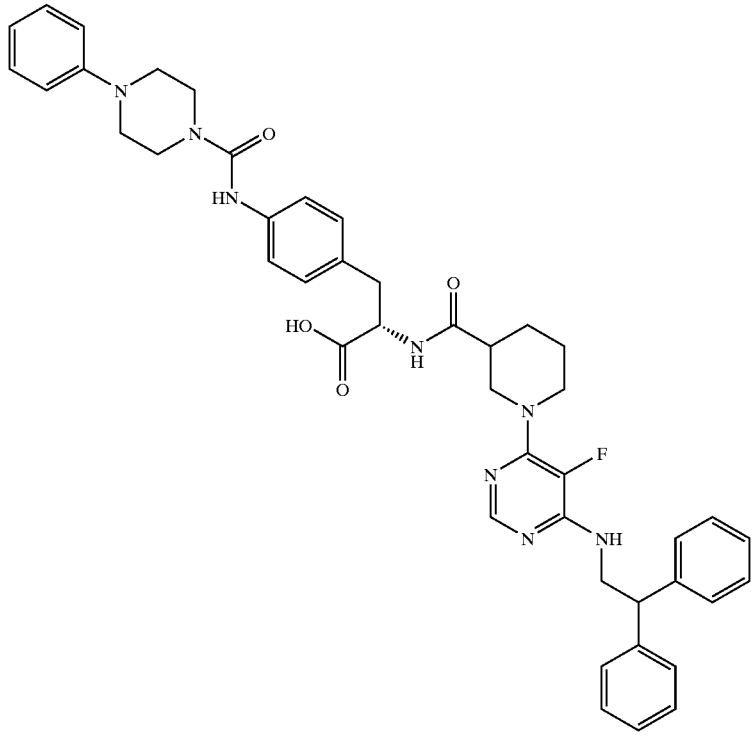 | 770.91 | 771 | 3.3 | 5.19 |

TABLE 4-continued

| structure | MW | MS-ESI | Rt (HPLC) [min]* | example |
|---|---|---|---|---|
| 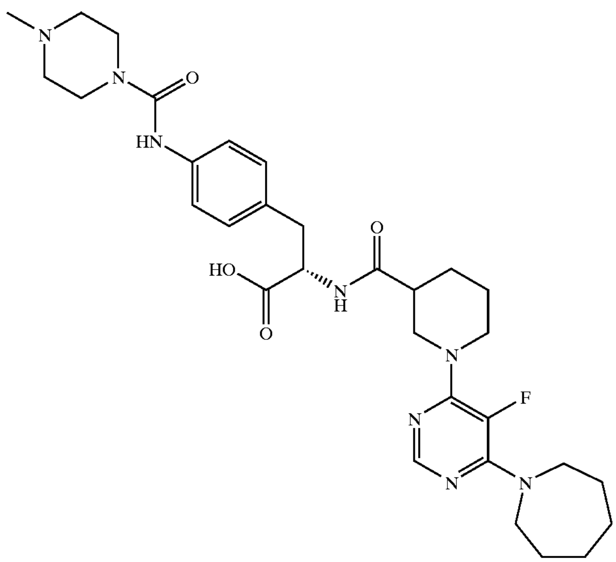 | 610.74 | 611 | 2.1 | 5.20 |
| 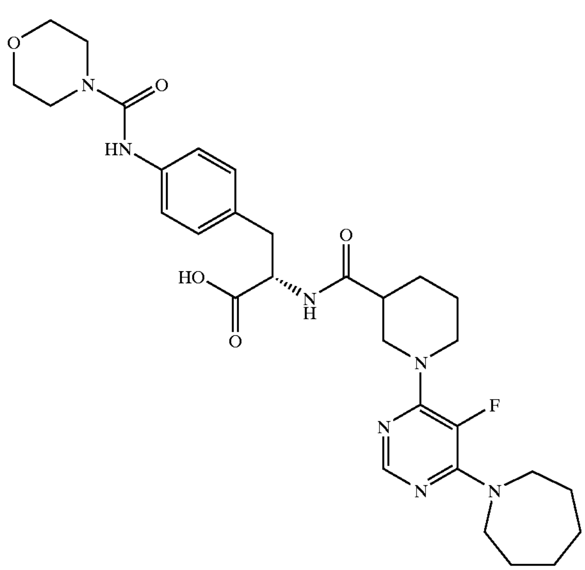 | 597.70 | 598 | 2.6 | 5.21 |

TABLE 4-continued
| structure | MW | MS-ESI | Rt (HPLC) [min]* | example |
|---|---|---|---|---|
| 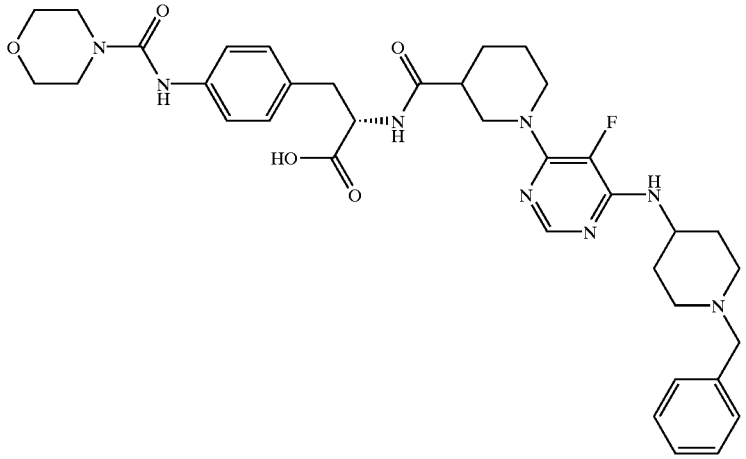 | 688.81 | 689 | 1.9 | 5.22 |
| 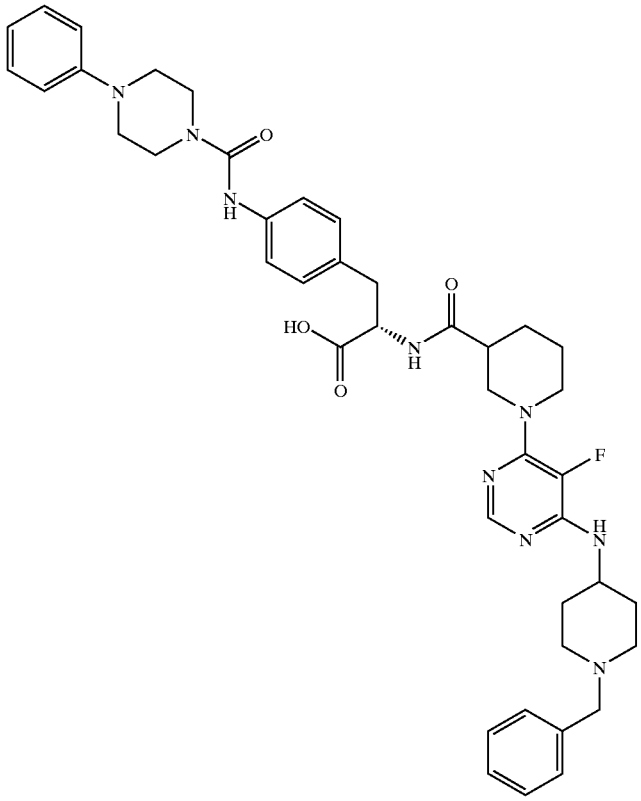 | 763.92 | 764 | 2.3 | 5.23 |

TABLE 4-continued

| structure | MW | MS-ESI | Rt (HPLC) [min]* | example |
|---|---|---|---|---|
| 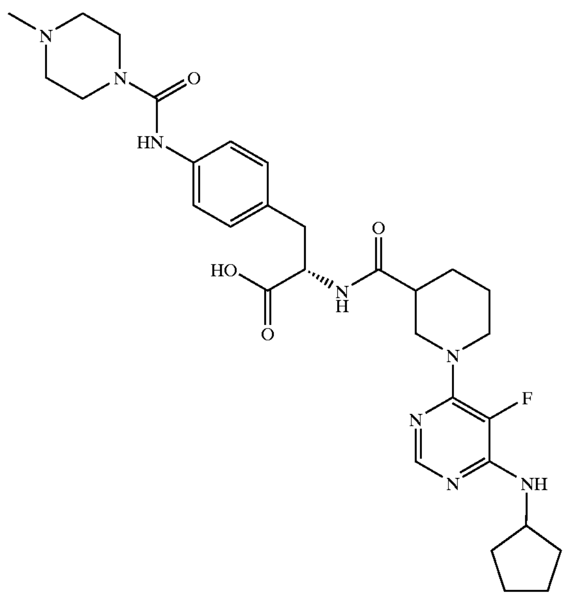 | 596.71 | 597 | 1.9 | 5.24 |
| 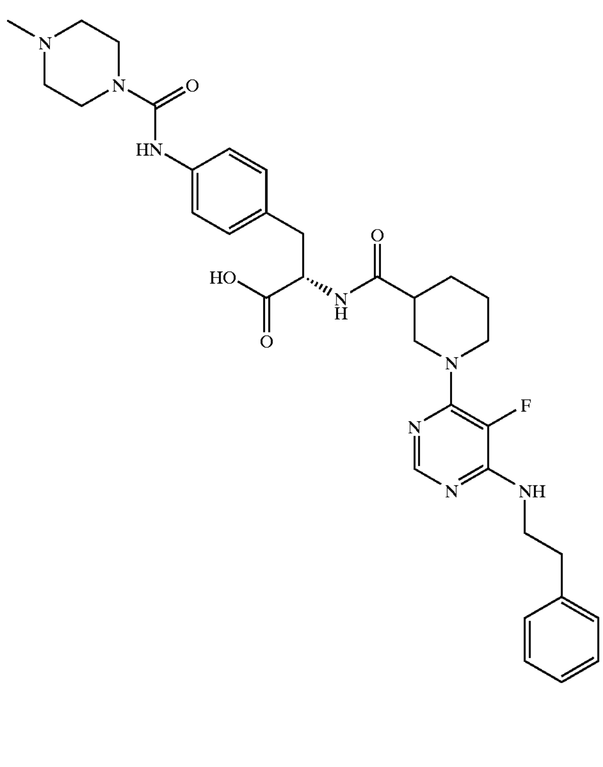 | 632.74 | 633 | 2.1 | 5.25 |

TABLE 4-continued

| structure | MW | MS-ESI | Rt (HPLC) [min]* | example |
|---|---|---|---|---|
| 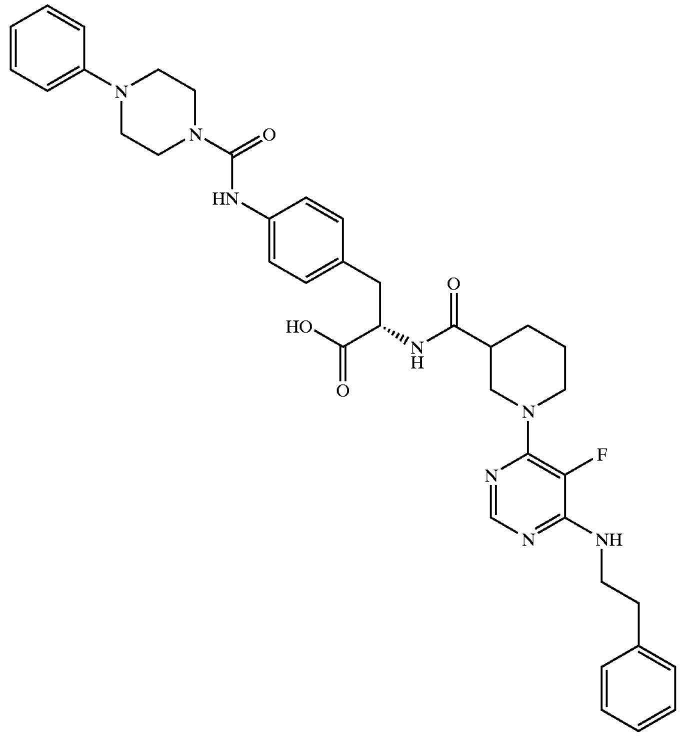 | 694.82 | 695 | 3.1 | 5.26 |
| 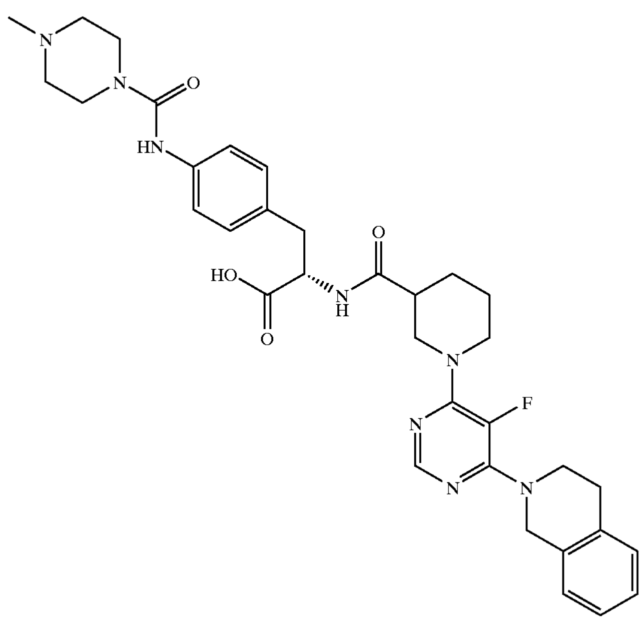 | 644.76 | 645 | 2.2 | 5.27 |

TABLE 4-continued

| structure | MW | MS-ESI | Rt (HPLC) [min]* | example |
|---|---|---|---|---|
| 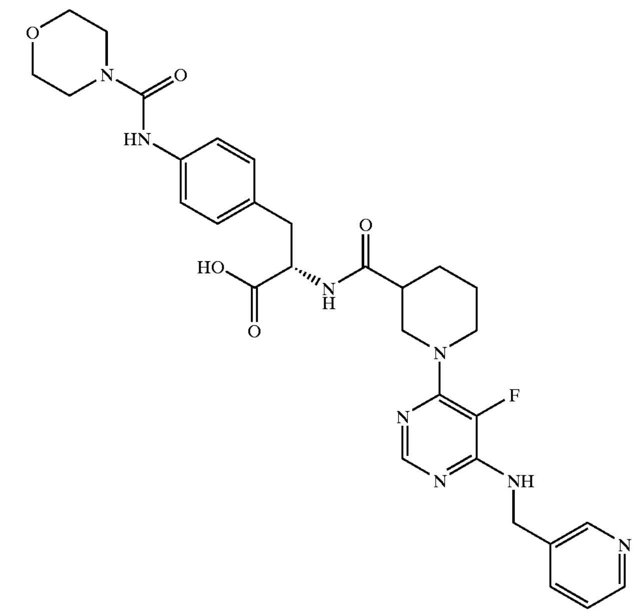 | 606.66 | 607 | 1.8 | 5.28 |
| 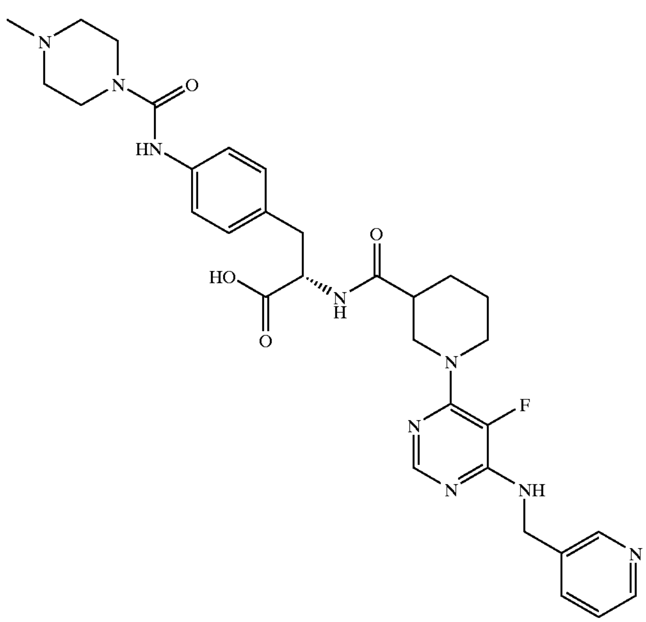 | 619.70 | 620 | 0.3 + 0.5 | 5.29 |

TABLE 4-continued
| structure | MW | MS-ESI | Rt (HPLC) [min]* | example |
|---|---|---|---|---|
| 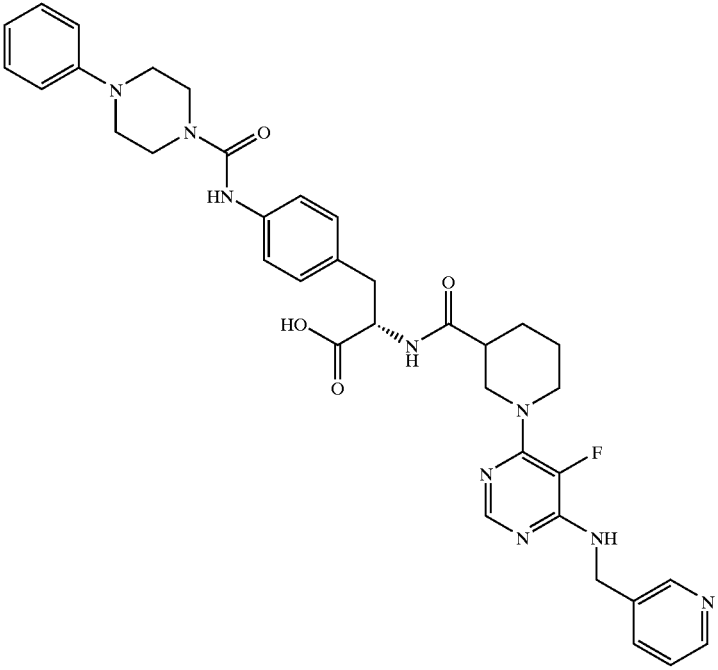 | 681.78 | 682 | 2.3 | 5.30 |
| 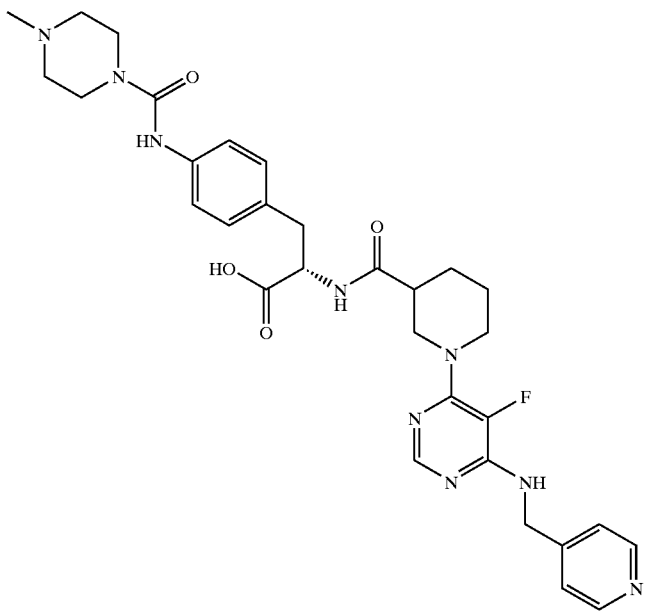 | 619.70 | 620 | 0.3 | 5.31 |

TABLE 4-continued

| structure | MW | MS-ESI | Rt (HPLC) [min]* | example |
|---|---|---|---|---|
| 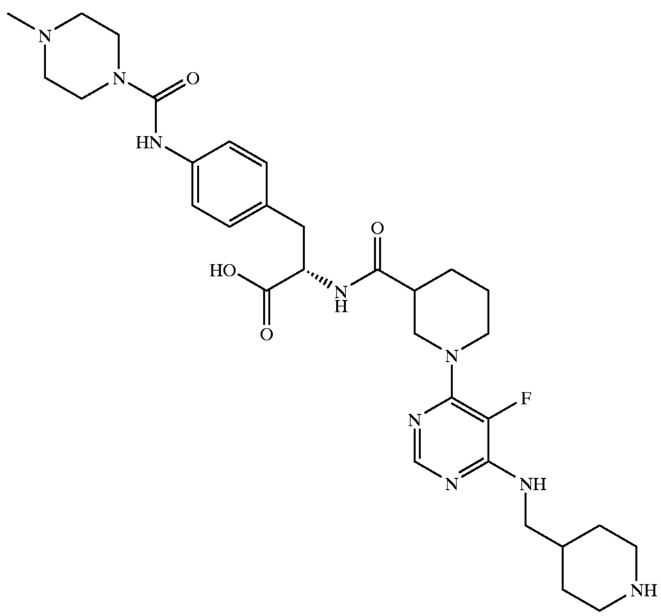 | 625.75 | 626 | 0.3 + 0.4 | 5.32 |
| 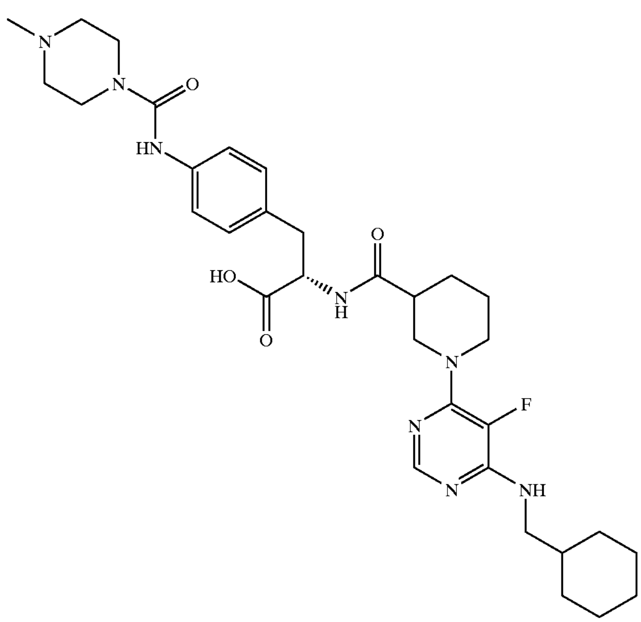 | 624.77 | 625 | 2.2 | 5.33 |

TABLE 4-continued
| structure | MW | MS-ESI | Rt (HPLC) [min]* | example |
|---|---|---|---|---|
| 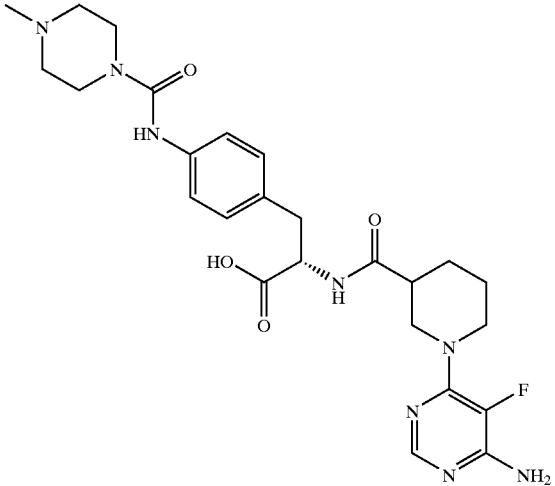 | 528.59 | 529 | 0.3 | 5.34 |
| 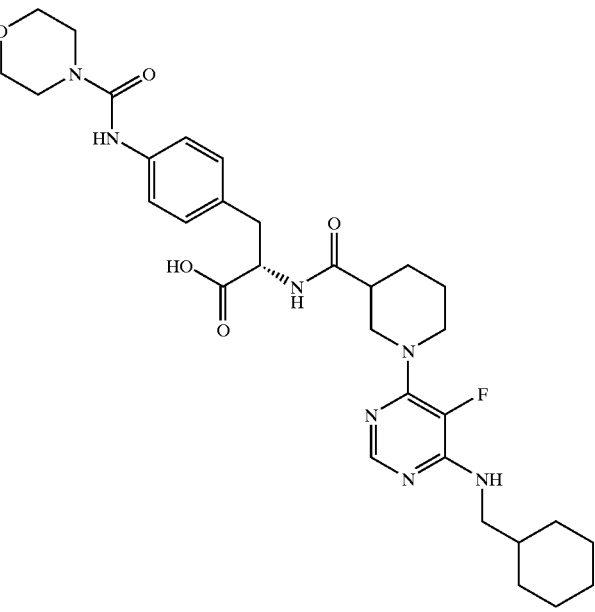 | 611.72 | 612 | 2.7 | 5.35 |

TABLE 4-continued

| structure | MW | MS-ESI | Rt (HPLC) [min]* | example |
|---|---|---|---|---|
| 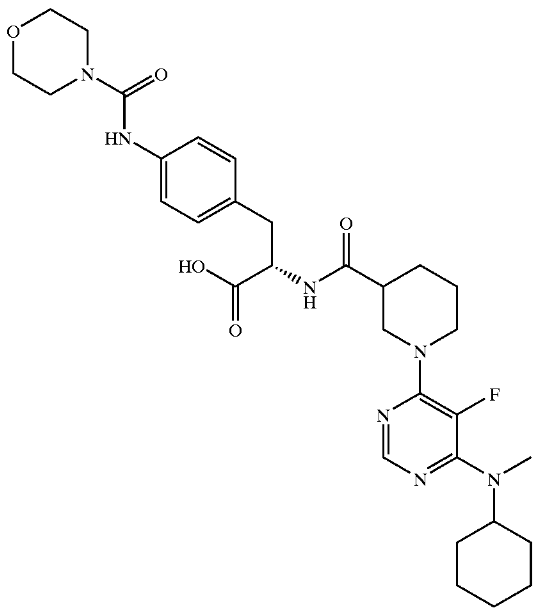 | 611.72 | 612 | 2.8 | 5.36 |
| 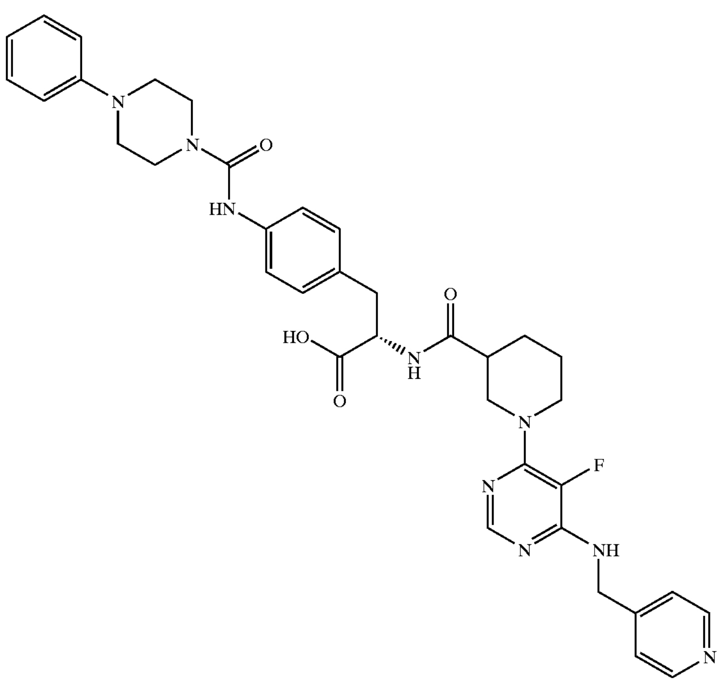 | 681.78 | 682 | 2.2 | 5.37 |

TABLE 4-continued
| structure | MW | MS-ESI | Rt (HPLC) [min]* | example |
|---|---|---|---|---|
| 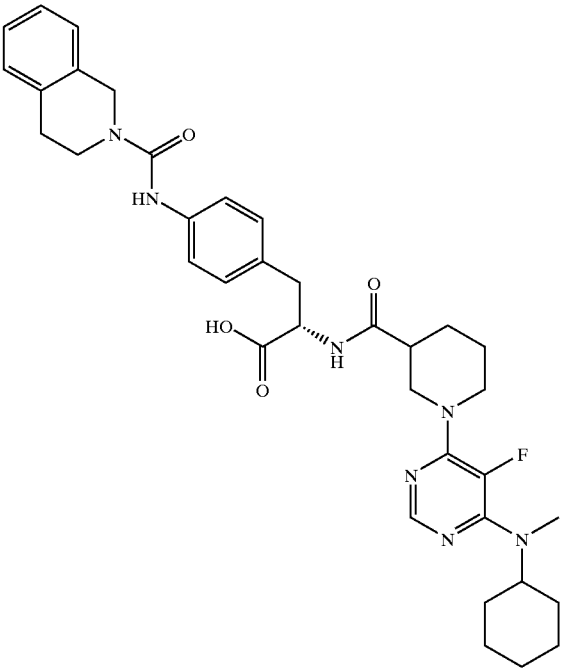 | 657.79 | 658 | 3.3 | 5.38 |
| 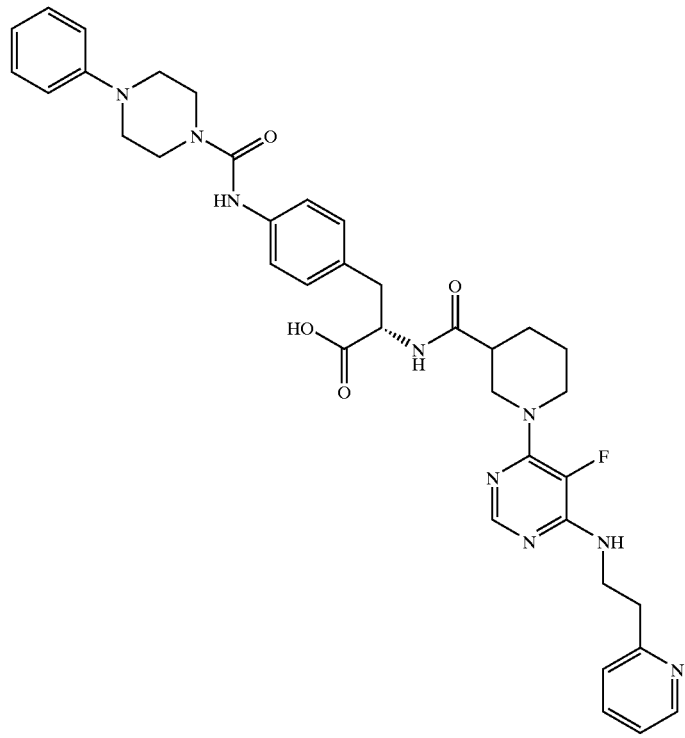 | 695.80 | 696 | 2.3 | 5.39 |

TABLE 4-continued
| structure | MW | MS-ESI | Rt (HPLC) [min]* | example |
|---|---|---|---|---|
| 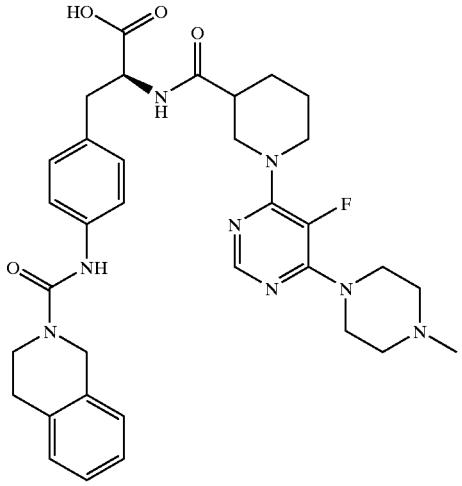 | 644.76 | 645 | 2.1 + 2.2 | 5.40 |
| 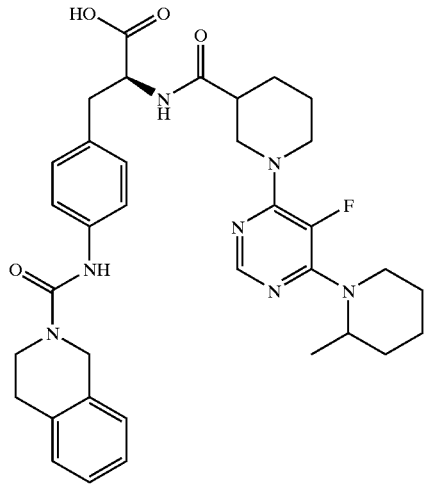 | 643.77 | 644 | 3.1 | 5.41 |
| 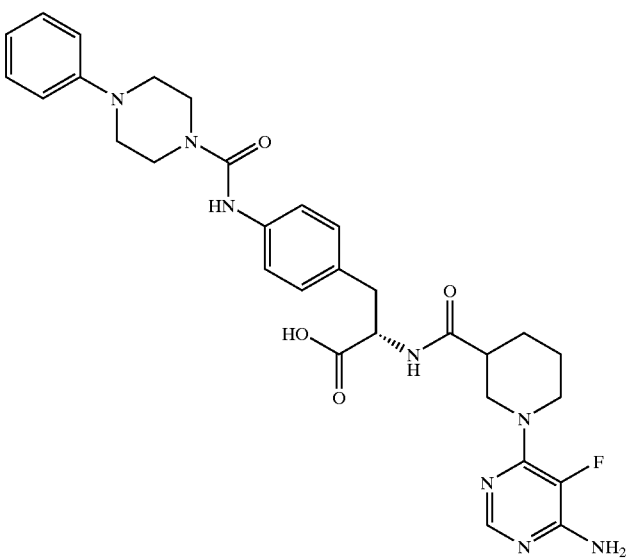 | 590.66 | 591 | 2.4 | 5.42 |

TABLE 4-continued
| structure | MW | MS-ESI | Rt (HPLC) [min]* | example |
|---|---|---|---|---|
| 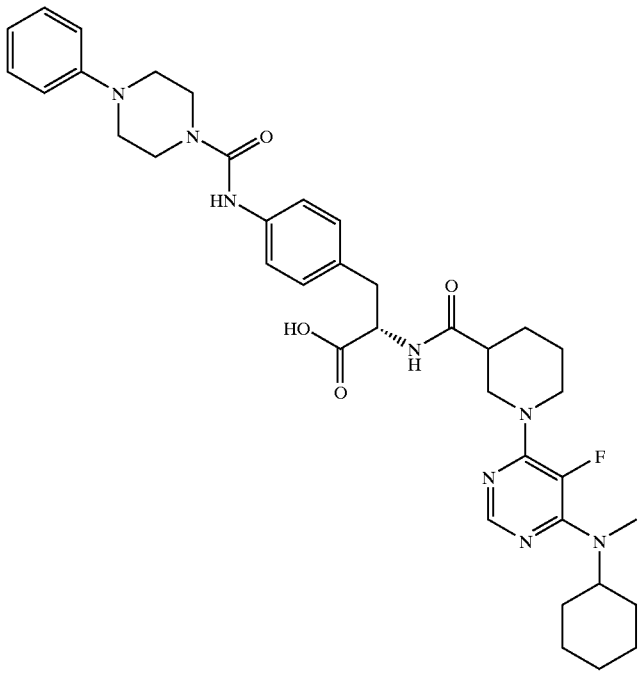 | 686.84 | 687 | 3.2 | 5.43 |
| 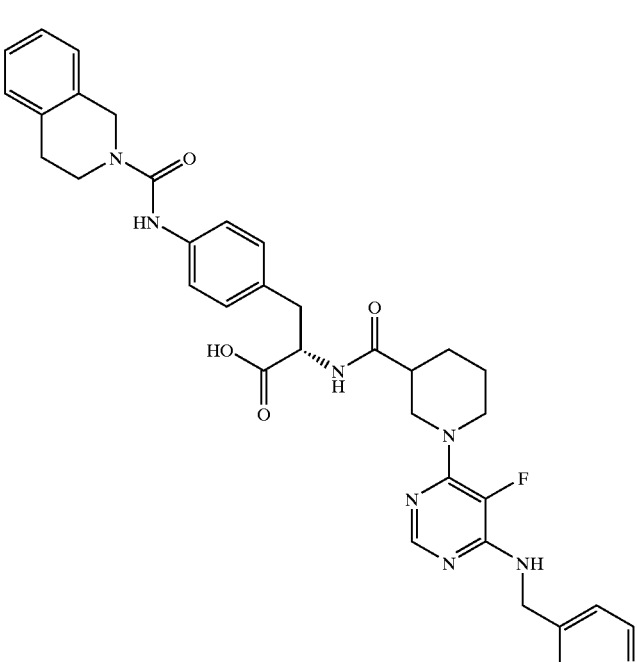 | 652.73 | 653 | 2.3 | 5.44 |

TABLE 4-continued
| structure | MW | MS-ESI | Rt (HPLC) [min]* | example |
|---|---|---|---|---|
| 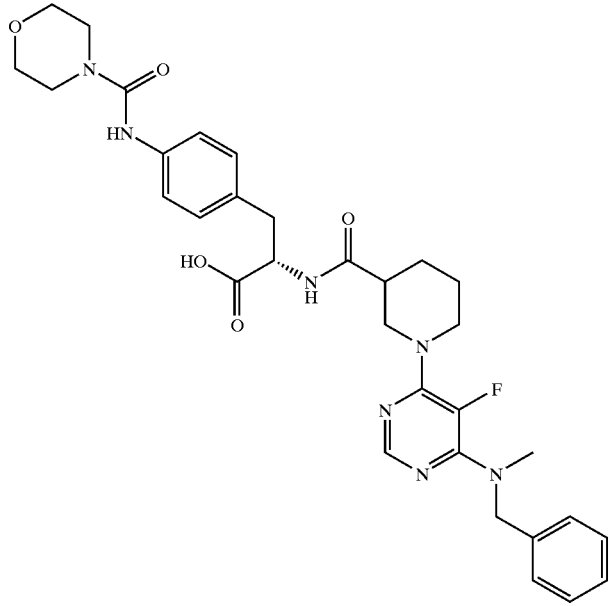 | 619.70 | 620 | 2.7 | 5.45 |
| 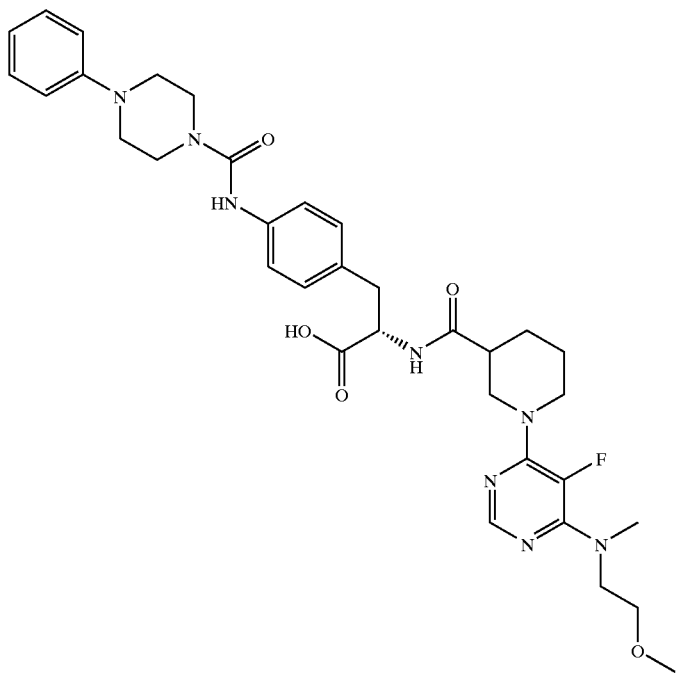 | 662.77 | 663 | 2.8 | 5.46 |

TABLE 4-continued

| structure | MW | MS-ESI | Rt (HPLC) [min]* | example |
|---|---|---|---|---|
| 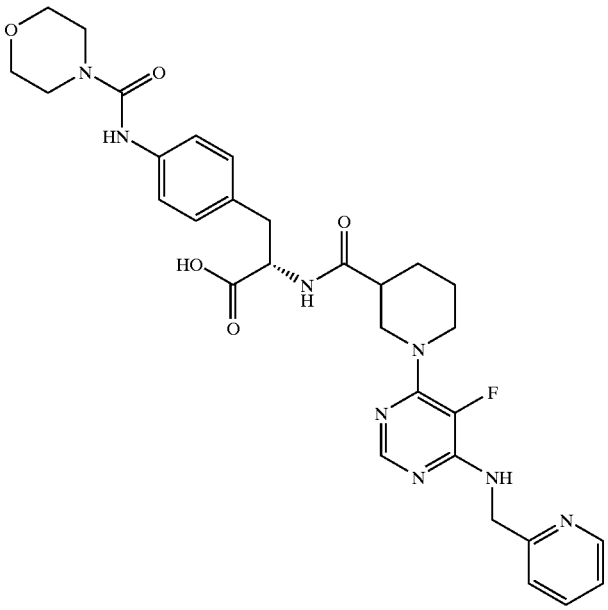 | 606.66 | 607 | 1.9 | 5.47 |

*The retention times were determined by high-performance liquid chromatography (HPLC) by means of UV absorption at 210–216 nm.
An acetonitrile/water mixture with 0.05% formic acid was used as eluent with the following method:
0 min. = 10% acetonitril, 3 min. = 95% acetonitril, 5.50 min = 95% acetonitril, 5.60 min. = 10% acetonitril.

In Vitro Assay: Adhesion of Jurkat Cells to Immobilized VCAM-1 (Domains 1–3).

Preparation of Fluorescence Labeled Jurkat Cells:

Jurkat cells (American Type Culture Collection, Clone E6-1, ATCC TIB-152) were cultured in RPMI 1640 medium (Nikken Bio Medical Laboratory, CM1101) supplemented with 10% fetal bovine serum (Hyclone, A-1119-L), 100 U/ml penicilin (Gibco BRL, 15140-122) and 100 µg/ml streptomycin (Gibco BRL, 15140-122) in a humidified incubator at 37° C. with 5% $CO_2$.

Jurkat cells were incubated with phosphate balanced solution (PBS, Nissui, 05913) containing 25 µM of 5(-and-6)-carboxyfluorescein diacetate, succinimidyle ester (CFSE, Dojindo Laboratories, 345-06441) for 20 min at room temperature while gently swirling every 5 min. After centrifugation at 1000 rpm for 5 min, the cell pellet was resuspended with adhesion assay buffer at a cell density of $2 \times 10^6$ cells/ml. The adhesion assay buffer was composed of 24 mM Tris-HCl (pH 7.4), 137 mM NaCl, 27 mM KCl, 4 mM glucose, 0.1% bovine serum albumin (BSA, Sigma, A9647) and 2 mM $MnCl_2$.

Preparation of VCAM-1 (Extracellular Domains 1–3):

Complementary DNA (cDNA) encoding 7-domain form of VCAM-1 (GenBank accession #M60335) was obtained using Rapid-Screen™ cDNA library panels (OriGene Technologies, Inc) at Takara Gene Analysis Center (Shiga, Japan). The primers used were 5'-CCA AGG CAG AGT ACG CAA AC-3' (sence) and 5'-TGG CAG GTA TTA TTA AGG AG-3' (antisense). PCR amplification of the 3-domain VCAM-1 cDNA was perform using Pfu DNA polymerase (Stratagene) with the following sets of primers: (U-VCAMd1–3) 5'-CCA TAT GGT ACC TGA TCA ATT TAA AAT CGA GAC CAC CCC AGA A-3'; (L-VCAMd1–3) 5'-CCA TAT AGC AAT CCT AGG TCC AGG GGA GAT CTC AAC AGT AAA-3'. PCR cycle was 94° C. for 45 sec, 55° C. for 45 sec, 72° C. for 2 min, repeating 15 cycles. After the purification of the PCR product, the fragment was digested with KpnI-AvrII. The digested fragment was ligated into pBluescript IISK(–) (Strategene), which was linealized by digesting with KpnI-XhoI. The ligation was followed by transformation to a Dam/Dcm methylase-free E. coli strain SCS110 (Strategene) to create the donor plasmid pH7. To direct VCAM-1 molecule into the insect cell secretory pathway, the VCAM-1 coding sequence was fused to signal peptide sequence of honeybee melittin. The resulting melittin-VCAM fusion was placed in correct orientation to the baculoviris polyhedrin promoter. Baculovirus transfer vector containing first 3-domain form VCAM-1 (pH10) was constructed by ligation of 0.9 kb fragment from AvrII/Klenow/BclI digests of pH7 into SalI/Klenow/BamHI digests of pMelBacB (Invitrogen). Recombinant baculovirus was generated by using Bac-N-Blue™ Transfection kit (Invitrogen) according to the manufacture's instruction. The recombinant virus was amplified by infection to High-Five™ insect cells for 5–6 days, and virus titer was determined by plaque assay.

High-Five™ insect cells were pelleted in a 225 ml conical tube by centrifugation at 1000 rpm for 5 min After discarding the supernatant, the pellet was resuspended in $1.5 \times 10^9$ pfu (MOI=5) of high-titer virus solution, followed by incubation for 1.5 hours at room temperature. The cells were pelleted again and washed once in fresh Express Five™ serum free medium. The cells were pelleted again and finally, resuspended in 200 ml of fresh Express Five™ medium, transferred to a 1,000 ml shaker flask, and incubated in a shaker at 27° C., 130 rpm, for 48 hours before the culture supernatant was collected. The purification of 3-domain form of VCAM-1 from the culture supernatant was performed by one-step anion exchange chromatography. Protein concentration was determined by using Coomassie protein assay reagent (Pierce) according to the manufacture's instruction.

Preparation of Microtiter Plates:

Recombinant human VCAM-1 (extracellular domains 1–3) was dissolved at 0.5 μg/ml in PBS. Each well of the microtiter plates (Nalge Nunc International, Fluoronunc Cert, 437958) was coated with 100 μl of substrate or for background control with buffer alone for 15 hours at 4 C. After discarding the substrate solution, the wells were blocked using 150 μl per well of block solution (Kirkegaard Perry Laboratories, 50-61-01) for 90 minutes. The plate was washed with wash buffer containing 24 mM Tris-HCl (pH 7.4), 137 mM NaCl, 27 mM KCl and 2 mM $MnCl_2$ just before addition of the assay solution containing Jurkat cells and VLA-4 inhibitor.

Assay Procedure:

Labeled Jurkat cells were incubated for 30 min at 37 C with each test compounds, at a concentration of 3 μM or at various concentrations ranging from 0.0001 μM to 10 μM using a standard 5-point serial dilution. The assay solution was transfered to the VCAM-1 coated plates at a cell density of $2 \times 10^5$ cells per well and incubated for 1 hour at 37 C. The non-adherent cells were removed by washing the plates 3 times with wash buffer. The adherent cells were broken by addition of 1% Triton X-100 (Nacalai Tesque, 355-01). Released CFSC was quantified fluorescence measurement in a fluorometer (Wallac, ARVO 1420 multilabel counter).

The adhesion of Jurkat cells to VCAM-1 was analyzed by percent binding calculated by the formula:

$$((FTB-FBG)-(FTS-FBG)]/(FTB-FBG) \times 100 = \%$$

binding, where FTB is the total fluorescent intensity from VCAM-1 coated wells without test compound; FBG is the fluorescent intensity from wells lacking VCAM-1 and FTS is the fluorescent intensity from wells containing the test compound of this invention.

$IC_{50}$-values can then be calculated from the resulting % binding, when 100% binding relate to 100% adhesion, 0% inhibition result The test results were shown in tables 5 to 10 below. The data correspond to the compounds as yielded by solid phase synthesis and thus to levels of purity of about 40–90%.

For practical reasons, the compounds are grouped in four classes of activity as follows:

$IC_{50} = A \leq 0.5$ μM$<B \leq 2$ μM$<C \leq 10$ μM$<D$

TABLE 5

| Example | $IC_{50}$ |
|---|---|
| 1.1 | A |
| 1.2 | C–D |
| 1.3 | B |
| 1.4 | B |
| 1.5 | A |
| 1.6 | A |
| 2.1 | A |
| 2.2 | A |
| 2.3 | A |

TABLE 6

| example | $IC_{50}$ |
|---|---|
| 1.7 | C–D |
| 1.8 | C–D |
| 1.9 | C–D |
| 1.10 | C–D |
| 1.11 | C–D |
| 1.12 | C–D |
| 1.13 | C–D |
| 1.14 | C–D |
| 1.15 | C–D |
| 1.16 | C |
| 1.17 | C–D |
| 1.18 | C–D |
| 1.19 | C–D |
| 1.20 | C–D |
| 1.21 | C–D |
| 1.22 | C–D |
| 1.23 | C–D |
| 1.24 | C–D |
| 1.25 | C–D |
| 1.26 | B |
| 1.27 | C–D |
| 1.28 | C–D |
| 1.29 | C–D |
| 1.30 | C–D |
| 1.31 | C |
| 1.32 | C |
| 1.33 | C–D |
| 1.34 | C–D |
| 1.35 | C–D |
| 1.36 | C–D |
| 1.37 | B |
| 1.38 | C–D |
| 1.39 | B |
| 1.40 | C–D |
| 1.41 | C–D |
| 1.42 | B–C |
| 1.43 | C–D |
| 1.44 | C–D |
| 1.45 | C–D |
| 1.46 | C |
| 1.47 | C–D |
| 1.48 | C |
| 1.49 | C–D |
| 1.50 | C |
| 1.51 | C–D |
| 1.52 | C–D |
| 1.53 | C–D |
| 1.54 | C |

TABLE 7

| example | $IC_{50}$ |
|---|---|
| 1.55 | C–D |
| 1.56 | B |
| 1.57 | C–D |
| 1.58 | C–D |
| 1.59 | C–D |
| 1.60 | C–D |
| 1.61 | C–D |
| 1.62 | C–D |
| 1.63 | C–D |
| 1.64 | C–D |
| 1.65 | C–D |
| 1.66 | C–D |
| 1.67 | C–D |
| 1.68 | C–D |
| 1.69 | C–D |
| 1.70 | C–D |
| 1.71 | C–D |
| 1.72 | C–D |
| 1.73 | C–D |
| 1.74 | C–D |
| 1.75 | C–D |

TABLE 7-continued

| example | IC$_{50}$ |
|---|---|
| 1.76 | C–D |
| 1.77 | C–D |
| 1.78 | C–D |
| 1.79 | C–D |
| 1.80 | C–D |
| 1.81 | C–D |
| 1.82 | C–D |
| 1.83 | C–D |
| 1.84 | C–D |
| 1.85 | B |
| 1.86 | C |
| 1.87 | B |
| 1.88 | C |
| 1.89 | C–D |
| 1.90 | C–D |
| 1.91 | C–D |
| 1.92 | C–D |
| 1.93 | C–D |
| 1.94 | C–D |
| 1.95 | C–D |
| 1.96 | C–D |
| 1.97 | C |
| 1.98 | C |
| 1.99 | C–D |
| 1.100 | C–D |
| 1.101 | C–D |
| 1.102 | C–D |
| 1.103 | C–D |
| 1.104 | A |
| 1.105 | C–D |
| 1.106 | C–D |
| 1.107 | C–D |
| 1.108 | C–D |
| 1.109 | C–D |
| 1.110 | C–D |
| 1.111 | C–D |

TABLE 8

| example | IC$_{50}$ |
|---|---|
| 2.4 | C |
| 2.5 | C–D |
| 2.6 | C–D |
| 2.7 | C–D |
| 2.8 | C–D |
| 2.9 | B–C |
| 2.10 | C–D |
| 2.11 | C–D |
| 2.12 | C–D |
| 2.13 | C–D |
| 2.14 | C–D |
| 2.15 | C–D |
| 2.16 | C–D |
| 2.17 | C–D |
| 2.18 | C–D |
| 2.19 | C–D |
| 2.20 | C–D |
| 2.21 | C–D |
| 2.22 | C–D |
| 2.23 | C–D |
| 2.24 | C–D |
| 2.25 | C–D |
| 2.26 | C–D |
| 2.27 | C–D |
| 2.28 | C–D |
| 2.29 | C–D |
| 2.30 | C |
| 2.31 | C–D |
| 2.32 | C–D |
| 2.33 | C–D |
| 2.34 | C |
| 2.35 | C–D |
| 2.36 | C–D |

TABLE 8-continued

| example | IC$_{50}$ |
|---|---|
| 2.37 | C–D |
| 2.38 | C–D |
| 2.39 | B |
| 2.40 | A–B |
| 2.41 | C–D |
| 2.42 | C–D |
| 2.43 | C–D |
| 2.44 | C–D |
| 2.45 | C–D |
| 2.46 | C–D |
| 2.47 | C–D |
| 2.48 | C–D |
| 2.49 | C–D |
| 2.50 | C–D |
| 2.51 | B |
| 2.52 | C–D |
| 2.53 | C |
| 2.54 | A |
| 2.55 | A |
| 2.56 | B–C |

TABLE 9

| example | IC$_{50}$ |
|---|---|
| 4.2 | A |
| 4.3 | B |
| 4.4 | C |
| 4.5 | B |
| 4.6 | A |
| 4.7 | B |
| 4.8 | C |
| 4.9 | A |
| 4.10 | A |
| 4.11 | A |
| 4.12 | A |
| 4.13 | B |
| 4.14 | A |
| 4.15 | B |
| 4.16 | A |
| 4.17 | B |
| 4.18 | A |
| 4.19 | C |
| 4.20 | C |
| 4.21 | B |
| 4.22 | A |
| 4.23 | B |
| 4.24 | B |
| 4.25 | A |
| 4.26 | C |
| 4.27 | A |
| 4.28 | B |
| 4.29 | A |
| 4.30 | A |
| 4.31 | B |
| 4.32 | C |
| 4.33 | A |
| 4.34 | A |
| 4.35 | B |
| 4.36 | C |
| 4.37 | B |
| 4.38 | B |
| 4.39 | C |
| 4.40 | C |
| 4.41 | A |
| 4.42 | A |
| 4.43 | A |
| 4.44 | B |
| 4.45 | B |
| 4.46 | A |
| 4.47 | B |
| 4.48 | A |
| 4.49 | A |
| 4.50 | A |

TABLE 9-continued

| example | IC$_{50}$ |
|---|---|
| 4.51 | A |
| 4.52 | A |
| 4.53 | B |
| 4.54 | B |
| 4.55 | B |
| 4.56 | B |
| 4.57 | B |
| 4.58 | B |
| 4.59 | B |
| 4.60 | B |
| 4.61 | B |
| 4.62 | B |
| 4.63 | B |

TABLE 10

| example | IC$_{50}$ |
|---|---|
| 5.2 | C |
| 5.3 | C |
| 5.4 | B |
| 5.5 | C |
| 5.6 | C |
| 5.7 | B |
| 5.8 | B |
| 5.9 | C |
| 5.10 | C |
| 5.11 | B |
| 5.12 | C |
| 5.13 | C |
| 5.14 | C |
| 5.15 | C |
| 5.16 | C |
| 5.17 | B |
| 5.18 | B |
| 5.19 | B |
| 5.20 | B |
| 5.21 | B |
| 5.22 | C |
| 5.23 | B |
| 5.24 | C |
| 5.25 | B |
| 5.26 | C |
| 5.27 | C |
| 5.28 | B |
| 5.29 | C |
| 5.30 | B |
| 5.31 | B |
| 5.32 | B |
| 5.33 | C |
| 5.34 | A |
| 5.35 | A |
| 5.36 | B |
| 5.37 | B |
| 5.38 | B |
| 5.39 | B |
| 5.40 | B |
| 5.41 | B |
| 5.42 | A |
| 5.43 | B |
| 5.44 | B |
| 5.45 | B |
| 5.46 | B |
| 5.47 | B |

We claim:

1. Compounds of formula (I)

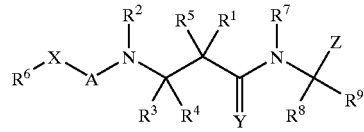

wherein $R^1$, together with the C atom to which it is attached, and $R^2$, together with the N atom to which it is attached, form a piperidinyl ring, $R^3$ represents hydrogen;

$R^4$ represents hydrogen;

$R^5$ represents hydrogen;

$R^6$ represents $(C_1–C_{10})$-alkyl, or $(C_2–C_{10})$-alkenyl, $(C_2–C_{10})$-alkynyl, $C_6$ or $C_{10}$ aryl, $(C_3–C_7)$-cycloalkyl which can optionally be substituted by 1 to 3 radicals $R^{31}$ and which can furthermore be single-foldedly substituted by $(C_3–C_7)$ cycloalkyl, or $C_6$ or $C_{10}$ aryl, which can optionally be substituted by 1 to 3 radicals $R^{31}$, wherein $R^{31}$ represents $OR^{32}$, or halogen, wherein $R^{32}$ represents $(C_1–C_4)$-alkyl $R^7$ represents hydrogen $R^8$ represents hydrogen;

$R^9$ represents $(C_1–C_{10})$-alkyl, $(C_2–C_{10})$-alkenyl, or $(C_2–C_{10})$-alkynyl, each of which can be single-foldedly substituted by $C_6$ aryl, which can furthermore be single-foldedly substituted by $C_6$ aryl, which can optionally be substituted by 1 to 3 radicals $R^{43}$ wherein $R^{43}$ represents halogen;

A represents —C(O)—, or —C(S)—;

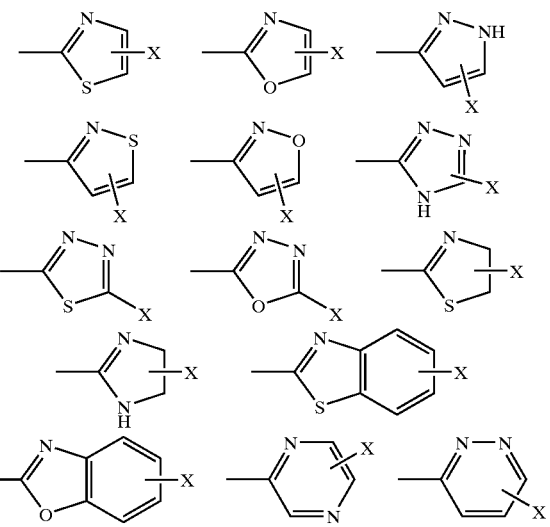

X represents a bond, oxygen or —NR$^{12}$—, wherein $R^{12}$ represents hydrogen, $(C_1–C_4)$-alkyl, $(C_2–C_4)$-alkenyl, or $(C_2–C_4)$-alkynyl;

Y represents oxygen; and
Z represents —C(O)OR$^{47}$,
wherein
R$^{47}$ represents hydrogen;
or a pharmaceutically acceptable salts thereof.

2. A compound according to claim 1, wherein
A represents —C(O)—,

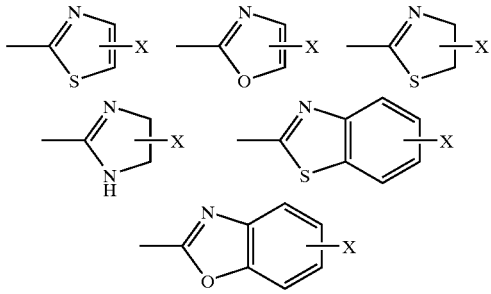

3. A compound according to claim 1 wherein
R$^6$ represents (C$_1$–C$_{10}$)-alkyl, (C$_3$–C$_6$)-cycloalkyl, or C$_6$ or C$_{10}$ aryl, which can optionally be substituted by 1 to 3 residues selected from methoxy, and halogen;
R$^9$ represents C$_1$ alkyl, which is single-foldedly substituted by C$_6$ aryl, which is single-foldedly substituted by C$_6$ aryl, wherein the latter C$_6$ aryl can optionally be substituted by 1 to 2 substituents selected from halogen;
A represents —C(O)—; and
X represents a bond, oxygen or —NR$^{12}$—,
wherein
R$^{12}$ represents hydrogen, or methyl;
acceptable salts thereof.

4. A compounds according to claim 1, wherein
R$^6$ represents (C$_1$–C$_{10}$)-alkyl, (C$_3$–C$_6$)-cycloalkyl, or C$_6$ or C$_{10}$ aryl, optionally substituted by 1 to 3 residues selected from the group methoxy, or halogen and which can furthermore be single-foldedly substituted by C$_6$ cycloalkyl, —C$_6$ or C$_{10}$ aryl, which can optionally be substituted by 1 to 3 residues selected from methoxy, or halogen;
R$^9$ represents C$_1$ alkyl,
which is single-foldedly substituted by C$_6$ aryl, which is single-foldedly substituted by R$^{43}$, A represents —C(O)—,
X represents a bond, oxygen or —NR$^{12}$—; and
R$^{12}$ represents hydrogen, or methyl.

5. A compound selected from the following group:
(2S)-3-(2',5'-dichloro[1,1'-biphenyl]-4-yl)-2-({[1-(2-methoxybenzoyl)-3-piperidinyl]carbonyl}amino) propanoic acid,
(2S)-2-({[1-(2-chlorobenzoyl)-3-piperidinyl] carbonyl}amino)-3-(4'-methyl[1,1'-biphenyl]-4-yl) propanoic acid,
(2S)-2-[({1-[(2,6-dichlorophenyl)sulfonyl]-3-piperdinyl}carbonyl)amino]-3-(2'-methyl[1,1'-biphenyl]-4-yl)propanoic acid,
(2S)-2-({[1-(2-chlorobenzoyl)-3-piperidinyl] carbonyl}amino)-3-(2',4'-dichloro[1,1'-biphenyl]-4-yl) propanoic acid,
(2S)-2-[({1-[(cyclopentyloxy)carbonyl]-3-piperidinyl}carbonyl)amino]-3-(2',5'-dichloro[1,1'-biphenyl]-4-yl)propanoic acid,
(2S)-2-({[1-benzylsulfonyl]-3-piperidinyl] carbonyl}amino)-3-(2',5'-dichloro[1,1'-biphenyl]-4-yl) propanoic acid,
(2S)-3-(2',5'-dichloro[1,1'-biphenyl]-4-yl)-2-{[(1-{5-fluoro-6-[(2-pyridinylmethyl)amino]-4-pyrimidinyl}-3-piperidinyl)carbonyl]amino}propanoic acid,
(2S)-3-(2',5'-dichloro[1,1'-biphenyl]-4-yl)-2-[({1-[5-fluoro-6-(1-piperazinyl)-4-pyrimidinyl]-3-piperidinyl}carbonyl)amino]propanoic acid,
(2S)-3-(2',5'-dichloro[1,1'-biphenyl]-4-yl)-2-[({1-[5-fluoro-6-(4-morpholinyl)-4-pyrimidinyl]-3-piperidinyl}carbonyl)amino]propanoic acid,
(2S)-3-(2',5'-dichloro[1,1'-biphenyl]-4-yl)-2-({[1-(2-pyrimidinyl)-3-piperidinyl]carbonyl}amino)propanoic acid,
(2S)-2-({[1-(1H-benzimidazol-2-yl)-3-piperidinyl] carbonyl}amino)-3-(2',5'-dichloro[1,1'-biphenyl]-4-yl) propanoic acid or
(2S)-3-(2',5'-dichloro[1,1'-biphenyl]-4-yl)-2-({[1-(5-nitro-2-pyridinyl)-3-piperidinyl]carbonyl}amino) propanoic acid.

6. Pharmaceutiacl composition, comprising a compounds according to any one of claims 1, 2, 3, 4 and 5 and a pharmacautically acceptable carrier.

* * * * *